(12) United States Patent (10) Patent No.: US 8,586,297 B2
Pagano et al. (45) Date of Patent: Nov. 19, 2013

(54) MODULATING THE CDC14B-CDH1-PLK1 AXIS AND METHODS FOR SENSITIZING TARGET CELLS TO APOPTOSIS

(75) Inventors: Michele Pagano, New York, NY (US); Florian Bassermann, Munich (DE)

(73) Assignee: New York University, New York, NY (US)

( * ) Notice: Subject to any disclaimer, the term of this patent is extended or adjusted under 35 U.S.C. 154(b) by 0 days.

(21) Appl. No.: 13/489,967

(22) Filed: Jun. 6, 2012

(65) Prior Publication Data

US 2012/0277287 A1 Nov. 1, 2012

Related U.S. Application Data

(62) Division of application No. 12/499,208, filed on Jul. 8, 2009, now Pat. No. 8,216,835.

(60) Provisional application No. 61/081,720, filed on Jul. 17, 2008.

(51) Int. Cl.
*C12Q 1/68* (2006.01)
*C07H 21/02* (2006.01)
*C07H 21/04* (2006.01)
*C12N 15/85* (2006.01)

(52) U.S. Cl.
USPC .............. 435/6; 536/23.1; 536/24.5; 435/325

(58) Field of Classification Search
None
See application file for complete search history.

(56) References Cited

U.S. PATENT DOCUMENTS

| 5,000,000 A | 3/1991 | Ingram et al. |
| 7,241,618 B2 | 7/2007 | Agami et al. |
| 7,439,032 B2 | 10/2008 | Pagano |
| 2004/0077574 A1 | 4/2004 | Klinghoffer et al. |

FOREIGN PATENT DOCUMENTS

| WO | WO03056012 A1 | 7/2003 |
| WO | WO2005042701 A2 | 5/2005 |

OTHER PUBLICATIONS

Crooke, S., Ann. Rev. Medicine, vol. 55, pp. 61-95 (2004).
Peracchi et al., Rev. Med. Virol., vol. 14, pp. 47-64 (2004).
Agrawal et al., Molecular Med. Today, vol. 6, pp. 72-81 (2000).
Chirila et al., Biomaterials, vol. 23, pp. 321-342 (2002).
Opalinska et al., Nature Rev., vol. 1, pp. 503-514 (2002).
Jang et al., Expert Rev. Medical Devices, vol. 1, No. 1, pp. 127-138 (2004).
Sequence Alignment Data (2011) in the Office Action dated Feb. 24, 2011.
Sun, L., Hui, A. M., Su, Q., Vortmeyer, A., Kotliarov, Y., Pastorino, S., Passaniti, A., Menon, J., Walling, J., Bailey, R, et al. (2006).
"Neuronal and glioma-derived stem cell factor induces angiogenesis within the brain" Cancer Cell 9, 287-300.
Tomlins, S. A., Mehra, R., Rhodes, D. R., Cao, x., Wang, L, Dhanasekaran, S. M., Kalyana-Sundaram, S., Wei, J. T., Rubin, M. A., Pienta, K. 1., et al. (2007). "Integrative molecular concept modeling of prostate cancer progression" Nat Genet 39, 41-51.
Amador, V., et al., "APC/C(Cdc20) controls the ubiquitin-mediated degradation ofp21 in prometaphase", Mol. Cell, vol. 27, pp. 462-473, 2007.
Jin, J., et al., "SCFbetaTRCP links Chk1 signaling to degradation of the Cdc25A protein phosphatase", Genes Dev., vol. 17, pp. 3062-3074, 2003.
Lukas, C., et al., "Accumulation of cyclin Bi requires E2F and cyclin-A-dependent rearrangement of the anaphase-promoting complex", Nature, vol. 401, pp. 815-818,1999.
Bartek J and Lukas L et al., "DNA damage checkpoints: from initiation to recovery or adaptation", Curr Opin Cell Biol 19:238-245 (2007).
Busino L et al., "Degradation of Cdc25A by bTrCP during S phase and in response to DNA damage", Nature 426: 87-91. (2003).
Cho P et al., "The dual-specificity phosphatase CDC14B bundles and stabilizes mictotubules", Mol Cell Bioi 25; 4541-4551.(2005).
D'Amours D et al., "At the interface between signaling and executing anaphase-Cdc14 and the FEAR network.", Genes Dev 18; 2581-2595. (2004).
Donzelli M et al., "Dual mode of degradation of Cdc25 A phosphatase", EMBO J 21; 4875-4884 (2002).
Dorrello NV et al., "S6K1- and bTRCP-mediated degradation of PDCD4 promotes protein translation and cell gro'Nth", Science 314: 467-471(2006).
Guardavaccaro, D., and Pagano, M. (2006). Stabilizers and destabilizers controlling cell cycle oscillators, Mol Cell 22, 1-4.
Harper, w., and Elledge, S. J. (2007). The DNA damage response: ten years after, Mol Cell 28, 739-745.
Kaiser, B. K., Nachury, M. V., Gardner, B. E., and Jackson, P. (2004). Xenopus Cdc14 a/Pare localized to the nucleolus and centrosome and are required for embryonic cell division, BMC Cell Bioi 5, 27.

(Continued)

*Primary Examiner* — Amy Bowman
(74) *Attorney, Agent, or Firm* — Troutman Sanders LLP

(57) ABSTRACT

The invention relates to modulating Cdc14B levels (cell division cycle 14 homolog B) and/or Cdh1 (Fzr1 protein, CDC20-like 1b, or fizzy-related protein) levels to sensitize cells to DNA damage by increasing the abundance of Plk1 (polo-like kinase 1) in a target cell. In certain embodiments, the invention relates to modulating Plk1 levels, and in particular to increasing Plk1 levels, to sensitize target cells such as cancer cells to cell death or apoptosis. In certain embodiments, the invention relates to inhibitors of Cdc14B and Cdh1 that sensitize tumor cells to chemotherapy or radiation induced cell death or apoptosis. In addition to applications relating to cancer therapies and diagnostics, the Plk1 modulators and assays will be employed for identifying novel drugs or drug candidates useful for various proliferative and/or differentiative disorders such as major opportunistic infections, immune disorders, cardiovascular diseases and inflammatory disorders.

5 Claims, 21 Drawing Sheets

(56) References Cited

OTHER PUBLICATIONS

Kastan, M., and Bartek, I (2004). Cell-cycle checkpoints and cancer. Nature 432,316323.

Lin, S. Y., Li, K., Stewart, G., and Elledge, S. (2004). Human Claspin works with BRCAI to both positively and negatively regulate cell proliferation. Proc Natl Acad Sci USA 101, 6484-6489.

Lindon, C., and Pines, J. et al., (2004). "Ordered proteolysis in anaphase inactivates Plkl to contribute to proper mitotic exit in human cells" J Cell Bioi 164,233-241.

Liu, H., Cheng, E. H., and Hsieh, J. J. et al., (2007). Bimodal degradation of MLL by SCFSkp2 and APCcdc20 assures cell cycle execution: a critical regulatory circuit lost in leukemogenic MLL fusions, Genes Dev 21, 2385-2398.

Mailand, N., Bekker-Jensen, S., Bartek, J., and Lukas, 1. (2006). "Destruction of Claspin by SCFbTrCP restrains Chkl activation and facilitates recovery from genotoxic stress", Mol Cell 23, 307-318.

Mailand, N., Lukas, C., Kaiser, B., Jackson, P., Bartek, J., and Lukas, 1. (2002). "Deregulated human Cdc14A phosphatase disrupts centrosome separation and chromosome segregation", Nat Cell Bioi 4, 317-322.

Mamely, L, van Vugt, M., Smits, V., Semple, 1., Lemmens, B., Perrakis, A, Medema, R, and Freire, R (2006). "Polo-like kinase-I controls proteasome-dependent degradation of Claspin during checkpoint recovery", Curr Bioi 16, 1950-1955.

Mitra, J., Enders, G., Azizkhan, J., and Lengel, K. (2006) et al., "Dual regulation of the anaphase promoting complex in human cells by cyclin A-Cdk2 and cyclin A-Cdk1 complexes" Cell Cycle 5, 661-666.

Peters, J. M.et al., (2006). "The anaphase promoting complexfcyclosome: a machine designed to destroy." Nat Rev Mol Cell Bioi 7,644-656.

Smits, V., Klompmaker, R, Arnaud, L., Rijksen, G., Nigg, E., and Medema, Ret al., (2000)."Polo-like kinase-I is a target of the DNA damage checkpoint", Nat Cell Bioi 2, 672-676.

Sorensen, C., Lukas, C., Kramer, E., Peters, J. M., Bartek, J., and Lukas, J. et al., (2001). "A conserved cyclin-binding domain determines functional interplay between anaphasepromoting complex-Cdhl and cyclin A-Cdk2 during cell cycle progression", Mol Cell Bioi 21,3692-3703.

Sudo, T., Ota, Y., Kotani, S., Nakao, M., Takami, Y., Takeda, S., and Saya, H. et al., (2001) "Activation of Cdhl-dependent APC is required for G1 cell cycle arrest and DNA damage-induced G2 checkpoint in vertebrate cells", Embo J 20, 6499-6508.

Sullivan, M., and Morgan, D. et al., (2007). "Finishing mitosis, one step at a time", Nat Rev Mol Cell Bioi 8, 894-903.

Tsimaratou, K., Kletsas, D., Kastrinakis, N., Tsantoulis, P., Evangelou, K., Sideridou, M., Liontos, M., Poulias, I., Venere, M., Salmas, M., et al. (2007). "Evaluation of claspin as a proliferation marker in human cancer and normal tissues", J Pathol 211, 331-339.

Watanabe, N., Arai, H., Nishihara, Y, Taniguchi, M., Watanabe, N., Hunter, T., and Osada, H.et al., (2004). M-phase kinases induce phospho-dependent ubiquitination of somatic Wee1 by SCFbTrCP Proc Natl Acad Sci USA 101, 4419-4424.

Whitfield, M., Sherlock, G., Saldanha, A., Murray, J., Ball, C., Alexander, K., Matese, 1., Perou, C., Hurt, M., Brown, P., and Botstein, D. et al., (2002). Identification of genes periodically expressed in the human cell cycle and their expression in tumors. Mol Bioi Cell 13, 1977-2000.

Zhang, D., Zaugg, K., Mak, T, and Elledge, S.et al., (2006). "A role for the deubiquitinating enzyme USP28 in control of the DNA-damage response", Cell 126, 529-542.

Araki, M. Yu, H. and Asano, M. et al., (2005). A novel motif governs APC-dependent degradation of *Drosophila* ORCI in vivo, Genes Dev 19,2458-2465.

Bashir, T, Dorrello, N. V., Amador, V., Guardavaccaro, D., and Pagano, M. et al., (2004) "Control of the SCF(Skp2-Cksl) ubiquitin ligase by the APC/C(Cdhl) ubiquitin ligase" Nature 428, 190-193.

Bassermann, F., von Klitzing, C., Munch, S., Bai, R. Y, Kawaguchi, H., Morris, S. W., Peschel, C., and Duyster, J. et al., (2005). "NIPA defines an SCF-type mammalian E3 ligase that regulates mitotic entry." Cell 122, 45-57.

Brummelkamp, T. R., Bernards, R, and Agami, R. et al., (2002). "A system for stable expression of short interfering RNAs in mammalian cells" Science 296,550-553.

Carrano, A. C., Eytan, E., Hershko, A., and Pagano, M.et al., (1999). "SKP2 is required for ubiquitin-mediated degradation of the CDK inhibitor p27" Nat Cell Bioi 1,193-199.

Carrano, A. C., and Pagano, M.et al., (2001). "Role of the F-box protein Skp2 in adhesiondependent cell cycle progression" JCell Bioi 153, 1381-1390.

Chen, X., Cheung, S. T, So, S., Fan, S. T., Barry, C., Higgins, J., Lai, K. M., Ji, J.,Dudoit, S., Ng, J. 0., et al. (2002). "Gene expression patterns in human liver cancers" Mol Bioi Cell 13, 1929-1939.

Faha, B., Harlow, E., and Lees, E.et al., (1993). "The adenovirus EIA-associated kinase consists of cyclin E-p33cdk2 and cyclin A-p33cdk2" J Virol 67, 2456-2465.

Fong, A., and Sun, S. C. et al., (2002). "Genetic evidence for the essential role of beta-transducin repeat-containing protein in the inducible processing of NF-kappa B2/p100" J Bioi Chem 277, 22111-22114.

Frescas, D., Guardavaccaro, D., Bassermann, F., Koyama-Nasu, R, and Pagano, M.et al., (2007). "JHDM1 B/FBXL 10 is a nucleolar protein that represses transcription of ribosomal RNA genes", Nature 450,309-313.

Guardavaccaro, D., Frescas, D., Dorello, N., Peschiaroli, A., Multani, A., Cardozo, T., Lasorella, A, Iavarone, A., Chang, S., Hernando, E., Pagano, M. et al., (2008). "Control of chromosome stability by the TRCP-REST-MAD2 axis", Nature 452, 365-369.

Guardavaccaro, D., Kudo, Y, Boulaire, J., Barchi, M., Busino, L., Donzelli, M., Margottin-Goguet, F., Jackson, P. K., Yamasaki, L., and Pagano, M.et al., (2003). Control of Meiotic and Mitotic Progression by the F Box Protein beta-Trcp1, In Vivo. DevCel14, 799-812.

Heffernan, T P., Simpson, D. A., Frank, A. R, Heinloth, A. N., Paules, R. S., CordeiroStone, M., and Kaufmann, W. K. et al., (2002). "An ATR- and Chkl-dependent S checkpoint inhibits replicon initiation following UVC-induced DNA damage." Mol Cell Bioi 22, 8552-8561.

Hendrix, N. D., Wu, R, Kuick, R., Schwartz, D. R., Fearon, E. R., and Cho, K. Ret al., (2006)."Fibroblast growth factor 9 has oncogenic activity and is a downstream target of Wnt signaling in ovarian endometrioid adenocarcinomas." Cancer Res 66, 1354-1362.

Ke, P. Y., and Chang, Z. F.et al., (2004). "Mitotic degradation of human thymidine kinase 1 is dependent on the anaphase-promoting complexfcyc1 osome-CDHI-mediated pathway" Mol Cell Bioi 24, 514-526.

Littlepage, L. E., and Ruderman, 1. V. et al., (2002). "Identification of a new APC/C recognition domain, the A box, which is required for the Cdhl-dependent destruction of the kinase Aurora-A during mitotic exit." Genes Dev 16, 2274-2285.

Peschiaroli, A., Dorrello, N. V., Guardavaccaro, D., Venere, M., Halazonetis, T, Sherman, N. E., and Pagano, M.et al., (2006). "SCFbetaTrCP-mediated degradation of Claspin regulates recovery from the DNA replication checkpoint response" Mol Cell 23, 319-329.

Richardson, A L, Wang, Z. C., De Nicolo, A., Lu, X., Brown, M., Miron, A, Liao, x., Iglehart, J. D., Livingston, D. M., and Ganesan, S. et al., (2006)."X chromosomal abnormalities in basal-like human breast cancer." Cancer Cell 9, 121-132.

Rodier, G., Coulombe, P., Tanguay, P. L, Boutonnet, C., and Meloche, S.et al., (2008) "Phosphorylation of Skp2 regulated by CDK2 and Cdc14B protects it from degradation by APC(Cdhl) in GI phase" Embo J 27,679-691.

Rodrigo-Brenni, M. C., and Morgan, D. O. et al., (2007). "Sequential E2s drive polyubiquitin chain assembly on APC targets" Cell 130, 127-139.

Sotiriou, C., Wirapati, P., Loi, S., Harris, A, Fox, S., Smeds, J., Nordgren, H., Farmer, P., Praz, V., Haibe-Kains, B., et al. (2006). "Gene expression profiling in breast cancer: understanding the molecular basis of histologic grade to improve prognosis" J Natl Cancer Inst 98,262-272.

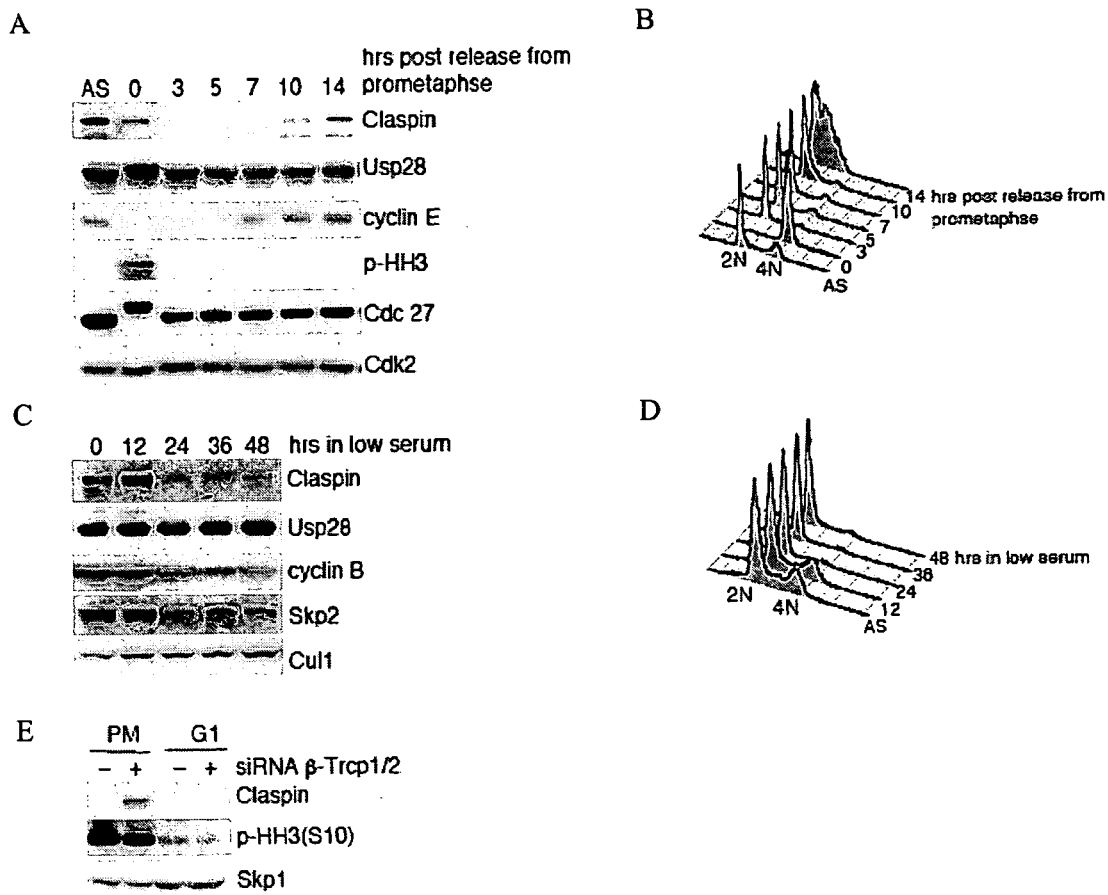
Figs. 1 A-E

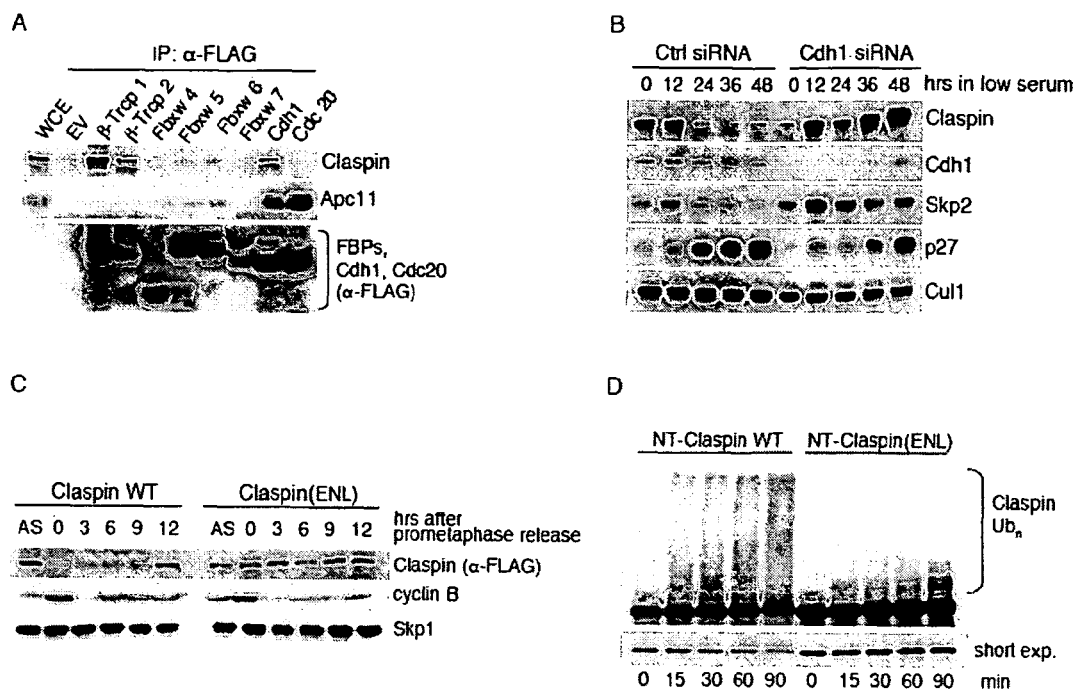
Figs. 2 A-D

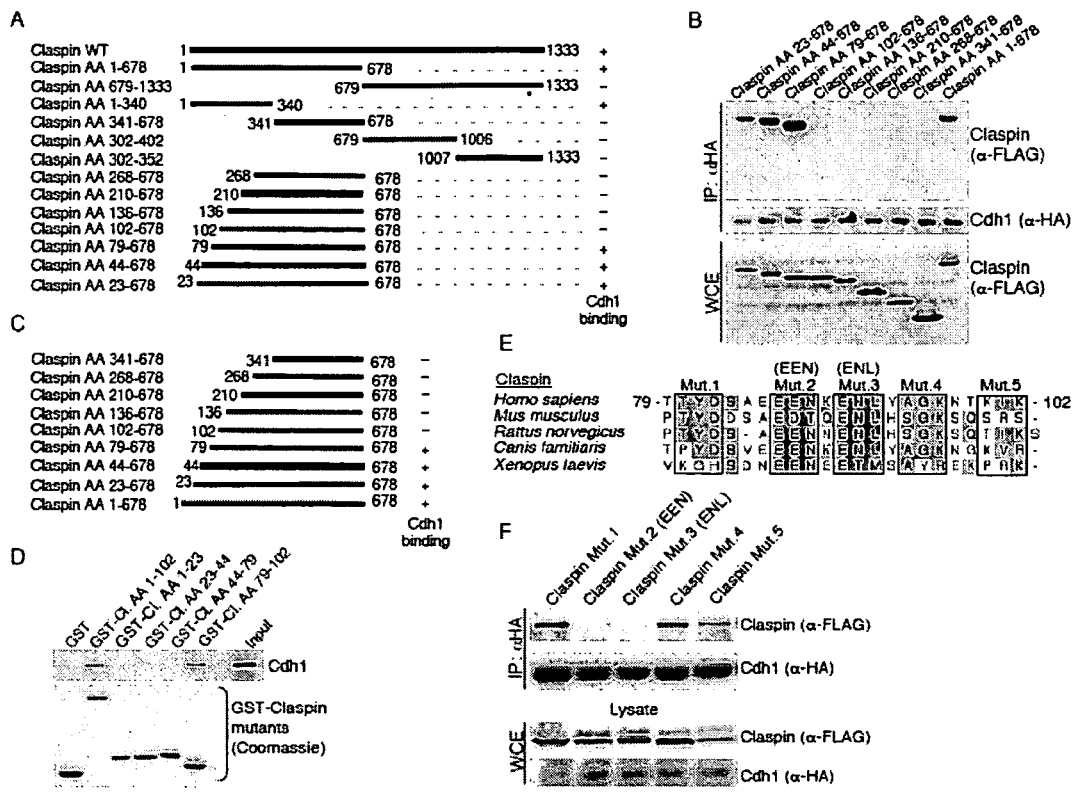
Figs. 3 A-F

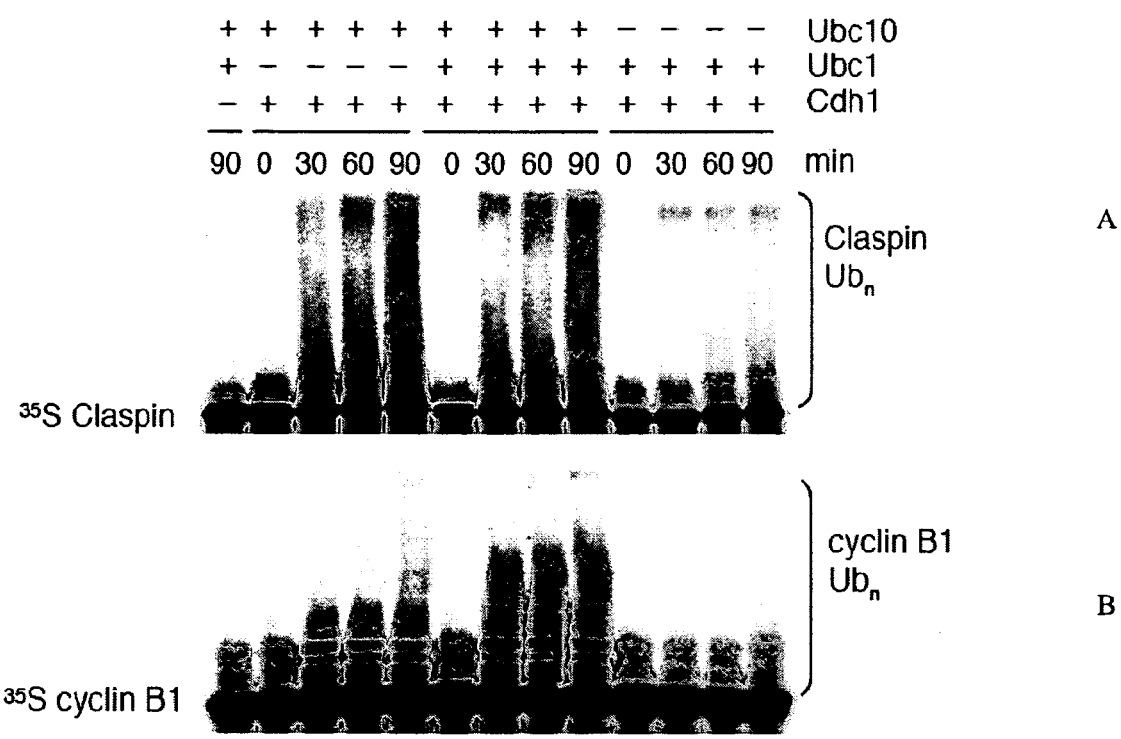
Figs. 4 A-B

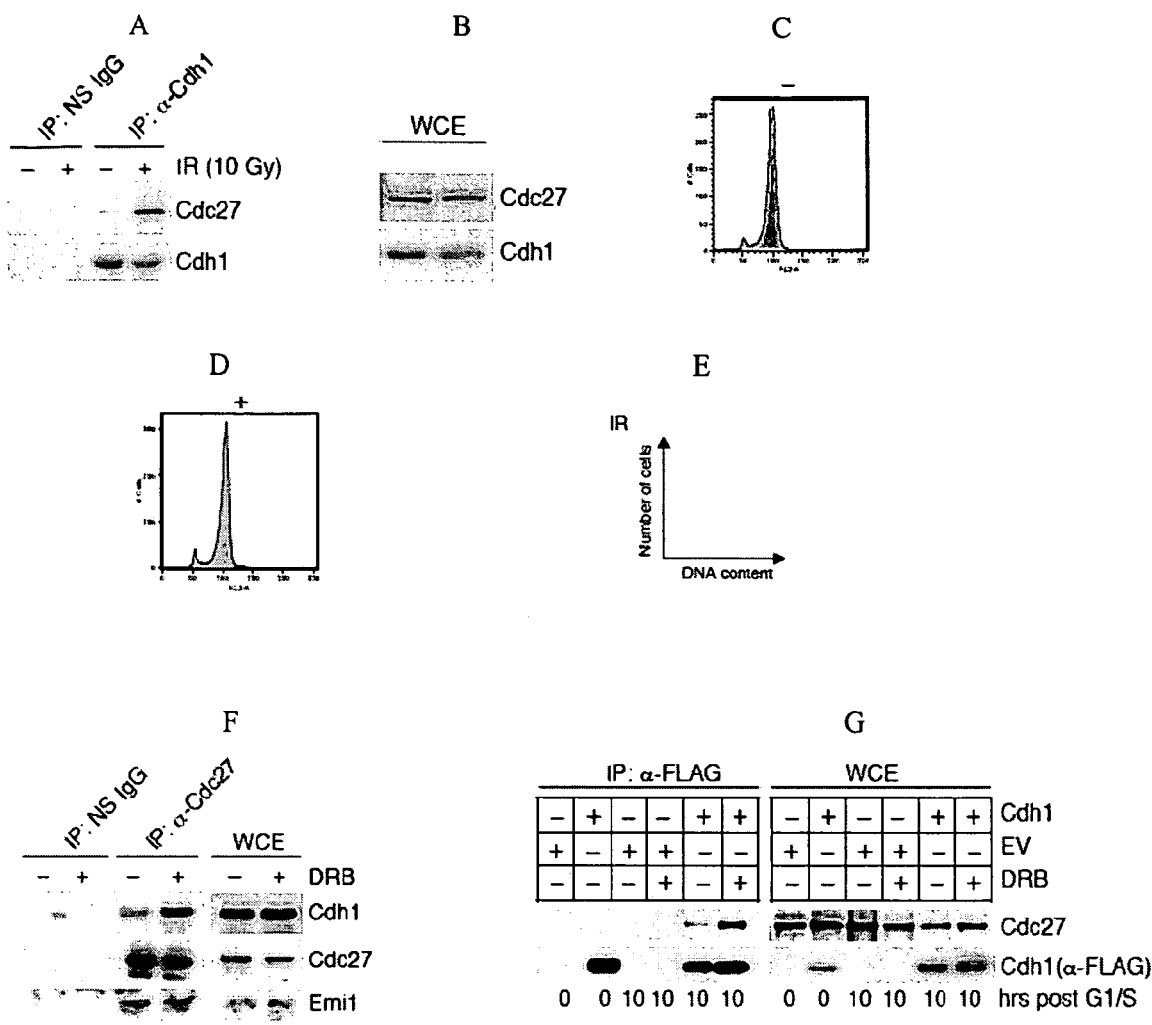
Figs. 5 A-G

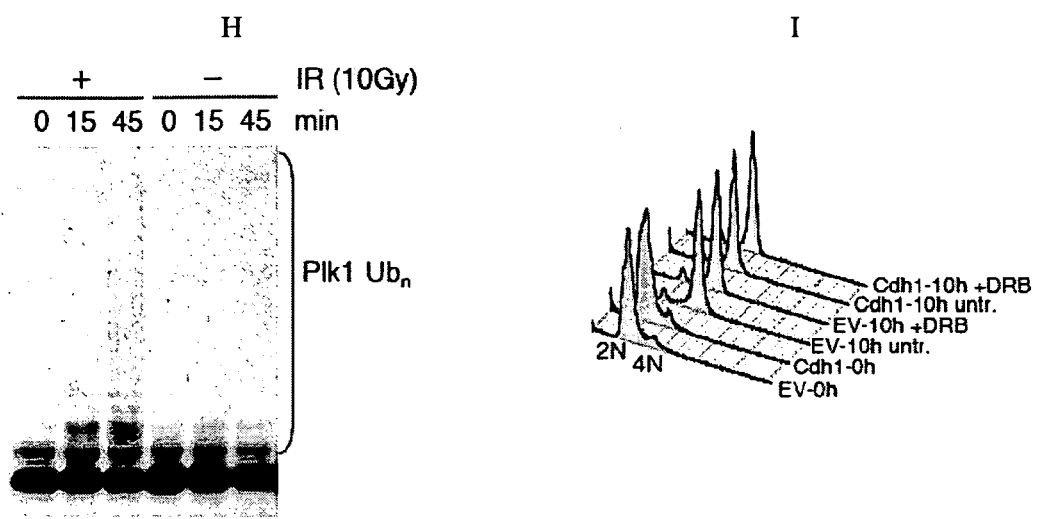
Figs. 5 H-I

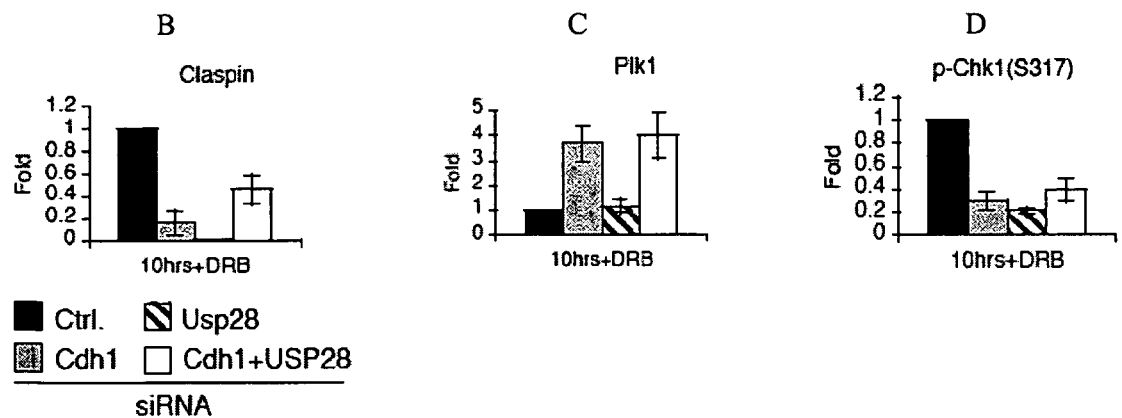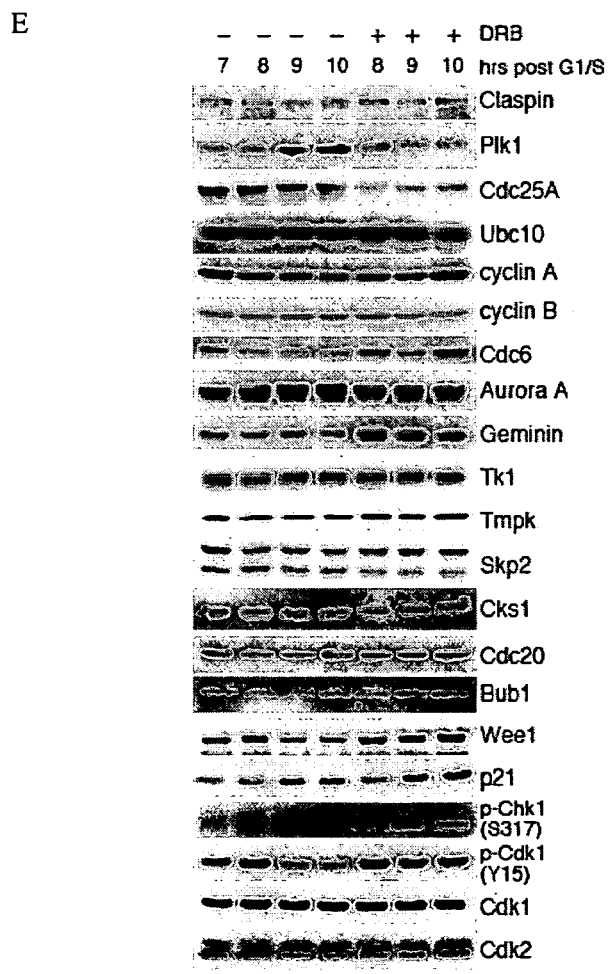
Figs. 6 B-E

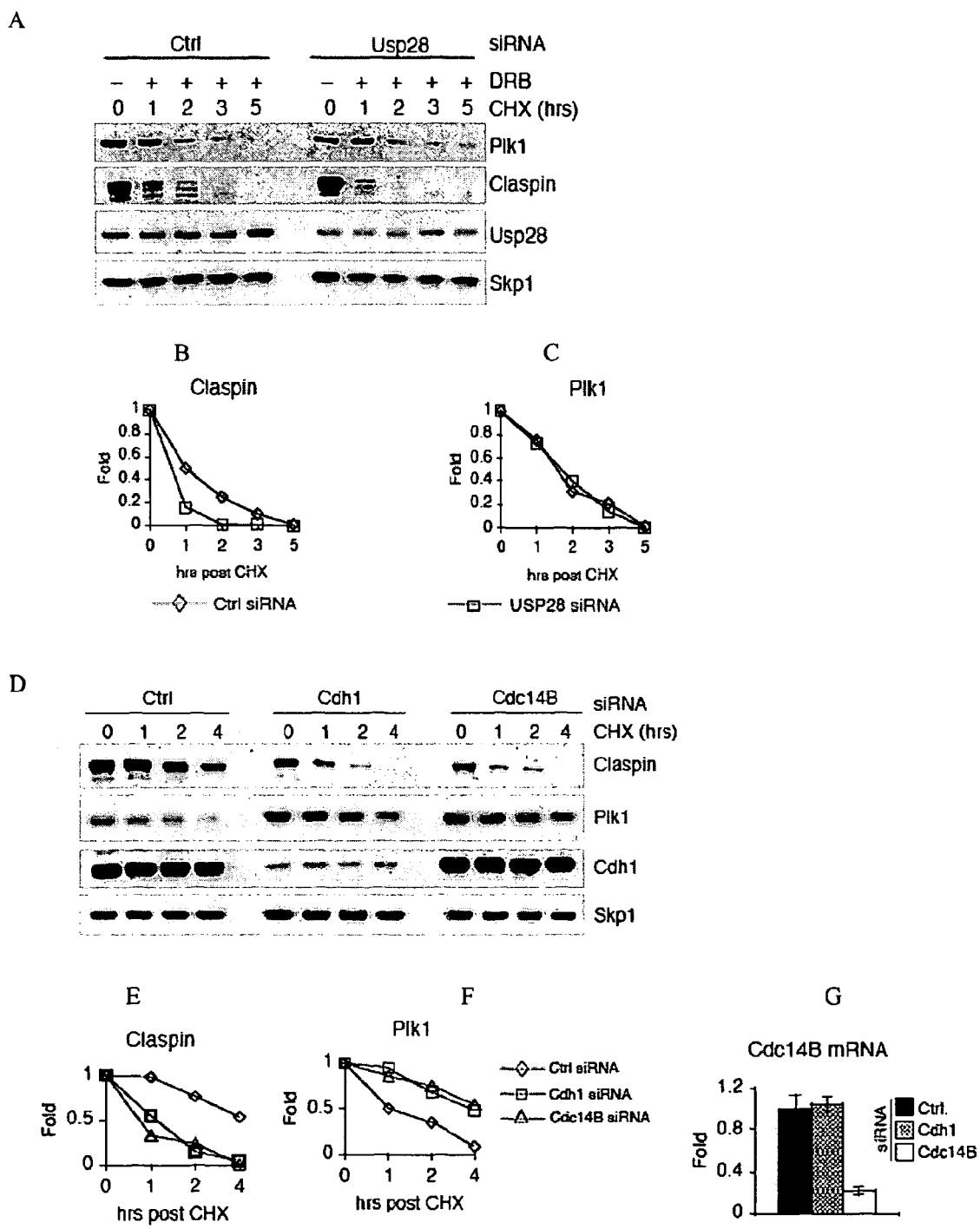
Figs. 7 A-G

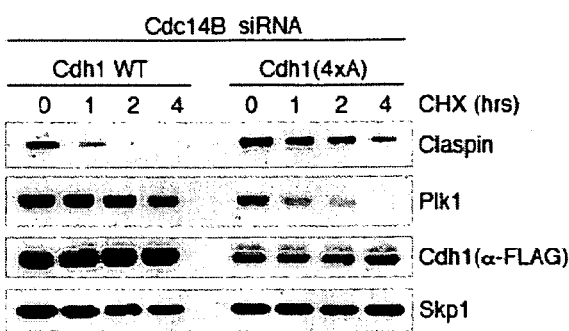
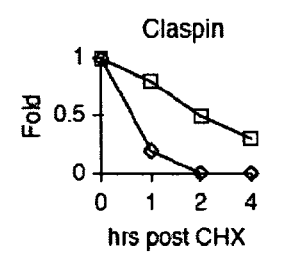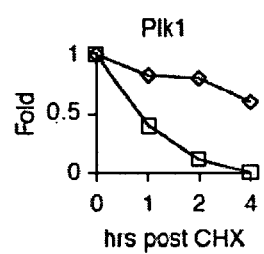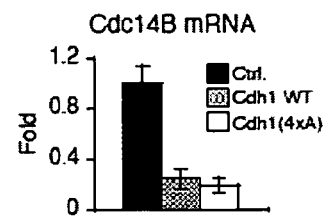
Figs. 7 H-K

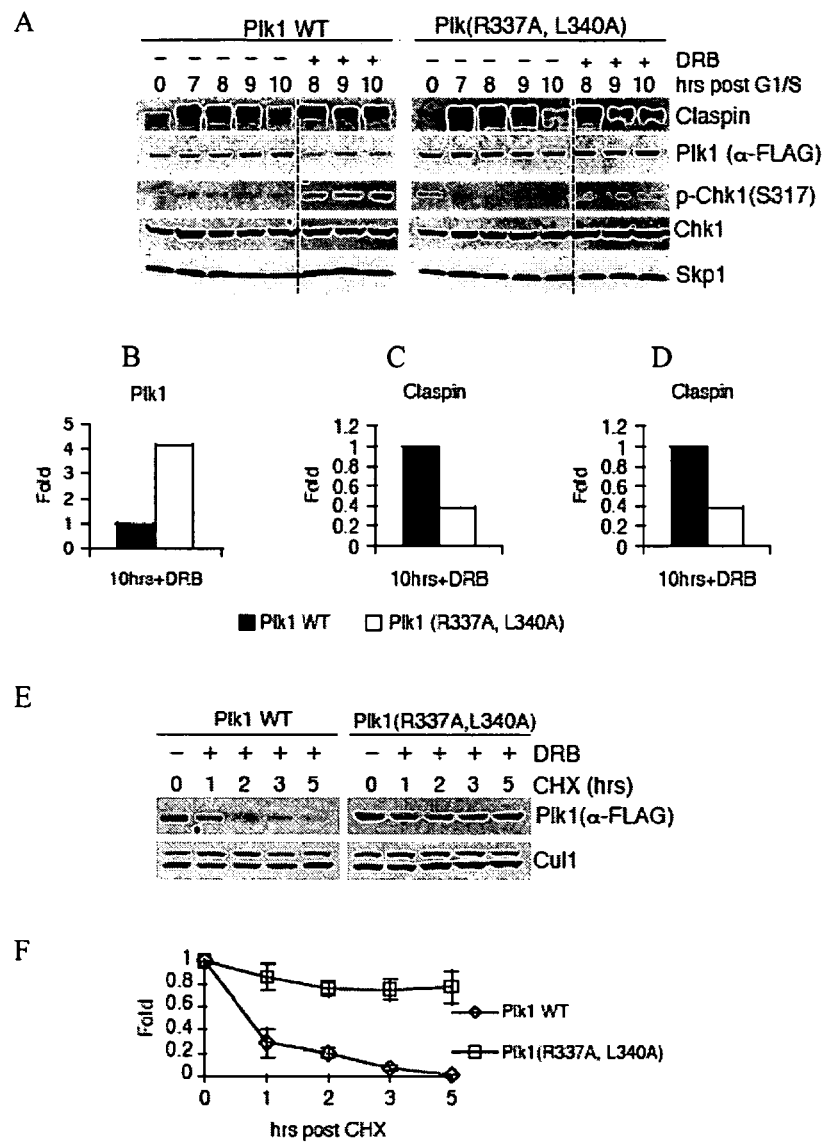
Figs. 8 A-F

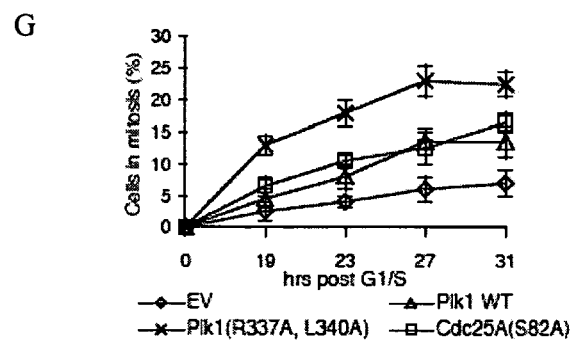
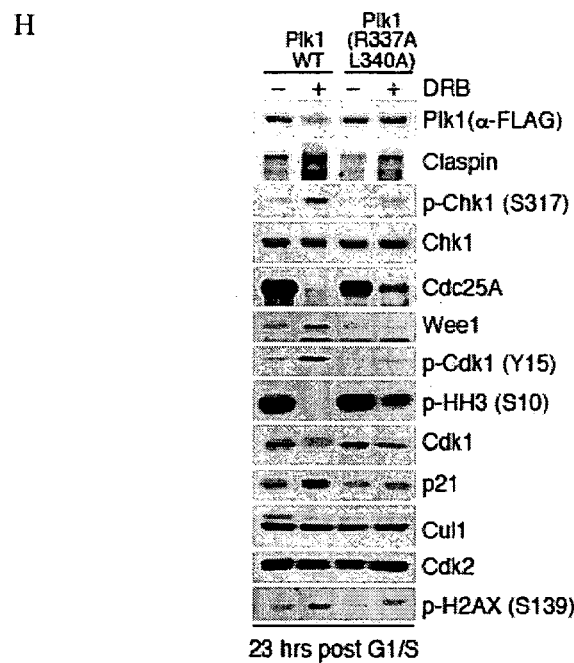
Figs. 8 G-H

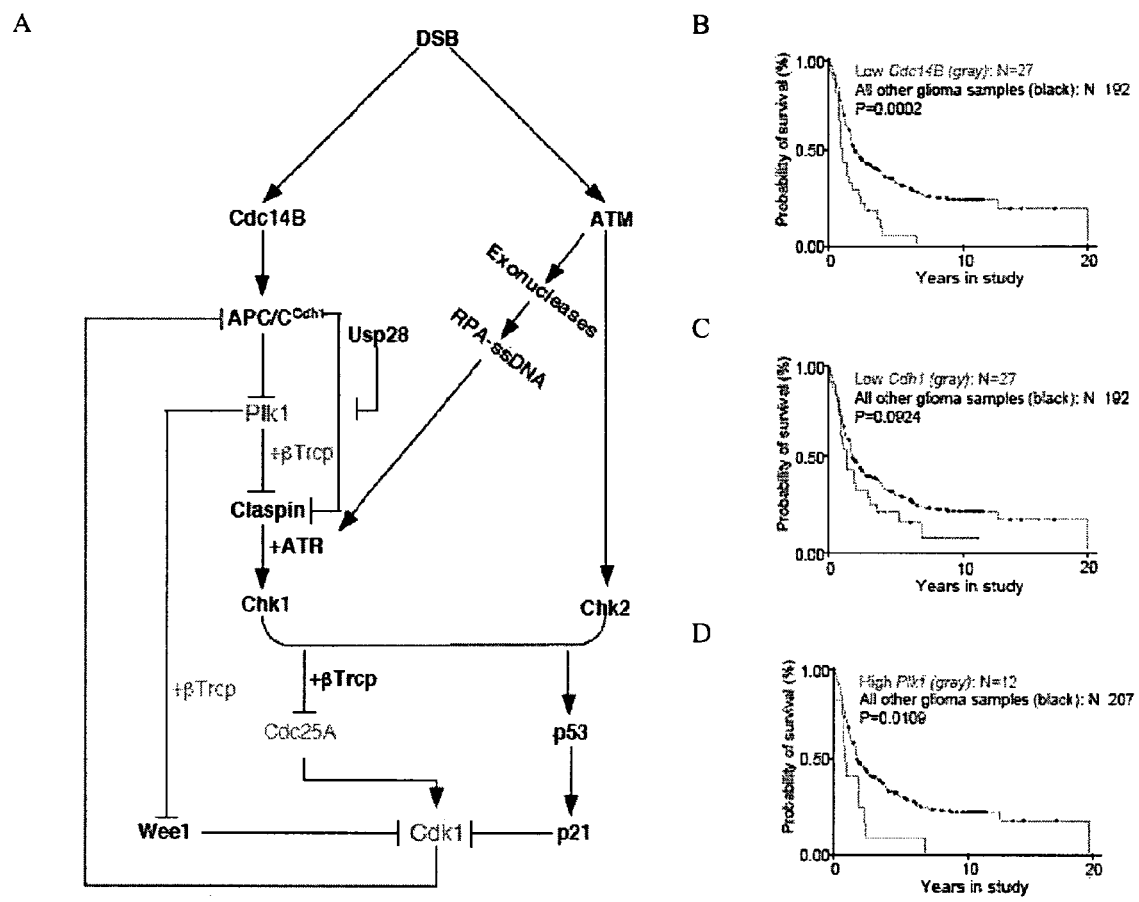
Figs. 15 A-D

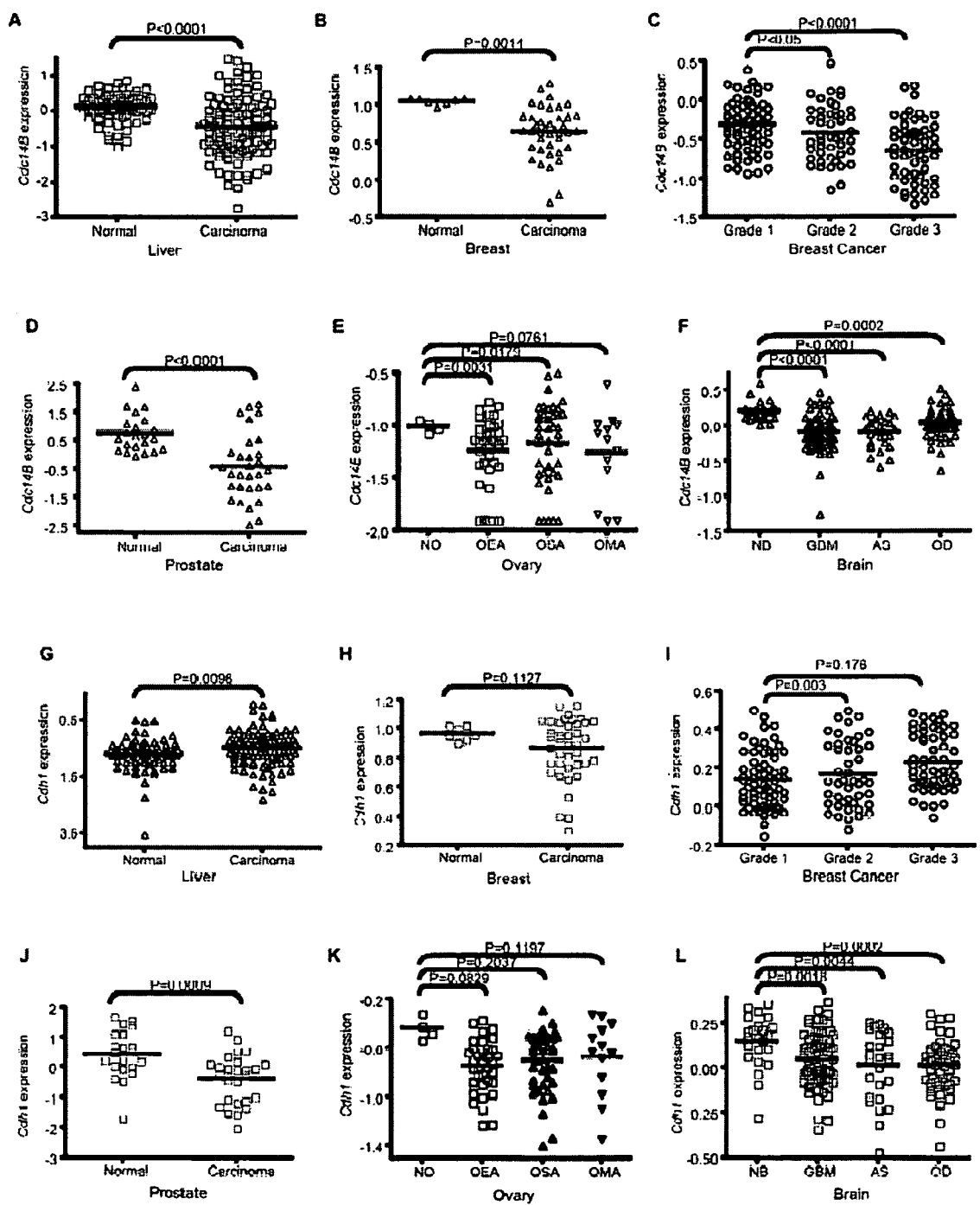
Figs. 16 A-L

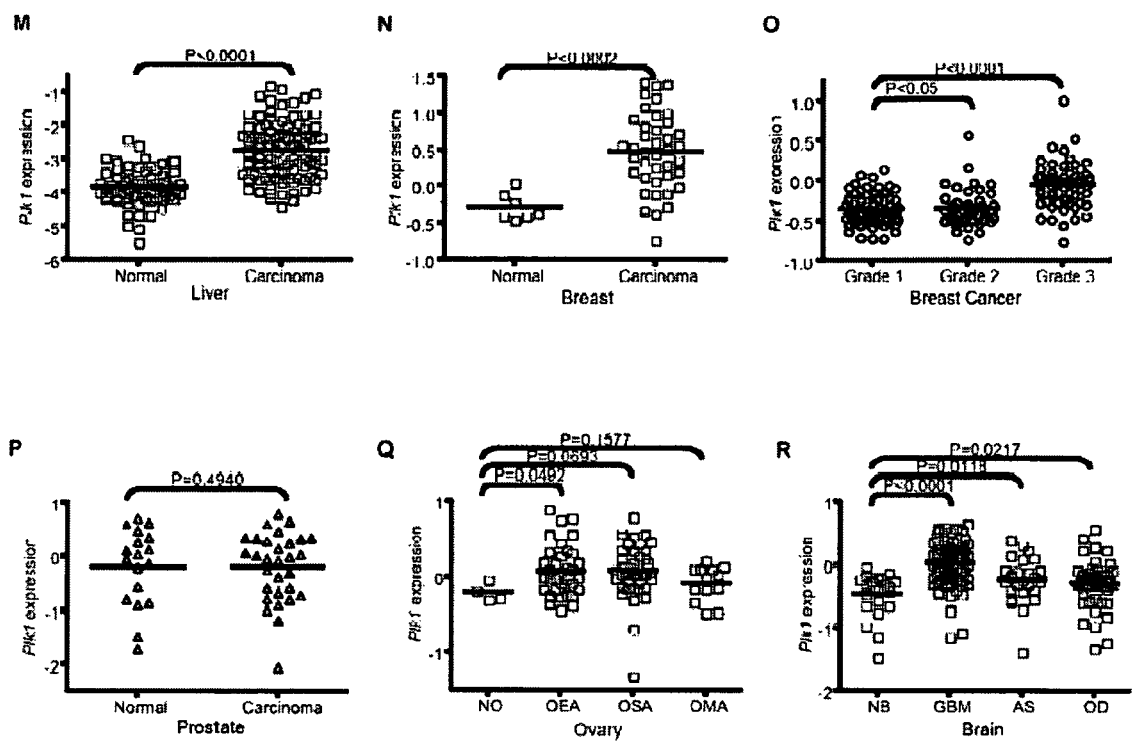
Figs. 16 M-R

MODULATING THE CDC14B-CDH1-PLK1 AXIS AND METHODS FOR SENSITIZING TARGET CELLS TO APOPTOSIS

CROSS REFERENCE TO RELATED APPLICATIONS

The present application is a divisional of U.S. patent application Ser. No. 12/499,208, filed on Jul. 8, 2009, which claims the benefit of U.S. Provisional Patent Application Ser. No. 61/081,720, filed on Jul. 17, 2008, both of which are hereby incorporated by reference in their entirety.

FEDERALLY SPONSORED RESEARCH OR DEVELOPMENT

This invention was made in part in the course of research sponsored by the National Institutes of Health (NIH) Grants R01-GM57587, R37-CA76584 and R21-CA125173. The U.S. government may have certain rights in this invention.

FIELD OF THE INVENTION

The invention relates to modulating Cdc14B levels ("cell division cycle 14 homolog B") and/or Cdh1 levels ("fizzed related" "Fzr") to sensitize cells to DNA damage by increasing the abundance of Plk1 (polo-like kinase 1) in a target cell. In certain embodiments, the invention relates to modulating Plk1 levels, and in particular to increasing Plk1 levels, to sensitize target cells such as cancer cells to cell death or apoptosis

BACKGROUND OF THE INVENTION

The Ubiquitin Pathway

Ubiquitin-mediated proteolysis is an important pathway of non-lysosomal protein degradation which controls the timed destruction of many cellular regulatory proteins including, p27, p53, p300, cyclins, E2F, STAT-1, c-Myc, c-Jun, EGF receptor, IκBα, NFκB and β-catenin (reviewed in Pagano, 1997, FASEB J. 11: 1067). Ubiquitin is an highly conserved 76-amino acid polypeptide that is abundantly present in all eukaryotic cells. The ubiquitin pathway leads to the covalent attachment of a poly-ubiquitin chain to target substrates which are then degraded by the multi-catalytic proteasome complex (see Pagano, supra, for a recent review). Many of the steps regulating protein ubiquitination are known. Initially the ubiquitin activating enzyme (E1), forms a high energy thioester with ubiquitin which is, in turn, transferred to a reactive cysteine residue of one of many ubiquitin conjugating enzymes (Ubcs or E2s). The final transfer of ubiquitin to an e-amino group of a reactive lysine residue in the target protein occurs in a reaction that may or may not require an ubiquitin ligase (E3) protein. The large number of ubiquitin ligases ensures a high level of substrate specificity.

The Ubiquitin Pathway and the Regulation of the G1 Phase by F Box Proteins

Genetic and biochemical studies in several organisms have shown that the G1 phase of the cell cycle is regulated by the ubiquitin pathway. Proteolysis of cyclins, Ckis and other G1 regulatory proteins is controlled in yeast by the ubiquitin conjugating enzyme Ubc3 (also called Cdc34) and by an E3 ubiquitin ligase formed by three subunits: Cdc53, Skp1 and one of many F box proteins (reviewed in Patton, et al., 1998, Trends in Genet. 14:6). The F box proteins (FBPs) are so called because they contain a motif, the F Box, that was first identified in Cyclin F, and that is necessary for FBP interaction with Skp1 (Bai, et al., 1996, Cell 86:263). Cdc53 (also called Cul A) and Skp1 appear to participate in the formation of at least three distinct E3s, each containing a different FBP. Because these ligases are similar protein modules composed of Skp1, Cul A, and an FBP, they have been named SCF. The three SCFs identified in *S. cerevisiae* are: $SCF^{Cdc4}$ (which recruits the Ckis Sic1 and Far1, the replication factor Cdc6, and the transcriptional activator Gcn4, as substrates through the F-Box protein Cdc4), $SCF^{Grr1}$ (which recruits the G1 cyclins Cln1 and Cln2 as substrates through the F-Box protein GRR1), and $SCF^{Met30}$ (which recruits the G1 cyclin Cln3 as a substrate throughout the F box protein MET30; see Pagano and Patton, supra, for recent reviews).

The interaction of SCF ligase with its substrates occurs via the FBP. FBPs are present in all eukaryotes (at least 54 in mammals; Cenciarelli, et al., 1999, Current Biol. 9: 1177; Winston, et al., 1999, Current Biol. 9: 1180). In addition to the F Box, many FBPs contain additional domains that facilitate both protein:protein interactions, e.g. WD-40 domains or leucine-rich repeats (LRRs), and protein:DNA interactions, e.g. tankyrase binding domains or HNH domains. Since the substrate specificity of SCF ligases is dictated by different FBPs that act as substrate targeting subunits, the large numbers of FBPs with varying combinations of protein or DNA interaction domains ensure highly specific substrate recognition.

FBP1, A Mammalian FBP Involved in Regulation of APC/C

Fbp1, the mammalian homolog of *Xenopus* β-TrCP1 (β-transducin repeat containing protein) (Spevak, et al., 1993, Mol. Cell. Biol. 8:4953), was identified using Skp1 as a bait in a two-hybrid screen (Cenciarelli, et al., supra). Fbp1 is an F box protein containing seven WD-40 domains (Margottin, et al., 1998, Mol. Cell 1:565), and is involved in the degradation of IκBα family members in response to NFκB activating stimuli (Gonen, et al., 1999, J. Biol. Chem. 274:14823; Hatakeyama, et al., 1999, Proc. Natl. Acad. Sci. USA 96:3859; Hattori, et al., 1999, J. Biol. Chem. 274:29641; Kroll, et al., 1999, J. Biol. Chem. 274:7941; Ohta, et al., 1999, Mol. Cell 3:535; Shirane, et al., 1999, J. Biol. Chem. 274: 28169; Spencer, et al., 1999, Genes Dev. 13:284; Winston, et al., 1999, Genes Dev. 13:270; Wu and Ghosh, 1999, J. Biol. Chem. 274:29591; Yaron, et al., 1998, Nature 396:590). In addition, consistent with the finding that *Xenopus* and *Drosophila* Fbp1 orthologs act as negative regulators of the Wnt/β-catenin signaling pathway (Jiang and Struhl, 1998, Nature 391:493; Marikawa and Elinson, 1998, Mech. Dev. 77:75), several studies report that human Fbp1 controls β-catenin stability in vitro and in mammalian cultured cells (Hart, et al., 1999, Curr. Biol. 9:207; Hatakeyama, et al., supra; Kitagawa, et al., 1999, EMBO J. 18:2401; Latres, et al., 1999, Oncogene 18:849; Winston, et al., 1999, Genes Dev. 13:270).

Well-characterized substrates of mammalian Fbp1 have been found to share a common destruction motif, DSGxxS, and are recognized by Fbp1 only upon phosphorylation of the two serine residues present in this motif. There is, however, some recent evidence for additional mammalian substrates of Fbp1 lacking a completely conserved binding domain, such as ATF4 (Lassot, et al., 2001, Mol. Cell. Biol. 21:2192), Smad3 (Fukuchi, et al., 2001, Mol. Biol. Cell 12:1431), NFκB p105 (Orian, et al., 2000, EMBO J. 19:2580) and NFκB p100 (Fong and Sun, 2002, J. Biol. Chem. 277:22111). A conserved DSGxxS motif is present not only in Fbp1 substrates but also in certain regulators of Fbp1, such as the HIV protein Vpu, which targets Fbp1 to the non-physiological substrate, CD4, in virally infected cells. (Margottin, et al., supra). The DSGxxS destruction motif may also be found in peptide regulators of Fbp1 termed pseudosubstrates; however, pseudosubstrates escape the normal degradation fate of other FBP target proteins and instead modulate the activity of the FBP, and corresponding Cks, such as cellular localization and substrate targeting. For example, the Fbp1 pseudosubstrate hnRNP-U not only inhibits Fpb1 from targeting inappropriate substrates but also serves to localize Fbp1 to the nucleus (Davis, et al., 2002, Genes Dev. 16:439).

A further level of complexity is added by the presence of a Fbp1/β-TrCP1 (beta-transducin repeat containing protein 1) paralogous gene product, called β-TrCP2 (beta-transducin repeat containing protein 2) or Fbxw1B (78% identical, 86% similar to β-TrCP1; Kipreos and Pagano, 2000, Genome Biology 1:3002.1). Fbp1 and β-TrCP2 are ubiquitously expressed in adult human tissues (Cenciarelli, et al., supra; Koike, et al., 2000, Biochem. Biophys. Res. Commun. 269: 103). In addition, β-TrCP2 has biochemical properties similar to Fbp1 in its ability to sustain the ubiquitinylation of both β-catenin and IKBα family members in vitro and to control their degradation in mammalian cultured cells (Fuchs, et al., 1999, Oncogene 18:2039; Suzuki, et al., 1999, Biochem. Biophys. Res. Commun. 256:127; Tan, et al., 1999, Mol. Cell 3:527). Despite these similarities, Fbp1 localizes to the nucleus and β-TrCP2 localizes mainly to the cytoplasm (Davis, et al., 2002, Genes Dev. 16:439). It is not clear whether these two FBPs have overlapping functions in vivo, or if each of them recognizes specific substrates.

Deregulation of the Ubiquitin Pathway in Cancer and Other Proliferative Disorders Cancer develops when cells multiply too quickly. Cell proliferation is determined by the net balance of positive and negative signals. When positive signals overcome or when negative signals are absent, the cells multiply too quickly and cancer develops.

Ordinarily cells precisely control the amount of any given protein and eliminate the excess or any unwanted protein. To do so, the cell ubiquitinates the undesired protein to tag the protein for proteasome degradation. This mechanism goes awry in tumors, leading to the excessive accumulation of positive signals (oncogenic proteins), or resulting in the abnormal degradation of negative regulators (tumor suppressor proteins). Thus, without tumor suppressor proteins or in the presence of too much of an oncogenic protein, cells multiply without control, forming tumors (reviewed by Ciechanover, 1998, EMBO J. 17: 7151; Spataro, 1998, Br. J. Cancer 77: 448). For example, abnormal ubiquitin-mediated degradation of the p53 tumor suppressor (reviewed by Brown and Pagano, 1997, Biochim. Biophys. Acta 1332:1), the putative oncogene β-catenin (reviewed by Peifer, 1997, Science 275: 1752) and the Cki p27 (reviewed in Ciechanover, supra; Spataro, supra; Lloyd, 1999, Am. J. Pathol. 154: 313) have been correlated with tumorigenesis, opening to the hypothesis that some genes encoding ubiquitinating enzymes may be mutated in tumors.

Initial evidence indicates that human F box proteins play a role in the ubiquitination of G1 regulatory proteins as do their homologues in yeast. Unchecked degradation of cell cycle regulatory proteins has been observed in certain tumors and it is possible that deregulated ubiquitin ligase plays a role in the altered degradation of cell cycle regulators. A well understood example is that of Mdm2, a ubiquitin ligase whose overexpression induces low levels of its substrate, the tumor suppressor p53.

Alternately, F box proteins have been shown to interact directly with DNA regulating proteins or DNA itself. F box proteins in yeast are known to regulate genomic stability and senescence, and recent data has shown that F box inhibition in mammalian cells can lead to the loss of DNA damage checkpoints.

DNA Damage and the Cell Cycle

The Anaphase Promoting Complex or Cyclosome (APC/C) is a ubiquitin ligase that plays a crucial role in the regulation of mitosis and the G1 phase of the cell cycle (Peters, 2006). In early mitosis, APC/C is activated through binding to Cdc20, and in late M, Cdc20 is replaced by Cdh1, the second activator of APC/C. During G1, APC/C$^{Cdh1}$ remains active to ensure that certain positive regulators of the cell cycle do not accumulate prematurely. Then, at the G1/S transition, APC/C$^{Cdh1}$ is inactivated by phosphorylation to allow stabilization of its substrates and promote progression into S phase. Cdk1-cyclin A and Cdk2-cyclin A mediate the phosphorylation of Cdh1, resulting in the dissociation of Cdh1 from the APC/C core (Lukas et al., 1999; Mitra et al., 2006; Sorensen et al., 2001). Other mechanisms inhibiting APC/C$^{Cdh1}$ activity include Emi1 binding and degradation of both Cdh1 and Ubc10 (a ubiquitin conjugating enzyme that works with APC/C). During G2, both Cdh1 and Ubc10 reaccumulate, but APC/C$^{Cdh1}$ remains inactive due to CDK-dependent phosphorylation of Cdh1 and the presence of Emi1. In early mitosis, Emi1 is eliminated via the SCF$^{\beta Trcp}$ ubiquitin ligase, but the bulk of APC/C$^{Cdh1}$ remains inactive due to high Cdk1 activity. Ultimately, Cdh1 activation in anaphase involves Cdk1 inactivation by APC/C$^{Cdc20}$ and Cdh1 dephosphorylation. In yeast, this dephosphorylation is carried out by the Cdc14 phosphatase, but the mechanism in mammals remains unclear (D'Amours and Amon, 2004; Sullivan and Morgan, 2007).

Upon DNA damage, proliferating cells activate a regulatory signaling network to either arrest the cell cycle and enable DNA repair or, if the DNA damage is too extensive to be repaired, induce apoptosis (Bartek and Lukas, 2007; Harper and Elledge, 2007; Kastan and Bartek, 2004). The DNA damage response involves a number of factors that ultimately coordinate the spatiotemporal assembly of protein complexes at the site of DNA damage to initiate and maintain the checkpoint. Depending on the type of genotoxic stress, different checkpoint pathways are activated. UV and stalled replication forks activate the ATR-Chk1 pathway, whereas double-strand breaks result in the activation of both the ATM-Chk2 and the ATR-Chk1 pathways. After ATR is recruited to the site of damage, it phosphorylates and activates the effector kinase Chk1, a process requiring the mediator protein Claspin. Important downstream targets of Chk1 include p53 and Cdc25A, a transcription factor and an activator of Cdk1, respectively. Chk1-mediated phosphorylation induces the stabilization of p53 (with the consequent expression of the CDK inhibitor p21) and is required for the SCF$^{\beta Trcp}$-mediated degradation of Cdc25A; thus, Chk1 activation results in the attenuation of Cdk1 activity, with the consequent inhibition of mitosis.

During the recovery from DNA replication and DNA damage stresses, the G2 checkpoint must be silenced. This process involves the degradation of Claspin via the SCF$^{\beta Trcp}$ ubiquitin ligase following the phosphorylation of Claspin by Plk1 (Mailand et al., 2006; Mamely et al., 2006; Peschiaroli et al., 2006). However, if DNA damage occurs during G2, SCF$^{\beta Trcp}$-dependent ubiquitylation of Claspin is inhibited to re-establish the checkpoint. The blocking of Claspin ubiquitylation is at least partially due to the inhibition of Plk1, which occurs in response to DNA damage (Smits et al., 2000). In fact, Claspin is not phosphorylated on its degron and does not bind βTrcp in G2 cells that have been subjected to DNA damage (Peschiaroli et al., 2006). However, despite the lack of SCF$^{\beta Trcp}$-Plk1-dependent ubiquitylation, Claspin continues to be ubiquitylated, only remaining stable due to a deubiquitylating enzyme (DUB), namely Usp28 (Zhang et al., 2006).

There is a general need for treatments relating to regulating or affecting the cell cycle to sensitize target cells, such as tumor or cancer cells, to cell death or apoptosis. In particular, there is a need for small molecule inhibitors that are useful as therapeutic agents, as well as for diagnostic and screening tools for identifying test therapeutic candidates.

SUMMARY OF THE INVENTION

The present invention provides a method of sensitizing a cell to cell death or apoptosis comprising contacting a target cell with an effective amount of an inhibitor of Cdc14B and/or Cdh1. In certain embodiments, the inhibitor results in an increase in the amount of protein compared to the amount of Plk1 protein prior to use of an effective amount of the inhibitor.

In certain embodiments, the invention relates to a method of sensitizing a cell to apoptosis or cell death comprising contacting the cell with an effective amount of an inhibitor of Cdc14B and/or Cdh1. In certain embodiments, the level of Plk1 protein (polo-like kinase 1, also known as Plk, STPK13, or polo-like kinase homolog) in the cell is increased compared to the amount of Plk1 in the cell prior to use of the inhibitor.

In certain embodiments, the cell is a diseased or abnormal cell from tissue or a cell line that exhibits a disease or abnormal condition selected from the group consisting of cancer, infection, immune disorder, cardiovascular disease, and inflammatory disorders.

In yet additional embodiments, the method further comprises contacting the cell with a second agent for sensitizing the cell to DNA damage, or for inducing apoptosis or cell death of a target cell.

In yet additional embodiments, the invention relates to a method of killing a cell comprising contacting the cell with an amount of an inhibitor of Cdc14B and/or Cdh1 that is effective to sensitize the cell to apoptosis or cell death.

In certain embodiments, the level of Plk1 protein (polo-like kinase 1, also known as Plk, STPK13, or polo-like kinase homolog) in the cell is increased compared to the amount of Plk1 in the cell prior to use of the inhibitor.

In yet additional embodiments, the method further comprises contacting the cell with a second agent for sensitizing the cell to DNA damage, or for inducing apoptosis or cell death of a target cell.

In further embodiments, the invention relates to a method of screening for an agent for sensitizing a target cell to apoptosis or cell death comprising: i) contacting a cell expressing Cdc14B and/or Cdh1 with a test compound; and ii) comparing the degradation rate of the Cdc14B and/or Cdh1 to a control, wherein the control is the degradation rate of Cdc14B and/or Cdh1 in the absence of the test compound; and iii) selecting a test compound that increases the degradation rate Cdc14B and/or Cdh1 as a compound for sensitizing a target cell to apoptosis or cell death.

In further embodiments, the invention relates to a method of screening for an agent for sensitizing a cancer cell to apoptosis or cell death: i) contacting a cell expressing Cdc14B and/or Cdh1 with a test compound; ii) comparing the amount of Cdc14B and/or Cdh1 present in the cell in the presence and in the absence of the test compound; and iii) selecting a test compound that decreases the amount of Cdc14B and/or Cdh1 in the cell as an agent for sensitizing a cancer cell to apoptosis or cell death.

In yet additional embodiments, the target cell is a diseased or abnormal cell from tissue or a cell line that exhibits a disease or an abnormal condition selected from the group consisting of cancer, infection, immune disorder, cardiovascular disease, and inflammatory disorders.

In further embodiments, the test compound is an siRNA. In certain embodiments, the siRNA comprises SEQ ID NO:20, SEQ ID NO:21, or a combination of both SEQ ID NO:20 and SEQ ID NO:21.

In yet additional embodiments, the Cdc14B or Cdh1 comprises the sequence of SEQ ID NO:15 or SEQ ID NO:10.

In further embodiments, the invention relates to a method of treating cancer in a mammalian subject which comprises: administering an effective amount of at least one Cdc14B or Cdh1 inhibitor to a mammalian subject suffering from cancer, wherein the inhibitor sensitizes cancer cells to chemotherapy.

In certain embodiments, the Cdc14B and/or Cdh1 inhibitor results in an increase in the amount of Plk1 protein (polo-like kinase 1, also known as Plk, STPK13, or polo-like kinase homolog) in a cell when compared to the amount of Plk1 protein in said cell prior to administering the inhibitor.

In yet additional embodiments, the invention relates to a kit for screening for an agent useful for modulating Plk1 protein (polo-like kinase 1, also known as Plk, STPK13, or polo-like kinase homolog) activity comprising: a Plk1 protein, at least one Plk1 binding protein selected from the group of Cdc14B ("cell division cycle 14 homolog B" also called "dual specificity protein phosphatase $CDCl_4B$") and Cdh1 protein ("fizzed related", "Fzr"), a means for detecting binding between the Plk1 and the Cdc14B and/or Cdh1 protein, and optionally instructions for use.

In further embodiments, the invention relates to a kit for screening for an agent useful for sensitizing a cell to apoptosis or cell death: a Plk1 protein (polo-like kinase 1, also known as Plk, STPK13, or polo-like kinase homolog) at least one Plk1 binding protein selected from the group of Cdc14B ("cell division cycle 14 homolog B" also called "dual specificity protein phosphatase CDC14B") and Cdh1 protein ("fizzed related", "Fzr"), a means for detecting binding between the Plk1 protein and the Cdc14B and/or Cdh1 protein, and optionally instructions for use.

In yet additional embodiments, the invention relates to a method for sensitizing a cell to apoptosis or cell death in a target cell of a mammal in need thereof, which comprises contacting said target cell with an effective amount of an inhibitor of Cdc14B and/or Cdh1.

In certain embodiments, the cell is a diseased or abnormal cell from a mammal that exhibits a disease or abnormal condition selected from the group consisting of cancer, infection, immune disorder, cardiovascular disease, and inflammatory disorders.

In yet additional embodiments, the method further comprises contacting the cell with a second agent for sensitizing the cell to DNA damage, or for inducing apoptosis or cell death of a target cell. In certain embodiments the mammal is a human.

In additional embodiments, the inhibitor of Cdc14B and/or Cdh1 comprises SEQ ID NO:20, SEQ ID NO:21, or a combination of both SEQ ID NO:20 and SEQ ID NO:21.

In yet further embodiments, the invention relates to a method of screening for an agent for sensitizing a target cell to apoptosis or cell death comprising: i) measuring the level of Cdc14B ("cell division cycle 14 homolog B" also called "dual specificity protein phosphatase CDC14B") and/or Cdh1 levels ("fizzed related" "Fzr") expressed by a target cell, ii) contacting the target cell that expresses Cdc14B and/or Cdh1 with a test compound, iii) measuring the amount of Cdc14B and/or Cdh1 expressed by the cell after said contacting step, iv) comparing the level of Cdc14B and/or Cdh1 expression in said cell before and after said contacting step, and v) selecting as a therapeutic agent candidate a test compound that decreases the level of Cdc14B and/or Cdh1 by said target cell.

In yet additional embodiments, the invention relates to a method of screening for an agent for sensitizing a target cell to apoptosis or cell death comprising: i) measuring the level of Plk1 (polo-like kinase 1, also known as Plk, STPK13, or polo-like kinase homolog) protein expressed by a target cell, ii) contacting the target cell that expresses Plk1 protein with a test compound, iii) measuring the amount of Plk1 protein expressed by the cell after said contacting step, iv) comparing the level of Plk1 expression in said cell before and after said contacting step, and v) selecting as a therapeutic agent candidate a test compound that increases the level of Plk1 protein by said target cell.

BRIEF DESCRIPTION OF THE DRAWINGS

FIGS. 1A-E are immunoblots and corresponding cell cycle profiles showing $SCF^{\beta Trcp}$-independent degradation of Claspin in G1.

FIGS. 2A-D are immunoblots showing Claspin is degraded in G0 and G1 via the APC/$C^{Cdh1}$ ubiquitin ligase.

FIGS. 3A-F show mapping of the Cdh1-binding motif in Claspin.

FIGS. 4A-B show that the N-terminus of Claspin is ubiquitylated in a Cdh1-dependent manner.

FIGS. 5A-I show reassociation and reactivation of APC/$C^{Cdh1}$ upon exposure to genotoxic stress in G2.

FIGS. 6A-E are immunoblots and graphs showing that in response to DNA damage in G2, APC/$C^{Cdh1}$ is reactivated to target Plk1 and Claspin, which is protected by Usp28.

FIGS. 7A-K show half-life analyses of Plk1 and Claspin under different conditions.

FIGS. 8A-H illustrate that DNA damage checkpoint in G2 requires Cdh1-dependent degradation of Plk1.

FIGS. 15A-D are schematics and graphs showing that the Cdc14B-Plk1-Cdh1 axis controls the DNA damage response in G2 and is deregulated in human tumors.

FIGS. 16A-R show the analysis of mRNA levels of Cdc14B, Cdh1, and Plk1 in different human tumors.

DETAILED DESCRIPTION

Figure 6A:
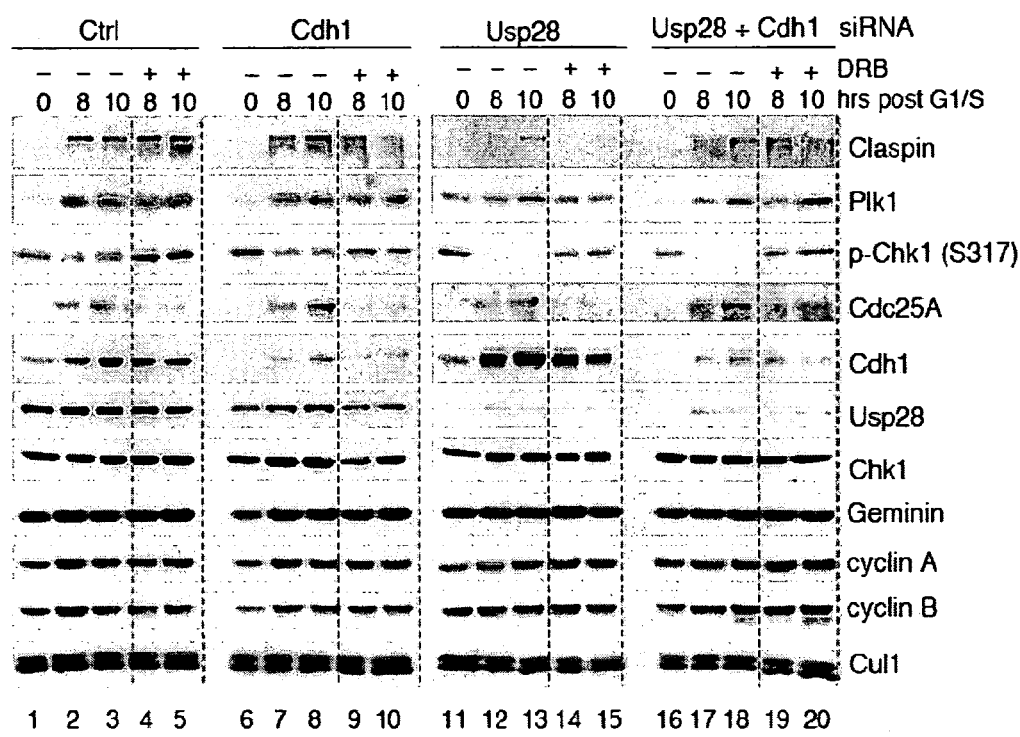

In certain embodiments, the invention relates to modulating Cdc14B levels ("cell division cycle 14 homolog B" also called "dual specificity protein phosphatase $CDCl_4B$") and/or Cdh1 levels ("fizzed related" "Fzr") to sensitize cells to DNA damage by increasing the abundance of Plk1 (polo-like kinase 1, also known as Plk, STPK13, or polo-like kinase homolog) in a target cell. In certain embodiments, the invention relates to modulating Plk1 levels, and in particular to increasing Plk1 levels, to sensitize target cells such as cancer cells to cell death or apoptosis. In certain embodiments, the invention relates to inhibitors of Cdc14B and Cdh1 that sensitize tumor cells to chemotherapy or radiation induced cell death or apoptosis. In addition to applications relating to cancer therapies and diagnostics, the Plk1 modulators and assays can be employed for identifying novel drugs or drug candidates useful for various proliferative and/or differentiative disorders such as major opportunistic infections, immune disorders, cardiovascular diseases and inflammatory disorders.

In another aspect of the present invention, the phosphatase Cdc14B has been shown to translocate from the nucleolus to the nucleoplasm in response to genotoxic stress in G2 phase and induces the activation of the ubiquitin ligase APC/$C^{Cdh1}$ (Anaphase Promoting Complex/Cyclosome and its activator Cdh1), with the consequent degradation of Plk1, a prominent promitotic kinase. This process induces the stabilization of Claspin and Wee1, because the proteolysis of these two proteins requires phosphorylation by Plk1. It was also shown that the stabilization of Claspin promotes the activation of Chk1, the stabilization of Wee1 attenuates Cdk1 activity. Consequently, inactivation of Cdc14B or Cdh1 increases the susceptibility of tumor cells to DNA damage. The elucidation of this mechanism of DNA damage response in G2 provides targets for killing tumor cells, and in particular cancer cells in cooperation with other DNA damaging or chemotherapeutic agents. In particular, these results show that modulating Plk1 activity, and in certain embodiments increasing the Plk1 activity provides a method for sensitizing cells to DNA damage leading to cell death or apoptosis of a target cell, including a cancer cell.

Identifying the Cdc14B-Cdh1-Plk1 axis as a mechanism by which Plk1 is inactivated in response to DNA damage in G2 provides a system for identifying agents and methods for potentiating the killing of cancerous cells. Certain aspects of the invention relate to using Cdc14B and Cdh1 to modulate the level of Plk1. In a particular embodiment, Cdc14B and/or Cdh1 are inactivated leading to the susceptibility of a tumor cell such as a cancer cell to DNA damage. In certain embodiments, the activity of Cdc14B and/or Cdh1 is blocked leading to the susceptibility of a tumor cell such as a cancer cell to DNA damage.

Certain embodiments of the present invention are not limited to any particular amino acid or nucleic acid sequence. In some embodiments, certain specified sequences are preferred.

Human β-TrCP1 has been sequenced and has an amino acid sequence according to Accession No. NP 378663 (SEQ ID NO:1); the β-TrCP1 coding sequence is Accession No. 033637 (SEQ ID NO:2), while a cDNA fragment corresponds to SEQ ID NO:3. The β-TrCP1 gene encodes a member of the F-box protein family which is characterized by an approximately 40 amino acid motif, the F-box (Fbox Motif β-TrCP1: DHIAENILSYLDAKSLCAAELVCKEW-YRVTSDGMLWKK (SEQ ID NO:19). The F-box proteins constitute one of the four subunits of ubiquitin protein ligase complex called SCFs (SKP1-cullin-F-box), which function in phosphorylation-dependent ubiquitination. The F-box proteins are divided into 3 classes: Fbws containing WD-40 domains, Fbls containing leucine-rich repeats, and Fbxs containing either different protein-protein interaction modules or no recognizable motifs. The protein encoded by this gene belongs to the Fbws class; in addition to an F-box, this protein contains multiple WD-40 repeats. This protein is homologous to *Xenopus* β-TrCP1, yeast Met30, *Neurospora* Scon2 and *Drosophila* Slimb proteins. It interacts with HIV-1 Vpu and connects CD4 to the proteolytic machinery. It also associates specifically with phosphorylated IκBα and β-catenin destruction motifs, most likely functioning in multiple transcriptional programs by activating the NF-κB pathway and inhibiting the β-catenin pathway. Human β-TrCP1 is a variant that contains an additional 108 nt fragment within the coding region, as compared to human variant 2 (β-TrCP2), and thus encodes an in-frame 36 aa longer isoform than human variant β-TrCP2.

Human β-TrCP2 has been sequenced and has an amino acid sequence according to GenBank Accession No. 003930 (SEQ ID NO:4); the coding sequence is GenBank Accession No. 003939 (SEQ ID NO:5).

Human Cdc25A (cell division cycle 25A protein) has been sequenced and is a 524 amino acid long protein according to GenBank Accession No. NP_001780 (SEQ ID NO:6); the coding sequence is GenBank Accession No. NM_001789 (SEQ ID NO:7).

Human Claspin protein has been characterized and has a GenBank Accession No. NP_071394.2 (SEQ ID NO:9). The coding sequence is found in GenBank Accession No. NM_022111 (SEQ ID NO:8).

Human Cdh1 (also known as Fzr1 protein, CDC20-like 1b, or fizzy-related protein) has been characterized and has GenBank Accession No. NP_057347 (SEQ ID NO:10). The coding sequence is found in GenBank Accession No. NM_016263 (SEQ ID NO:11).

Human Cdc20 has been characterized as a protein that has GenBank Accession No. CAB92757 (UniProtKB/Swiss-Prot: Q12834 (SEQ ID NO:12). The coding sequence is contained within the genome locus Genbank Accession No. AL139289.

Human Cdc14B has been characterized and has at least three isoforms/variants. The isoform 1 protein has GenBank Accession No. NM_003662 (SEQ ID NO:15). The coding sequence for isoform 1 corresponds to GenBank Accession No. NM_003671. (SEQ ID NO:16). The isoform 2 protein has GenBank Accession No. NP_201588 (SEQ ID NO: 30). The coding sequence for isoform 2 corresponds to GenBank Accession No. NM_033331 (SEQ ID NO:31). The isoform 3 protein has GenBank Accession No. NP_001070649 (SEQ ID NO:32). The coding sequence for isoform 3 corresponds to GenBank Accession No. NM_001077181. (SEQ ID NO:33).

Human Cdc14A has been characterized as a protein that has GenBank Accession No. AAH38979 (SEQ ID NO:13). The coding sequence for Cdc14A corresponds to GenBank Accession No. BC038979 (SEQ ID NO:14).

Human Plk1 wildtype (wt) has been characterized as a protein and has GenBank Accession No. P53350. (SEQ ID NO:17). Mutants R337A and L340A are utilized in the present experiments. The coding sequence corresponds to GenBank Accession No. NM_005030. (SEQ ID NO:18).

In accordance with the present invention there may be employed conventional molecular biology, microbiology, protein expression and purification, antibody, and recombinant DNA techniques within the skill of the art. Such techniques are explained fully in the literature. See, e.g., Sambrook et al. (2001) *Molecular Cloning: A Laboratory Manual*. 3$^{rd}$ ed. Cold Spring Harbor Laboratory Press: Cold Spring Harbor, N.Y.; Ausubel et al. eds. (2005) *Current Protocols in Molecular Biology*. John Wiley and Sons, Inc.: Hoboken, N.J.; Bonifacino et al. eds. (2005) *Current Protocols in Cell Biology*. John Wiley and Sons, Inc.: Hoboken, N.J.; Coligan et al. eds. (2005) *Current Protocols in Immunology*, John Wiley and Sons, Inc.: Hoboken, N.J.; Coico et al. eds. (2005) *Current Protocols in Microbiology*, John Wiley and Sons, Inc.: Hoboken, N.J.; Coligan et al. eds. (2005) *Current Protocols in Protein Science*, John Wiley and Sons, Inc.: Hoboken, N.J.; and Enna et al. eds. (2005) *Current Protocols in Pharmacology*, John Wiley and Sons, Inc.: Hoboken, N.J.; *Nucleic Acid Hybridization*, Hames & Higgins eds. (1985); *Transcription And Translation*, Hames & Higgins, eds. (1984); *Animal Cell Culture* Freshney, ed. (1986); *Immobilized Cells And Enzymes*, IRL Press (1986); Perbal, *A Practical Guide To Molecular Cloning* (1984); and Harlow and Lane. *Antibodies: A Laboratory Manual* (Cold Spring Harbor Laboratory Press: 1988).

DEFINITIONS

The following definitions are provided for clarity and illustrative purposes only, and are not intended to limit the scope of the invention.

The term apoptosis means a form of cell death in which a programmed sequence of events leads to the elimination of cells. Apoptosis plays an important role in developing and maintaining health by eliminating old cells, unnecessary cells, and unhealthy cells. The human body replaces perhaps a million cells a second. Too little or too much apoptosis plays a role in many diseases. When programmed cell death does not work properly, cells that should be eliminated may remain and become immortal. An example of the lack of proper apoptosis occurs for example, in cancer and leukemia. Impaired apoptosis is central for the development of cancer. Defects in apoptosis not only provide the cells an intrinsic survival advantage but also confer resistance to chemotherapeutic drugs. When apoptosis works too well, it kills too many cells and inflicts tissue damage. Apoptosis is also called programmed cell death or cell suicide.

As used herein, apoptosis, cell suicide, and programmed cell death are used interchangeably.

The term "cell death" is used generally to mean any type of cell death, and is not limited to programmed cell death or apoptosis A "β-transducin repeat containing protein" or "β-TrCP" herein is a protein belonging to the family of F-box proteins containing 6-7 repeats of WD40 domains. Synonyms of β-TrCP1/2 include Fbw1a, FWD1a, Fbw1b, FWD1b, FBP1, and Hos. An F-box motif is a stretch of about 40 amino acids identified as being necessary for the interaction of F-box proteins with Skp1. The consensus sequence of an F-box motif is described in Bai et al., Cell, 1996; 86:263-274, hereby incorporated by reference in its entirety. A WD40 domain is a consensus sequence of about 40 amino acid repeats rich in tryptophan (Trp) and aspartic acid (Asp) residues (Neer et al., Nature, 1996; 371:297-300 and references therein, all of which hereby incorporated by reference in their entireties). A β-TrCP protein is characterized by being capable of a substrate specificity for at least one, preferably at least two, more preferably at least three, and most preferably at least all of phosphorylated Cdc25A, β-catenin, Emi1 (Guardavaccaro et al., Developmental Cell, 2003; 4:799-812), and IkB (Soldatenkov et al., Cancer Res., 1999; 59:5085-5088). A β-TrCP protein exhibits at least 50%, 70%, 80%, 90%, 95%, 96%, 97%, 98%, or 99% sequence identity to at least one of the β-TrCP1 amino acid sequence (SEQ ID NO:1) or the β-TrCP2 amino acid sequence (SEQ ID NO:4), and includes functionally equivalent derivates of β-TrCP1 and β-TrCP2 such as mutants, conjugates (including radiolabeled or chemically tagged β-TrCP1/2), fusion proteins, and fragments thereof, which retain the substrate specificity of a β-TrCP. "β-TrCP½" means "β-TrCP1 and/or β-TrCP2".

As used herein, a "β-TrCP inhibitor" is a compound or agent that causes one or more of the following: reducing β-TrCP1/2 expression, translation, or activity, or increasing β-TrCP1/2 degradation.

A "cell division cycle 25A" or "Cdc25A" protein herein means a protein comprising a peptide sequence corresponding at least to residues 82-88 of human wild-type Cdc25A (with reference to the full sequence, SEQ ID NO:6). Preferably, the peptide sequence comprises a sequence corresponding to residues 80-93 of human wild-type Cdc25A (with reference to the full sequence, SEQ ID NO:6). To function as a substrate for a β-TrCP, the serine residues corresponding to residues 82 and 88 of SEQ ID NO:6 must be at least phosphorylated, preferably double phosphorylated. Exemplary Cdc25A fragments useful for testing binding to or ubiquitination by β-TrCP1/2 include peptides corresponding to residues 73-95 of SEQ ID NO:6 and residues 80-93 of SEQ ID NO:6.

Cdc14B ("cell division cycle 14 homolog B" also called "dual specificity protein phosphatase CDCl$_4$B"). This protein is highly similar to Saccharomyces cerevisiae Cdc14, a protein tyrosine phosphatase involved in the exit of cell mitosis and initiation of DNA replication, which suggests the role in cell cycle control.

Cdh1 serves to sensitize cells to DNA damage by increasing the abundance of Plk1 (polo-like kinase 1, also known as Plk, STPK13, or polo-like kinase homolog) in a target cell. Cdh1 regulates ubiquitin ligase activity of the anaphase promoting complex/cyclosome (APC/C) confers substrate specificity upon the complex. The APC/C-Cdh1 dimeric complex is activated during anaphase and telophase and remains active in degrading substrates until onset of the next S phase.

Plk1 (polo-like kinase 1, also known as Plk, STPK13, or polo-like kinase homolog) is involved in the formation of and the changes in the mitotic spindle and in the activation of CDK/cyclin complexes during the M-phase of mitosis. Plk1 is involved in the formation of and the changes in the mitotic spindle and in the activation of CDK/cyclin complexes during the M-phase of mitosis.

A "DNA damaging agent" is a chemical compound or treatment method that induces DNA damage when applied to a cell, including single-strand breaks, double-strand breaks and alkylation. Such agents include, without limitation, ionizing radiation and waves that induce DNA damage, such as γ-irradiation, X-rays, UV-irradiation, microwaves, electronic emissions, and the like. A variety of chemical compounds, also described as "chemotherapeutic agents", function to induce DNA damage, all of which are intended to be of use in the combined treatment methods disclosed herein. Contemplated chemotherapeutic agents include alkylating agents such as mitomycin C, adozelesin, cis-platinum, and nitrogen mustard.

"Ubiquitin ligation", "ubiquitination", and "ubiquitinylation" as used herein all refer to the addition of a ubiquitin polypeptide to a protein substrate targeted for degradation.

About or Approximately

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Unless otherwise stated, the term 'about' means within an acceptable error range for the particular value.

Administration

In the case of the present invention, parenteral routes of administration are also possible. Such routes include intravenous, intra-arteriole, intramuscular, intradermal, subcutaneous, intraperitoneal, transmucosal, intranasal, rectal, vaginal, or transdermal routes. If desired, inactivated therapeutic formulations may be injected, e.g., intravascular, intratumor, subcutaneous, intraperitoneal, intramuscular, etc. In a preferred embodiment, the route of administration is oral. Although there are no physical limitations to delivery of the formulation, oral delivery is preferred because of its ease and convenience, and because oral formulations readily accommodate additional mixtures, such as milk and infant formula.

Adjuvant

As used herein, the term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., Immunology, Second Ed., 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, and potentially useful human adjuvants such as N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine, BCG (bacille Calmette-Guerin) and Corynebacterium parvum. Preferably, the adjuvant is pharmaceutically acceptable.

Amplification

"Amplification" of DNA as used herein denotes the use of polymerase chain reaction (PCR) to increase the concentration of a particular DNA sequence within a mixture of DNA sequences. For a description of PCR see Saiki et al., Science 1988, 239:487.

Carrier

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

Coding Sequence or a Sequence Encoding an Expression Product

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually, but not always, ATG) and a stop codon.

Dosage

The dosage of the therapeutic formulation will vary widely, depending upon the nature of the disease, the patient's medical history, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc., to maintain an effective dosage level. In some cases, oral administration will require a higher dose than if administered intravenously.

Expression Construct

By "expression construct" is meant a nucleic acid sequence comprising a target nucleic acid sequence or sequences whose expression is desired, operatively associated with expression control sequence elements which provide for the proper transcription and translation of the target nucleic acid sequence(s) within the chosen host cells. Such sequence elements may include a promoter and a polyadenylation signal. The "expression construct" may further comprise "vector sequences." By "vector sequences" is meant any of several nucleic acid sequences established in the art which have utility in the recombinant DNA technologies of the invention to facilitate the cloning and propagation of the expression constructs including (but not limited to) plasmids, cosmids, phage vectors, viral vectors, and yeast artificial chromosomes.

Expression constructs of the present invention may comprise vector sequences that facilitate the cloning and propagation of the expression constructs. A large number of vectors, including plasmid and fungal vectors, have been described for replication and/or expression in a variety of eukaryotic and prokaryotic host cells. Standard vectors useful in the current invention are well known in the art and include (but are not limited to) plasmids, cosmids, phage vectors, viral vectors, and yeast artificial chromosomes. The vector sequences may contain a replication origin for propagation in *E. coli*; the SV40 origin of replication; an ampicillin, neomycin, or puromycin resistance gene for selection in host cells; and/or genes (e.g., dihydrofolate reductase gene) that amplify the dominant selectable marker plus the gene of interest.

Express and Expression

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a foreign nucleic acid into a cell. The term "transformation" means the introduction of a "foreign" (i.e. extrinsic or extracellular) gene, DNA or RNA sequence to a cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cells genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

Expression System

The term "expression system" means a host cell and compatible vector under suitable conditions, e.g. for the expression of a protein coded for by foreign DNA carried by the vector and introduced to the host cell.

Gene or Structural Gene

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

A coding sequence is "under the control of" or "operatively associated with" expression control sequences in a cell when RNA polymerase transcribes the coding sequence into RNA, particularly mRNA, which is then trans-RNA spliced (if it contains introns) and translated into the protein encoded by the coding sequence.

The term "expression control sequence" refers to a promoter and any enhancer or suppression elements that combine to regulate the transcription of a coding sequence. In a preferred embodiment, the element is an origin of replication.

Heterologous

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. For example, the present invention includes chimeric DNA molecules that comprise a DNA sequence and a heterologous DNA sequence which is not part of the DNA sequence. A heterologous expression regulatory element is such an element that is operatively associated with a different gene than the one it is operatively associated with in nature. In the context of the present invention, a gene encoding a protein of interest is heterologous to the vector DNA in which it is inserted for cloning or expression, and it is heterologous to a host cell containing such a vector, in which it is expressed.

Homologous

The term "homologous" as used in the art commonly refers to the relationship between nucleic acid molecules or proteins that possess a "common evolutionary origin," including nucleic acid molecules or proteins within superfamilies (e.g., the immunoglobulin superfamily) and nucleic acid molecules or proteins from different species (Reeck et al., *Cell* 1987; 50: 667). Such nucleic acid molecules or proteins have sequence homology, as reflected by their sequence similarity, whether in terms of substantial percent similarity or the presence of specific residues or motifs at conserved positions.

Host Cell

The term "host cell" means any cell of any organism that is selected, modified, transformed, grown or used or manipulated in any way for the production of a substance by the cell.

For example, a host cell may be one that is manipulated to express a particular gene, a DNA or RNA sequence, a protein or an enzyme. Host cells can further be used for screening or other assays that are described infra. Host cells may be cultured in vitro or one or more cells in a non-human animal (e.g., a transgenic animal or a transiently transfected animal). Suitable host cells include but are not limited to *Streptomyces* species and *E. Coli*.

Immune Response

An "immune response" refers to the development in the host of a cellular and/or antibody-mediated immune response to a composition or vaccine of interest. Such a response usually consists of the subject producing antibodies, B cells, helper T cells, suppressor T cells, and/or cytotoxic T cells directed specifically to an antigen or antigens included in the composition or vaccine of interest.

Isolated

As used herein, the term "isolated" means that the referenced material is removed from the environment in which it is normally found. Thus, an isolated biological material can be free of cellular components, i.e., components of the cells in which the material is found or produced. Isolated nucleic acid molecules include, for example, a PCR product, an isolated mRNA, a cDNA, or a restriction fragment. Isolated nucleic acid molecules also include, for example, sequences inserted into plasmids, cosmids, artificial chromosomes, and the like. An isolated nucleic acid molecule is preferably excised from the genome in which it may be found, and more preferably is no longer joined to non-regulatory sequences, non-coding sequences, or to other genes located upstream or downstream of the nucleic acid molecule when found within the genome. An isolated protein may be associated with other proteins or nucleic acids, or both, with which it associates in the cell, or with cellular membranes if it is a membrane-associated protein.

Mutant

As used herein, the terms "mutant" and "mutation" refer to any detectable change in genetic material (e.g., DNA) or any process, mechanism, or result of such a change. This includes gene mutations, in which the structure (e.g., DNA sequence) of a gene is altered, any gene or DNA arising from any mutation process, and any expression product (e.g., protein or enzyme) expressed by a modified gene or DNA sequence. As used herein, the term "mutating" refers to a process of creating a mutant or mutation.

Nucleic Acid Hybridization

The term "nucleic acid hybridization" refers to anti-parallel hydrogen bonding between two single-stranded nucleic acids, in which A pairs with T (or U if an RNA nucleic acid) and C pairs with G. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an anti-parallel hybrid). See *Molecular Biology of the Cell*, Alberts et al., $3^{rd}$ ed., New York and London: Garland Publ., 1994, Ch. 7.

Typically, hybridization of two strands at high stringency requires that the sequences exhibit a high degree of complementarity over an extended portion of their length. Examples of high stringency conditions include: hybridization to filter-bound DNA in 0.5 M $NaHPO_4$, 7% SDS, 1 mM EDTA at 65° C., followed by washing in 0.1×SSC/0.1% SDS at 68° C. (where 1×SSC is 0.15M NaCl, 0.15M Na citrate) or for oligonucleotide molecules washing in 6×SSC/0.5% sodium pyrophosphate at about 37° C. (for 14 nucleotide-long oligos), at about 48° C. (for about 17 nucleotide-long oligos), at about 55° C. (for 20 nucleotide-long oligos), and at about 60° C. (for 23 nucleotide-long oligos)). Accordingly, the term "high stringency hybridization" refers to a combination of solvent and temperature where two strands will pair to form a "hybrid" helix only if their nucleotide sequences are almost perfectly complementary (see *Molecular Biology of the Cell*, Alberts et al., $3^{rd}$ ed., New York and London: Garland Publ., 1994, Ch. 7).

Conditions of intermediate or moderate stringency (such as, for example, an aqueous solution of 2×SSC at 65° C.; alternatively, for example, hybridization to filter-bound DNA in 0.5 M $NaHPO_4$, 7% SDS, 1 mM EDTA at 65° C., and washing in 0.2×SSC/0.1% SDS at 42° C.) and low stringency (such as, for example, an aqueous solution of 2×SSC at 55° C.), require correspondingly less overall complementarity for hybridization to occur between two sequences. Specific temperature and salt conditions for any given stringency hybridization reaction depend on the concentration of the target DNA and length and base composition of the probe, and are normally determined empirically in preliminary experiments, which are routine (see Southern, *J. Mol. Biol.* 1975; 98: 503; Sambrook et al., *Molecular Cloning: A Laboratory Manual*, $2^{nd}$ ed., vol. 2, ch. 9.50, CSH Laboratory Press, 1989; Ausubel et al. (eds.), 1989, *Current Protocols in Molecular Biology*, Vol. I, Green Publishing Associates, Inc., and John Wiley & Sons, Inc., New York, at p. 2.10.3).

As used herein, the term "standard hybridization conditions" refers to hybridization conditions that allow hybridization of sequences having at least 75% sequence identity. According to a specific embodiment, hybridization conditions of higher stringency may be used to allow hybridization of only sequences having at least 80% sequence identity, at least 90% sequence identity, at least 95% sequence identity, or at least 99% sequence identity.

Nucleic acid molecules that "hybridize" to any desired nucleic acids of the present invention may be of any length. In one embodiment, such nucleic acid molecules are at least 10, at least 15, at least 20, at least 30, at least 40, at least 50, and at least 70 nucleotides in length. In another embodiment, nucleic acid molecules that hybridize are of about the same length as the particular desired nucleic acid.

Nucleic Acid Molecule

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

Orthologs

As used herein, the term "orthologs" refers to genes in different species that apparently evolved from a common ancestral gene by speciation. Normally, orthologs retain the same function through the course of evolution. Identification of orthologs can provide reliable prediction of gene function in newly sequenced genomes. Sequence comparison algorithms that can be used to identify orthologs include without limitation BLAST, FASTA, DNA Strider, and the GCG pileup program. Orthologs often have high sequence similarity. The present invention encompasses all orthologs of the desired protein.

Operatively Associated

By "operatively associated with" is meant that a target nucleic acid sequence and one or more expression control sequences (e.g., promoters) are physically linked so as to permit expression of the polypeptide encoded by the target nucleic acid sequence within a host cell.

Patient or Subject

"Patient" or "subject" refers to mammals and includes human and veterinary subjects.

Percent Sequence Similarity or Percent Sequence Identity

The terms "percent (%) sequence similarity", "percent (%) sequence identity", and the like, generally refer to the degree of identity or correspondence between different nucleotide sequences of nucleic acid molecules or amino acid sequences of proteins that may or may not share a common evolutionary origin (see Reeck et al., supra). Sequence identity can be determined using any of a number of publicly available sequence comparison algorithms, such as BLAST, FASTA, DNA Strider, GCG (Genetics Computer Group, Program Manual for the GCG Package, Version 7, Madison, Wis.), etc.

To determine the percent identity between two amino acid sequences or two nucleic acid molecules, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are, or are about, of the same length. The percent identity between two sequences can be determined using techniques similar to those described below, with or without allowing gaps. In calculating percent sequence identity, typically exact matches are counted.

The determination of percent identity between two sequences can be accomplished using a mathematical algorithm. A non-limiting example of a mathematical algorithm utilized for the comparison of two sequences is the algorithm of Karlin and Altschul, *Proc. Natl. Acad. Sci. USA* 1990, 87:2264, modified as in Karlin and Altschul, *Proc. Natl. Acad. Sci. USA* 1993, 90:5873-5877. Such an algorithm is incorporated into the NBLAST and XBLAST programs of Altschul et al., *J. Mol. Biol.* 1990; 215: 403. BLAST nucleotide searches can be performed with the NBLAST program, score=100, wordlength=12, to obtain nucleotide sequences homologous to sequences of the invention. BLAST protein searches can be performed with the XBLAST program, score=50, wordlength=3, to obtain amino acid sequences homologous to protein sequences of the invention. To obtain gapped alignments for comparison purposes, Gapped BLAST can be utilized as described in Altschul et al., *Nucleic Acids Res.* 1997, 25:3389. Alternatively, PSI-Blast can be used to perform an iterated search that detects distant relationship between molecules. See Altschul et al. (1997) supra. When utilizing BLAST, Gapped BLAST, and PSI-Blast programs, the default parameters of the respective programs (e.g., XBLAST and NBLAST) can be used. See ncbi.nlm.nih.gov/BLAST/ on the WorldWideWeb. Another non-limiting example of a mathematical algorithm utilized for the comparison of sequences is the algorithm of Myers and Miller, *CABIOS* 1988; 4: 11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

In a preferred embodiment, the percent identity between two amino acid sequences is determined using the algorithm of Needleman and Wunsch (*J. Mol. Biol.* 1970, 48:444-453), which has been incorporated into the GAP program in the GCG software package (Accelrys, Burlington, Mass.; available at accelrys.com on the WorldWideWeb), using either a Blossum 62 matrix or a PAM250 matrix, a gap weight of 16, 14, 12, 10, 8, 6, or 4, and a length weight of 1, 2, 3, 4, 5, or 6. In yet another preferred embodiment, the percent identity between two nucleotide sequences is determined using the GAP program in the GCG software package using a NWSgapdna.CMP matrix, a gap weight of 40, 50, 60, 70, or 80, and a length weight of 1, 2, 3, 4, 5, or 6. A particularly preferred set of parameters (and the one that can be used if the practitioner is uncertain about what parameters should be applied to determine if a molecule is a sequence identity or homology limitation of the invention) is using a Blossum 62 scoring matrix with a gap open penalty of 12, a gap extend penalty of 4, and a frameshift gap penalty of 5.

In addition to the cDNA sequences encoding various desired proteins, the present invention further provides polynucleotide molecules comprising nucleotide sequences having certain percentage sequence identities to any of the aforementioned sequences. Such sequences preferably hybridize under conditions of moderate or high stringency as described above, and may include species orthologs.

Pharmaceutically Acceptable

When formulated in a pharmaceutical composition, a therapeutic compound such as an inhibitor of Cdc14B and/or Cdh1 can be admixed with a pharmaceutically acceptable carrier or excipient. As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human.

Pharmaceutically Acceptable Derivative

The term "pharmaceutically acceptable derivative" as used herein means any pharmaceutically acceptable salt, solvate or prodrug, e.g. ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol 1: Principles and Practice, which is incorporated herein by reference to the extent of teaching such derivatives. Preferred pharmaceutically acceptable derivatives are salts, solvates, esters, carbamates, and phosphate esters. Particularly preferred pharmaceutically acceptable derivatives are salts, solvates, and esters. Most preferred pharmaceutically acceptable derivatives are salts and esters.

Pharmaceutical Compositions and Administration

While it is possible to use a composition provided by the present invention for therapy as is, it may be preferable to administer it in a pharmaceutical formulation, e.g., in admixture with a suitable pharmaceutical excipient, diluent or carrier selected with regard to the intended route of administration and standard pharmaceutical practice. Accordingly, in one aspect, the present invention provides a pharmaceutical composition or formulation comprising at least one active composition, or a pharmaceutically acceptable derivative thereof, in association with a pharmaceutically acceptable excipient, diluent and/or carrier. The excipient, diluent and/or carrier must be "acceptable" in the sense of being compatible with the other ingredients of the formulation and not deleterious to the recipient thereof.

The compositions of the invention can be formulated for administration in any convenient way for use in human or veterinary medicine. The invention therefore includes within its scope pharmaceutical compositions comprising a product of the present invention that is adapted for use in human or veterinary medicine, including treating food allergies and related immune disorders.

In a preferred embodiment, the pharmaceutical composition is conveniently administered as an oral formulation. Oral dosage forms are well known in the art and include tablets, caplets, gelcaps, capsules, and medical foods. Tablets, for example, can be made by well-known compression techniques using wet, dry, or fluidized bed granulation methods.

Pharmaceutically acceptable excipients assist or make possible the formation of a dosage form for a bioactive material and include diluents, binding agents, lubricants, glidants, disintegrants, coloring agents, and other ingredients. Preservatives, stabilizers, dyes and even flavoring agents may be provided in the pharmaceutical composition. Examples of preservatives include sodium benzoate, ascorbic acid and esters of p-hydroxybenzoic acid. Antioxidants and suspending agents may be also used. An excipient is pharmaceutically acceptable if, in addition to performing its desired function, it is non-toxic, well tolerated upon ingestion, and does not interfere with absorption of bioactive materials.

Acceptable excipients, diluents, and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient, diluent, and carrier can be selected with regard to the intended route of administration and standard pharmaceutical practice.

The term "therapeutically effective amount" is used herein to mean an amount or dose sufficient to modulate, e.g., increase or decrease as appropriate, the expression or activity level of a desired protein e.g., by about 10 percent, preferably by about 50 percent, and more preferably by about 80-90 percent. In certain embodiments, the amount of Plk1 is increased as a result of decreasing the amount of Cdc14B and/or Cdh1. Preferably, a therapeutically effective amount is sufficient to cause an improvement in a clinically significant condition in the host following a therapeutic regimen involving one or more inhibitors of Cdc14B and/or Cdh1. The concentration or amount of the active ingredient depends on the desired dosage and administration regimen, as discussed below. Suitable dosages may range from about 0.01 mg/kg to about 100 mg/kg of body weight per day, week, or month. The pharmaceutical compositions may also include other biologically active compounds.

According to the invention, a therapeutically effective amount of a Cdc14B and/or Cdh1 inhibitor can be formulated in a pharmaceutical composition of the invention to be introduced parenterally, transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration. Optionally, the Cdc14B and/or Cdh1 inhibitor can be formulated together with an DNA damaging agent such as an alkylating agent.

In another embodiment, the active ingredient can be delivered in a vesicle, in particular a liposome (see Langer, Science, 1990; 249:1527-1533; Treat et al., in Liposomes in the Therapy of Infectious Disease and Cancer, Lopez-Berestein and Fidler (eds.), Liss: New York, pp. 353-365 (1989); Lopez-Berestein, ibid., pp. 317-327; see generally ibid.).

In yet another embodiment, the therapeutic compound(s) can be delivered in a controlled release system. For example, a polypeptide may be administered using intravenous infusion with a continuous pump, in a polymer matrix such as poly-lactic/glutamic acid (PLGA), a pellet containing a mixture of cholesterol and the active ingredient (Silastic®; Dow Corning, Midland, Mich.; see U.S. Pat. No. 5,554,601) implanted subcutaneously, an implantable osmotic pump, a transdermal patch, liposomes, or other modes of administration.

The effective amounts of compounds of the present invention include doses that partially or completely achieve the desired therapeutic, prophylactic, and/or biological effect. The actual amount effective for a particular application depends on the condition being treated and the route of administration. The effective amount for use in humans can be determined from animal models. For example, a dose for humans can be formulated to achieve circulating and/or gastrointestinal concentrations that have been found to be effective in animals.

Kits

The invention provides a kit for screening for an agent useful for inhibiting Cdc14B and/or Cdh1 activity, comprising: a Plk1 protein, at least one of Cdc14B or Cdh1 protein, a means for detecting binding between the Plk1 and Cdc148 and/or Cdh1 protein, optionally packaged in association with instructions teaching one or more of the methods described herein. In certain embodiments, the invention provides a kit for screening for an agent useful for increasing the amount of Plk1 protein comprising: a Plk1 protein, at least one Cdc14B or Cdh1 protein, a means for detecting binding between the Plk1 and the Cdc14B and/or Cdh1 protein, optionally packaged in association with instructions teaching one or more of the methods described herein.

Polynucleotide or Nucleotide Sequence

A "polynucleotide" or "nucleotide sequence" is a series of nucleotide bases (also called "nucleotides") in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

Promoter

The promoter sequences may be endogenous or heterologous to the host cell to be modified, and may provide ubiquitous (i.e. +, expression occurs in the absence of an apparent external stimulus) or inducible (i.e., expression only occurs in presence of particular stimuli) expression. Promoters which may be used to control gene expression include, but are not limited to, cytomegalovirus (CMV) promoter (U.S. Pat. No. 5,385,839 and No. 5,168,062), the SV40 early promoter region (Benoist and Chambon, Nature 1981; 290:304-310), the promoter contained in the 3' long terminal repeat of Rous sarcoma virus (Yamamoto, et al., Cell 1980; 22:787-797), the herpes thymidine kinase promoter (Wagner et al., Proc. Natl. Acad. Sci. USA 1981; 78:1441-1445), the regulatory sequences of the metallothionein gene (Brinster et al., Nature 1982; 296:39-42); prokaryotic promoters such as the alkaline phosphatase promoter, the trp-lac promoter, the bacteriophage lambda $P_L$ promoter, the T7 promoter, the beta-lactamase promoter (Villa-Komaroff, et al., Proc. Natl. Acad. Sci. USA 1978; 75:3727-3731), or the tac promoter (DeBoer, et al., Proc. Natl. Acad. Sci. USA 1983; 80:21-25); see also "Useful proteins from recombinant bacteria" in Scientific American 1980; 242:74-94; promoter elements from yeast or other fungi such as the Gal4 promoter, the ADC (alcohol dehydrogenase) promoter, and the PGK (phosphoglycerol kinase) promoter.

Small Molecule

The term "small molecule" refers to a compound that has a molecular weight of less than about 2000 Daltons, less than about 1000 Daltons, or less than about 500 Daltons. Small molecules, without limitation, may be, for example, nucleic acids, peptides, polypeptides, peptide nucleic acids, peptidomimetics, carbohydrates, lipids, or other organic (carbon containing) or inorganic molecules and may be synthetic or naturally occurring or optionally derivatized. Such small molecules may be a therapeutically deliverable substance or may be further derivatized to facilitate delivery or targeting.

Substantially Homologous or Substantially Similar

In a specific embodiment, two DNA sequences are "substantially homologous" or "substantially similar" when at least about 80%, and most preferably at least about 90% or 95% of the nucleotides match over the defined length of the DNA sequences, as determined by sequence comparison algorithms, such as BLAST, FASTA, DNA Strider, etc. An example of such a sequence is an allelic or species variant of the specific genes of the invention. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially homologous" or "substantially similar" when greater than 80% of the amino acids are identical, or greater than about 90% are similar. Preferably, the amino acids are functionally identical. Preferably, the similar or homologous sequences are identified by alignment using, for example, the GCG (Genetics Computer Group, Program Manual for the GCG Package, Version 10, Madison, Wis.) pileup program, or any of the programs described above (BLAST, FASTA, etc.).

Substantially Identical

By "substantially identical" is meant a polypeptide or nucleic acid molecule exhibiting at least 80%, more preferably at least 90%, and most preferably at least 95% identity in comparison to a reference amino acid or nucleic acid sequence. For polypeptides, the length of sequence comparison will generally be at least 20 amino acids, preferably at least 30 amino acids, more preferably at least 40 amino acids, and most preferably at least 50 amino acids. For nucleic acid molecules, the length of sequence comparison will generally be at least 60 nucleotides, preferably at least 90 nucleotides, and more preferably at least 120 nucleotides.

The degree of sequence identity between any two nucleic acid molecules or two polypeptides may be determined by sequence comparison and alignment algorithms known in the art, including but not limited to BLAST, FASTA, DNA Strider, and the GCG Package (Madison, Wis.) pileup program (see, for example, Gribskov and Devereux Sequence *Analysis Primer* (Stockton Press: 1991) and references cited therein). The percent similarity between two nucleotide sequences may be determined, for example, using the Smith-Waterman algorithm as implemented in the BESTFIT software program using default parameters.

Therapeutically Effective Amount

A "therapeutically effective amount" means the amount of a compound that, when administered to a mammal for treating a state, disorder or condition, is sufficient to effect such treatment. The "therapeutically effective amount" will vary depending on the compound, the disease and its severity and the age, weight, physical condition and responsiveness of the mammal to be treated.

Therapeutically or Prophylactically Effective Amount of an Antibody

The compositions of the invention may include a "therapeutically effective amount" or a "prophylactically effective amount" of an antibody or antigen-binding portion of the desired inhibitor. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Transfection

By "transfection" is meant the process of introducing one or more of the expression constructs of the invention into a host cell by any of the methods well established in the art, including (but not limited to) microinjection, electroporation, liposome-mediated transfection, calcium phosphate-mediated transfection, or virus-mediated transfection.

Treating or Treatment

"Treating" or "treatment" of a state, disorder or condition includes:

(1) preventing or delaying the appearance of clinical or sub-clinical symptoms of the state, disorder or condition developing in a mammal that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms.

The benefit to a subject to be treated is either statistically significant or at least perceptible to the patient or to the physician.

Variant

The term "variant" may also be used to indicate a modified or altered gene, DNA sequence, enzyme, cell, etc., i.e., any kind of mutant.

Vector, Cloning Vector and Expression Vector

The terms "vector", "cloning vector" and "expression vector" refer to the vehicle by which DNA can be introduced into a host cell, resulting in expression of the introduced sequence. In one embodiment, vectors comprise a promoter and one or more control elements (e.g., enhancer elements) that are heterologous to the introduced DNA but are recognized and used by the host cell. In another embodiment, the sequence that is introduced into the vector retains its natural promoter that may be recognized and expressed by the host cell (Bormann et al., J. Bacteriol. 1996; 178:1216-1218).

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct". A common type of vector is a "plasmid", which generally is a self-contained molecule of double-stranded DNA, usually of bacterial origin, that can readily accept additional (foreign) DNA and which can readily be introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. Recombinant cloning vectors will often include one or more replication systems for cloning or expression, one or more markers for selection in the host, e.g. antibiotic resistance, and one or more expression cassettes. Vector constructs may be produced using conventional molecular biology and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); F. M. Ausubel et al. (eds.), Current Protocols in Molecular Biology, John Wiley & Sons, Inc. (1994).

The abbreviations in the specification correspond to units of measure, techniques, properties or compounds as follows: "min" means minutes, "h" means hour(s), "4" means microliter(s), "mL" means milliliter(s), "mM" means millimolar, "M" means molar, "mmole" means millimole(s), "kb" means kilobase, "bp" means base pair(s), "nt" means nucleotide, and "IU" means International Units. "Polymerase chain reaction" is abbreviated PCR; "Reverse transcriptase polymerase chain reaction" is abbreviated RT-PCR; "Estrogen receptor" is abbreviated ER; "DNA binding domain" is abbreviated DBD; "Untranslated region" is abbreviated UTR; "Sodium dodecyl sulfate" is abbreviated SDS; and "High Pressure Liquid Chromatography" is abbreviated HPLC.

Expression Plk1, Cdc14B and Cdh1 and Related Substrates

For the screening and evaluation of compounds for their ability to modulate the Plk1 interaction with Cdc14B and/or Cdh1, or other Plk1 substrates, both in vitro (including reconstituted systems) and in vivo systems (including cellular systems and transgenic animals) systems can be used. Regardless of the screening or testing system of choice, various expression methods can be employed to provide the protein components or cellular/transgenic animals to be used in the method.

A wide variety of host/expression vector combinations (i.e., expression systems) may be employed in expressing DNA sequences for Plk1, Cdc14B or fragments or mutants thereof, Cdh1 or fragments or mutants thereof, Cdc25A or fragments or mutants thereof. Additionally, DNA sequences expressing any of Skp1, Cul1, β-catenin, Emi1, IκB-α, IκB-β, IκB-ε, USP48, βTRCP1/2, Cdc 20, Cdc14B, or Fbxw 4-7, and other components are included as desirable host/expression vector combinations. These may be co-expressed from the same vector, expressed from different vectors, or one may be expressed while the other one is added externally to the screening or evaluation system. Useful expression vectors, for example, may consist of segments of chromosomal, non chromosomal and synthetic DNA sequences. Suitable vectors include derivatives of SV40 and known bacterial plasmids, e.g., E. coli plasmids col E1, pCR1, pBR322, pMal-C2, pET, pGEX (Smith et al., Gene, 1988; 67:31-40), pMB9 and their derivatives, plasmids such as RP4; phage DNAS, e.g., the numerous derivatives of phage 1, e.g., NM989, and other phage DNA, e.g., M13 and filamentous single stranded phage DNA; yeast plasmids such as the 2m plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like. In a preferred embodiment, various tumor cells lines can be used in expression systems of the invention.

Yeast expression systems can also be used according to the invention to express any protein of interest. For example, the non-fusion pYES2 vector (XbaI, SphI, ShoI, NotI, GstXI, EcoRI, BstXI, BamH1, SacI, Kpn1, and HindIII cloning site; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), for example, can be employed according to the invention.

Expression of the protein or polypeptide may be controlled by any promoter/enhancer element known in the art, but these regulatory elements must be functional in the host selected for expression. Promoters which may be used to control gene expression include, but are not limited to, cytomegalovirus (CMV) promoter (U.S. Pat. No. 5,385,839 and No. 5,168,062), the SV40 early promoter region (Benoist and Chambon, Nature, 1981; 290:304-310), the promoter contained in the 3' long terminal repeat of Rous sarcoma virus (Yamamoto, et al., Cell, 1980; 22:787-797), the herpes thymidine kinase promoter (Wagner et al., Proc. Natl. Acad. Sci. U.S.A., 1981; 78:1441-1445), the regulatory sequences of the metallothionein gene (Brinster et al., Nature, 1982; 296:39 42); prokaryotic expression vectors such as the β-lactamase promoter (Villa-Komaroff, et al., Proc. Natl. Acad. Sci. U.S.A., 1978; 75:3727-3731), or the tac promoter (DeBoer, et al., Proc. Natl. Acad. Sci. U.S.A., 1983; 80:21-25); see also "Useful proteins from recombinant bacteria" in Scientific American, 1980; 242:74-94; promoter elements from yeast or other fungi such as the Gal 4 promoter, the ADC (alcohol dehydrogenase) promoter, PGK (phosphoglycerol kinase) promoter, alkaline phosphatase promoter; and transcriptional control regions that exhibit hematopoietic tissue specificity, in particular: beta-globin gene control region which is active in myeloid cells (Mogram et al., Nature, 1985; 315:338-340; Kollias et al., Cell, 1986; 46:89-94), hematopoietic stem cell differentiation factor promoters, erythropoietin receptor promoter (Maouche et al., Blood, 1991; 15:2557), etc.

Preferred vectors, particularly for cellular assays in vitro and in vivo, are viral vectors, such as lentiviruses, retroviruses, herpes viruses, adenoviruses, adeno-associated viruses, vaccinia virus, baculovirus, and other recombinant viruses with desirable cellular tropism. Thus, a gene encoding a functional or mutant protein or polypeptide domain fragment thereof can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in International Patent Publication WO 95/28494, published October 1995.

Viral vectors commonly used for in vivo or ex vivo targeting and therapy procedures are DNA-based vectors and retroviral vectors. Methods for constructing and using viral vectors are known in the art (see, e.g., Miller and Rosman, BioTechniques, 1992; 7:980-990). Preferably, the viral vectors are replication defective, that is, they are unable to replicate autonomously in the target cell. Preferably, the replication defective virus is a minimal virus, i.e., it retains only the sequences of its genome which are necessary for encapsidating the genome to produce viral particles.

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Molec. Cell. Neurosci., 1991; 2:320-330), defective herpes virus vector lacking a glycoprotein L gene (Patent Publication RD 371005 A), or other defective herpes virus vectors (International Patent Publication No. WO 94/21807, published Sep. 29, 1994; International Patent Publication No. WO 92/05263, published Apr. 2, 1994); an attenuated adenovirus vector, such as the vector described by Stratford-Perricaudet et al. (J. Clin. Invest., 1992; 90:626-630; see also La Salle et al., Science, 1993; 259:988-990); and a defective adeno-associated virus vector (Samulski et al., J. Virol., 1987; 61:3096-3101; Samulski et al., J. Virol., 1989; 63:3822-3828; Lebkowski et al., Mol. Cell. Biol., 1988; 8:3988-3996).

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors (see, e.g., Wilson, Nature Medicine 1995). In that regard, it is advantageous to employ a viral vector that is engineered to express a minimal number of antigens.

It is also possible to introduce the vector in vivo as a naked DNA plasmid. Naked DNA vectors for gene therapy can be introduced into the desired host cells by methods known in the art, e.g., electroporation, microinjection, cell fusion, DEAE dextran, calcium phosphate precipitation, use of a gene gun, or use of a DNA vector transporter (see, e.g., Wu et al., J. Biol. Chem., 1992; 267:963-967; Wu and Wu, J. Biol. Chem., 1988; 263:14621-14624; Hartmut et al., Canadian Patent Application No. 2,012,311, filed Mar. 15, 1990; Williams et al., Proc. Natl. Acad. Sci. USA, 1991; 88:2726-2730). Receptor-mediated DNA delivery approaches can also be used (Curiel et al., Hum. Gene Ther., 1992; 3:147-154; Wu and Wu, J. Biol. Chem., 1987; 262:4429-4432). U.S. Pat. Nos. 5,580,859 and 5,589,466 disclose delivery of exogenous DNA sequences, free of transfection facilitating agents, in a mammal. A relatively low voltage, high efficiency in vivo DNA transfer technique, termed electrotransfer, has also been described (Mir et al., C.P. Acad. Sci., 1998; 321:893; WO 99/01157; WO 99/01158; WO 99/01175).

Another option is to transcribe and translate cDNA sequences in vitro. Various commercial systems are available for such techniques, including the TNT Quick Coupled Transcription/Translation System with Transcend™ (Promega, Madison, Wis.). For in vitro production of labeled or modified peptides or proteins, labeled or chemically modified amino acid precursors such as, e.g., $^{35}$S-methionine or phosphoserine, can be added to the translation system.

Transgenic Animals

Transgenic mammals can be prepared for evaluating the interaction of human Plk1 with Cdc14B and/or Cdh1, or any other Plk1 substrates. Such mammals provide excellent models for screening or testing drug candidates, i.e., inhibitors of Cdc14B and/or Cdh1. Thus, human BimEL "knock-in" mammals can be prepared for evaluating the molecular biology of this system in greater detail than is possible with human subjects. In one embodiment, the animal can be double-transgenic, in that both human human Cdc14B and Cdh1 are expressed in the transgenic animal. It is also possible to evaluate compounds or diseases in "knock-out" animals, e.g., to identify a compound that can compensate for a defect in Cdc14B and/or Cdh1. Both technologies permit manipulation of single units of genetic information in their natural position in a cell genome and to examine the results of that manipulation in the background of a terminally differentiated organism. Transgenic mammals can be prepared by any method, including but not limited to modification of embryonic stem (ES) cells and heteronuclear injection into blast cells.

A "knock-in" mammal is a mammal in which an endogenous gene is substituted with a heterologous gene (Roemer et al., New Biol., 1991; 3:331). Preferably, the heterologous gene is "knocked-in" to a locus of interest, either the subject of evaluation (in which case the gene may be a reporter gene; see Elefanty et al., Proc. Natl. Acad. Sci. USA, 1998; 95:11897) of expression or function of a homologous gene, thereby linking the heterologous gene expression to transcription from the appropriate promoter. This can be achieved by homologous recombination, transposon (Westphal and Leder, Curr. Biol., 1997; 7:530), using mutant recombination sites (Araki et al., Nucleic Acids Res, 1997; 25:868) or PCR (Zhang and Henderson, Biotechniques, 1998; 25:784).

A "knock-out mammal" is a mammal (e.g., mouse) that contains within its genome a specific gene that has been inactivated by the method of gene targeting (see, e.g., U.S. Pat. Nos. 5,777,195 and 5,616,491). A knockout mammal includes both a heterozygote knockout (i.e., one defective allele and one wild type allele) and a homozygous mutant. Preparation of a knockout mammal requires first introducing a nucleic acid construct that will be used to suppress expression of a particular gene into an undifferentiated cell type termed an embryonic stem cell. This cell is then injected into a mammalian embryo. A mammalian embryo with an integrated cell is then implanted into a foster mother for the duration of gestation. Zhou, et al. (Genes and Development, 1995; 9:2623 34) describes PPCA knock out mice. The term "knockout" refers to partial or complete suppression of the expression of at least a portion of a protein encoded by an endogenous DNA sequence in a cell. The term "knockout construct" refers to a nucleic acid sequence that is designed to decrease or suppress expression of a protein encoded by endogenous DNA sequences in a cell. The nucleic acid sequence used as the knockout construct is typically comprised of (1) DNA from some portion of the gene (exon sequence, intron sequence, and/or promoter sequence) to be suppressed and (2) a marker sequence used to detect the presence of the knockout construct in the cell. The knockout construct is inserted into a cell, and integrates with the genomic DNA of the cell in such a position so as to prevent or interrupt transcription of the native DNA sequence. Such insertion usually occurs by homologous recombination (i.e., regions of the knockout construct that are homologous to endogenous DNA sequences hybridize to each other when the knockout construct is inserted into the cell and recombine so that the knockout construct is incorporated into the corresponding position of the endogenous DNA). The knockout construct nucleic acid sequence may comprise (1) a full or partial sequence of one or more exons and/or introns of the gene to be suppressed, (2) a full or partial promoter sequence of the gene to be suppressed, or (3) combinations thereof. Typically, the knockout construct is inserted into an embryonic stem cell (ES cell) and is integrated into the ES cell genomic DNA, usually by the process of homologous recombination. This ES cell is then injected into, and integrates with, the developing embryo. Generally, for homologous recombination, the DNA will be at least about 1 kilobase (kb) in length and preferably 3-4 kb in length, thereby providing sufficient complementary sequence for recombination when the knockout construct is introduced into the genomic DNA of the ES cell.

Double knock-out mammals can be generated by repeating the procedures set forth herein for generating each knock-in or knock-out construct, or by breeding to mammals, each with a single gene knocked out, to each other, and screening for those with the double knockout genotype. Regulated knockout animals can be prepared using various systems, such as the tet-repressor system (see U.S. Pat. No. 5,654,168) or the Cre-Lox system (see U.S. Pat. No. 4,959,317 and No. 5,801,030). The phrases "disruption of the gene" and "gene disruption" refer to insertion of a nucleic acid sequence into one region of the native DNA sequence (usually one or more exons) and/or the promoter region of a gene so as to decrease or prevent expression of that gene in the cell as compared to the wild type or naturally occurring sequence of the gene. By way of example, a nucleic acid construct can be prepared containing a DNA sequence encoding an antibiotic resistance gene which is inserted into the DNA sequence that is complementary to the DNA sequence (promoter and/or coding region) to be disrupted. When this nucleic acid construct is then transfected into a cell, the construct will integrate into the genomic DNA. Thus, many progeny of the cell will no longer express the gene at least in some cells, or will express it at a decreased level, as the DNA is now disrupted by the antibiotic resistance gene.

In another series of embodiments, transgenic animals are created in which (i) a human Cdc14B and/or Cdh1 is stably inserted into the genome of the transgenic animal; and/or (ii) the corresponding endogenous genes are inactivated and replaced with their human counterparts (see, e.g., Coffman, Semin. Nephrol., 1997; 17:404; Esther et al., Lab. Invest., 1996; 74:953; Murakami et al., Blood Press. Suppl., 1996; 2:36). Such animals can be treated with candidate compounds and monitored for neuronal development, neurodegeneration, or efficacy of a candidate therapeutic compound.

Antibodies to Cdc14B and/or Cdh1

As described in the Examples, various antibodies useful for detecting Plk1, Cdc14B or Cdh1, or any of their substrates, have been produced, some of which are available commercially. Such antibodies may be used in immunoblotting or immunoprecipitation techniques to study binding of Cdc14B or Cdh1 to Plk1 or to another one of its substrates, to detect ubiquitinated Cdc25A, to inhibit interaction between Cdc14B and/or Cdh1 with Plk1, or one of its other substrates, or for other purposes in the screening and treatment methods described herein. Additional antibodies with different specificity or other particular properties may also be prepared. Antibodies useful for these purposes include but are not limited to polyclonal, monoclonal, chimeric, single chain, Fab fragments, and Fab expression library.

Various procedures known in the art may be used for the production of polyclonal antibodies. For example, various host animals can be immunized by injection with the antigenic polypeptide, including but not limited to rabbits, mice, rats, sheep, goats, etc. For preparation of monoclonal antibodies, any technique that provides for the production of antibody molecules by continuous cell lines in culture may be used. These include but are not limited to the hybridoma technique originally developed by Kohler and Milstein (Nature, 1975; 256:495-497), as well as the trioma technique, the human B-cell hybridoma technique (Kozbor et al., Immunology Today, 1983; 4:72, Cote et al., Proc. Natl. Acad. Sci. U.S.A., 1983; 80:2026-2030), and the EBV-hybridoma technique to produce human monoclonal antibodies (Cole et al., in Monoclonal Antibodies and Cancer Therapy, Alan R. Liss, Inc., pp. 77-96, 1985). In an additional embodiment of the invention, monoclonal antibodies can be produced in germ-free animals (International Patent Publication No. WO 89/12690, published 28 December, 1989).

According to the invention, techniques described for the production of single chain antibodies (U.S. Pat. Nos. 5,476, 786 and 5,132,405 to Huston; U.S. Pat. No. 4,946,778) can be adapted to produce polypeptide-specific single chain antibodies. Indeed, these genes can be delivered for expression in vivo to, e.g., express an antibody inhibiting Plk1 interaction with Cdc14B and/or Cdh1. An additional embodiment of the invention utilizes the techniques described for the construction of Fab expression libraries (Huse et al., Science, 1989; 246:1275-1281) to allow rapid and easy identification of monoclonal Fab fragments with the desired specificity for a target polypeptide, or its derivatives, or analogs.

Antibody fragments which contain the idiotype of the antibody molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

Screening

A "test substance" or "test compound" is a chemically defined compound or mixture of compounds (as in the case of a natural extract or tissue culture supernatant), whose ability to modulate Plk1 activity or amount or that modulates the activity or the amount of Cdc14B and/or Cdh1 the a may be defined by various assays. A "test substance" is also referred to as a "candidate drug" or "candidate compound" in the present description.

Test substances may be screened from large libraries of synthetic or natural compounds. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from, e.g., Pan Laboratories (Bothell, Wash.) or MycoSearch (NC), or are readily producible. Additionally, natural and synthetically produced libraries and compounds are readily modified through conventional chemical, physical, and biochemical means (Blondelle et al., TIBTech, 1996; 14:60).

A modulatory effect may be determined by an in vitro method using a recombinant reporter gene promoter activity system including one or more of Plk1, Cdc14B, and Cdh1. Reporter genes for use in the invention encode detectable proteins, and include, but are by no means limited to, chloramphenicol transferase (CAT), β-galactosidase (β-gal), luciferase, green fluorescent protein (GFP) and derivatives thereof, yellow fluorescent protein and derivatives thereof, alkaline phosphatase, other enzymes that can be adapted to produce a detectable product, and other gene products that can be detected, e.g., immunologically (by immunoassay).

A screen according to the invention involves detecting expression of the reporter gene by the host cell when contacted with a test substance. If there is no change in expression of the reporter gene, the test substance is not an effective modulator. If reporter gene expression is modified, the test substance has modulated, e.g., increased Plk1-mediated gene expression, or decreased Cdc14B and/or Cdh1 expression, the test substance is a candidate for development as an agent capable of inducing apoptosis or cell death. Likewise, any such modulator is a candidate for use as a tumor sensitizing agent. Additionally, any such modulator is a candidate for use in combination with another DNA damaging or chemotherapeutic agent to facilitate tumor sensitization leading to cell death. The reporter gene assay system described herein may be used in a high-throughput primary screen for antagonists, or it may be used as a secondary functional screen for candidate compounds identified by a different primary screen, e.g., a binding assay screen that identifies compounds that decrease Cdc14B and/or Cdh1 transcription activity, and/or increase Plk1 activity.

Potential drugs may be identified by screening in high-throughput assays, including without limitation cell-based or cell-free assays. It will be appreciated by those skilled in the art that different types of assays can be used to detect different types of agents. Several methods of automated assays have been developed in recent years so as to permit screening of tens of thousands of compounds in a short period of time (see, e.g., U.S. Pat. Nos. 5,585,277, 5,679,582, and 6,020,141). Such high-throughput screening methods are particularly preferred. Alternatively, simple reporter-gene based cell assays such as the one described here are also highly desirable.

Intact cells or whole animals expressing genes encoding at least one of Plk1, Cdc14B and/or Cdh1, and optionally also any of the remaining components of an SCF complex, can be used in screening methods to identify candidate drugs. In one series of embodiments, a permanent cell line is established. Alternatively, cells are transiently programmed to express a Plk1 gene by introduction of appropriate DNA or mRNA. As described herein, transgenic animals can also be used to screen for or study agents that increase the level of Plk1. Similarly, it may be desirable for cells to be transiently programmed to express any of the genes encoding Cdc14B and/or Cdh1 by introduction of appropriate DNA or mRNA. As described herein, transgenic animals can also be used to screen for or study agents that increase the level of Cdc14B and/or Cdh1.

Identification of candidate substances can be achieved using any suitable assay, including without limitation (i) assays that measure selective binding of test compounds to Plk1, to the Plk1 binding site on Cdc14B and/or Cdh1, or another one of its substrates (ii) assays that measure the ability of a test substance to modify (e.g., inhibit) a measurable activity or function of Cdc14B and/or Cdh1, (iii) assays that measure the ability of a substance to modify (i.e., inhibit) the transcriptional activity of sequences derived from the promoter (i.e., regulatory) regions of at least one of the genes encoding Cdc14B and/or Cdh1; and (iv) assays that modulate (e.g., promote) the degradation of at least Cdc14B and/or Cdh1 proteins, while increasing the level of Plk1.

Selected agents may be modified to enhance efficacy, stability, pharmaceutical compatibility, and the like. Structural identification of an agent may be used to identify, generate, or screen additional agents. For example, where peptide agents are identified, they may be modified in a variety of ways, e.g. to enhance their proteolytic stability.

RNA Interference (RNAi or siRNA)

Another technique of interest for therapeutic purposes is based on the same principles employed for interfering with Cdc14B and/or Cdh1 translation in a cellular system, namely siRNA technology. Particularly, expression of selected genes can be suppressed in human cells by transfecting with exogenous, short RNA duplexes (siRNA) where one strand corresponds to a target region of the mRNA, i.e., EST of interest (Elbashir et al., Nature, 2001; 411:494-498). The siRNA molecules are typically greater than 19 duplex nucleotides, and upon entry into the cell, siRNA causes the degradation of single-stranded (ssRNAs) RNAs of identical sequences, including endogenous mRNAs. siRNA is more potent than standard anti-sense technology since it acts through a catalytic mechanism. Effective strategies to deliver siRNAs to target cells in cell culture include physical or chemical transfection. An alternative strategy uses the endogenous expression of siRNAs by various Pol III promoter expression cassettes that allow transcription of functional siRNAs or their precursors (Scherr et al., Curr. Med. Chem., 2003; 10(3):245-56). Recently, the RNA-polymerase III dependent promoter (H1-RNA promoter) was inserted in the lentiviral genome to drive the expression of a small hairpin RNA (shRNA) against enhanced green fluorescent protein (Abbas-Turki et al., Hum. Gene Ther., 2002; 13(18):2197-201). siRNA can also be delivered in a viral vector derived, e.g., from a lentivirus (Tiscornia et al., Proc. Natl. Acad. Sci. U.S.A., 2003; 100: 1844-8). For review articles, see Hannon, Nature, 2002; 418: 244-51 and Bernstein et al., RNA, 2001; 7(11):1509-21. This technology also has been described in vitro in cultured mammalian neurons in Krickevsky and Kosik, Proc. Natl. Acad. Sci. USA, 2002; 99(18):11926-9. siRNA technology is also being used to make transgenic animals (Cornell et al., Nat. Struct. Biol., 2003; 10(2):91-2). RNAi is described in Publication Nos. WO 99/49029 and WO 01/70949.

Exemplary siRNA's suitable for 13-TrCP1/2, Plk1, Cdc14B, or Cdh1 include:

```
for human β-TrCP1/2:
                                    (SEQ ID NO: 19)
GUGGAAUUUGUGGAACAUC for mouse β-TrCP1/2:
                                    (SEQ ID NO: 20)
AUCAAGAUCAGGGAUAAAA
``` for human Cdc14B (SEQ ID NO:22)
for human Cdh1: (SEQ ID NO:21).

Materials & Methods

The following describes the materials and methods employed in Examples 1-6.

Cells

HeLa (human carcinoma; obtained from ATCC) or U2OS (human osteosarcoma) cells are used in certain of the Examples. Cell culture is conducted essentially as described in Donzelli et al. (Embo J, 2002; 21:4875-84). Cells are grown at 37° C. in a 5% $CO_2$ atmosphere in Dulbecco's modified Eagle's medium (Euroclone) supplemented with 10% bovine calf serum (Hyclone) and 2 mM L-glutamine (Euroclone), or in DMEM containing 5% FCS.

Cell Synchronization and Drug Treatments

U2OS and T98G cells were synchronized as described (Dorrello et al., 2006; Peschiaroli et al., 2006). Pulse treatment of U2OS cells with doxorubicin was performed for one hour at a final concentration of 0.5 µM. To measure protein half-lives, G2 cells were incubated in the presence of 100 µg/ml cycloheximide dissolved in 100% ethanol.

Cell Culture

U2OS, HeLa, HeLa-S3, T98G, and HEK293T cells were cultured as described (Dorrello et al., 2006; Guardavaccaro et al., 2003). ATM+/+ (NHF1-hTERT) and ATM−/− (GM0252A-hTERT) fibroblasts were grown as described by (Heffernan et al., 2002).

Antibodies

Mouse monoclonal antibodies were from Zymed/Invitrogen (anti-Cul1, anti-Plk1), Sigma (anti-FLAG, anti-Cdc27, anti-Cdh1), Santa Cruz Biotechnology (anti-Chk1, anti-Geminin, anti-Cdc25A), Boston Biochem (anti-UbCH10), BD Biosciences (anti-p27), Covance (anti-HA), and Abcam (anti-GFP). The mouse monoclonal antibodies against Claspin and USP28 were kind gifts from Thannos Halazonetis and Steve Elledge. Rabbit polyclonal antibodies were from Zymed/Invitrogen (anti-Cks1), Upstate (anti-phospho-Ser10 Histone H3, anti-phospho-Ser 139 Histone H2AX), Santa Cruz Biotechnology (anti-Wee1, Cdk2, phospho-Tyr15 Cdk1, Skp1, Bub1), and Cell Signaling (phospho-Ser317 Chk1, phospho-Thr68 Chk2). The rabbit polyclonal antibodies against TMPK and TK1 were a kind gift from Zee-Fen Chang. Rabbit polyclonal antibodies against Cdk1 (Carrano et al., 1999), cyclin A (Carrano and Pagano, 2001), and the mouse monoclonal antibody to cyclin E (Faha et al., 1993) were previously described.

In Vitro Ubiquitylation Assay

Ubiquitylation assays were previously described (Bashir et al., 2004). Briefly, an anti-Cdc27 antibody was added to cell extracts and incubated for approximately 3 hours at 4° C. Protein G-agarose was then added and incubated for 45 minutes at 4° C. on a rotating wheel. The beads were washed 4 times in Triton buffer and 4 times in QA buffer (10 mM Tris-HCl pH 7.5, 100 mM KCl, 1 mM MgCl$_2$, 0.1 mM CaCl$_2$, 1 mM DTT). The resulting beads were used for two reactions of in vitro ubiquitylation. Ubiquitylation assays were performed in a volume of 10 µl containing 50 mM Tris pH 7.6, 5 mM MgCl2, 0.6 mM DTT, 2 mM ATP, 2 µl in vitro transcribed/translated unlabelled Cdh1, 50 ng/µl E1 (Boston Biochem), 100 ng/µl Ubc1, 100 ng/µl Ubc10, 2.5 µg/µl ubiquitin (Sigma), 1 µM ubiquitin aldehyde, and 1 µl $^{35}$S-methionine-labelled in vitro transcribed/translated substrate [i.e. wild type NT-Claspin, NT-Claspin (ENL), CT-Claspin, Plk1, or cyclin B labeled in vitro transcribed/translated in rabbit reticulocyte lysate (RRL)]. The reactions were incubated at 30° C. for the indicated times and analyzed by SDS-PAGE and autoradiography. The RRLs containing the in vitro transcribed/translated substrates were treated with 5 mM NEM prior to ubiquitylation reactions, which transitorily inactivates ubiquitylating activities present in the RRL (Rodrigo-Brenni and Morgan, 2007). The assays shown in FIG. S4D did not contain Cdh1.

GST Fusion Proteins and Pull-Down Assay

GST-Cdh1 or GST-Claspin mutants were expressed in *E. coli* (BL-21) using the pGEX 4T2 vector (Amersham). For protein purification, bacteria were grown to an optical density of 600 nm in Luria-Bertani medium, induced at 37° C. with 0.1 mM isopropyl-1-thio-D-galactopyranoside, and cultivated for 2 h. Bacteria were then pelleted, resuspended in NETN-buffer (100 mM NaCl, 1 mM EDTA, 50 mM Tris.HCl [pH 7.4], 0.5% Nonidet P-40, 1 mM phenylmethylsulfonyl fluoride, 5 mM benzamidine), and sonicated. Insoluble material was removed by centrifugation. Thirty microliters of Glutathione-S-Sepharose 4b beads (Amersham) were added to the cleared lysate, incubated for 30 min at 4° C., and washed 3 times with NETN-buffer. GST pull-down assays were performed as described previously (Bassermann et al., 2005). Briefly, wild type and mutant Claspin proteins or Cdh1 were in vitro transcribed/translated and $^{35}$S-radiolabeled using the TNT system (Promega). GST fusion proteins were added and incubated for one hour at 4° C. Subsequently, protein complexes were washed thoroughly with NETN buffer, subjected to SDS-PAGE, and visualized by autoradiography.

Plasmids cDNAs of wild type Claspin, Claspin point- and deletion-mutants, βTrcp1/2, Fbxw4, Fbxw5, Fbxw6, Fbxw7, Cdh1, and Cdc20 were cloned into pcDNA 3.1. pGFP-Cdc14A and pGFP-Cdc14B were kind gifts from Jiri Lukas. For retrovirus production, Cdc14B, Cdh1 WT, and Cdh1 (4xA) were subcloned into the retroviral vector pMSCV while Plk1 WT and Plk1 (R337A, L340A) were subcloned into the retroviral vector pBabe. All cDNAs were sequenced. Point mutants were generated using the QuikChange Site-directed Mutagenesis kit (Stratagene), and deletion mutants were prepared by standard PCR procedures.

siRNA oligos

The sequences of the oligonucleotides corresponding to βTrcp1/βTrcp2, Cdh1, Cdc14B, and Usp28 mRNAs were GUGGAAUUUGUGGAACAUC (SEQ ID NO:20), UGAGAAGUCUCCCAGUCAG (SEQ ID NO:21), GAUGCUACAUGGUUAUAUA (SEQ ID NO: 22), and CUGCAUUCACCUUAUCAUU (SEQ ID NO:23), respectively. These dsRNA oligos have been previously validated: Cdh1 (Bashir et al., 2004; Brummelkamp et al., 2002; Donzelli et al., 2002; Ke and Chang, 2004), Usp28 (Zhang et al., 2006), βTrCP1/2 (Dorrello et al., 2006; Fong and Sun, 2002; Guardavaccaro, 2008; Guardavaccaro et al., 2003; Jin et al., 2003; Peschiaroli et al., 2006) and Cdc14B (Rodier et al., 2008). A dsRNA oligo to LacZ mRNA (CGUACGCGGAAUACUUCGA) (SEQ ID NO: 24) served as control.

mRNA Analysis

RNA was extracted using the RNeasy Kit (Qiagen). cDNA synthesis was performed using Superscript III (Invitrogen). Quantitative PCR analysis was performed according to standard procedures. Primer sequences were:

```
                                        (SEQ ID NO: 25)
5'GTGCCATTGCAGTACATT3'
and (SEQ ID NO: 26)
5'AGCAGGCTATCAGAGTG3'
(Cdc14B) and (SEQ ID NO: 27)
5'CGCCGCTAGAGGTGAAATTC3'
and (SEQ ID NO: 28)
5'CTTTCGCTCTGGTCCGTCTT3'.
(18S rRNA)
```

Immunofluorescence Microscopy

Direct and indirect immunofluorescence was performed as described (Frescas et al., 2007). Primary antibodies (anti-FLAG, Sigma; anti-GFP, Abcam) were used at a dilution of 1:1000.

In Vivo Labeling with Orthophosphate

U2OS cells expressing either wild type Cdh1 or Cdh1 (4xA) were transfected with control or Cdc14B siRNA oligonucleotides and synchronized at G1/S using a double thymidine block. Seven hours post release, cells were washed twice in labeling medium [(phosphate-free DMEM, supplemented with 10% dialyzed serum (Hyclone)] and subsequently incubated for three hours in labeling medium, containing 0.5 µM doxorubicine and [$^{32}$P]-orthophosphate (0.5 mCi/ml, Perkin Elmer). Denatured cell extracts were subsequently prepared in 1% SDS. Prior to immunoprecipitation with anti-FLAG agarose (Sigma), cell extracts were diluted 10-fold with lysis buffer containing 1% Triton X-100.

Data Mining

Gene expression data on Cdc14B, Cdh1 and Plk1 were retrieved from the Oncomine website. Data was re-analyzed in GraphPad software to show expression levels of Cdc14B, Cdh1, and Plk1 for each cancer study. GraphPad software was used to determine P values. Additional details relating to these studies, including the pathological and clinical data, are available at Oncomine or via the individual journal websites. Kaplan-Meier survival curves of 219 brain cancer patients were obtained from the Repository of Molecular Brain Neoplasia Database Rembrandt website of the National Cancer Institute at NIH. Kaplan-Meier survival plots were generated by grouping gliomas of all histological grades by the gene expression levels of Cdc14B, Cdh1 and Plk1. Additional details relating to these studies, including the pathological and clinical data of individual patients, are available on the Rembrandt website.

Normalization and Quantification of Protein Levels

Protein concentrations of whole cell extracts (WCE) were performed using a Bio-Rad DC protein assay (Lowry assay) according to the manufacturers instructions. For each experiment, equal amounts of WCE (in general, 30 µg) were separated by SDS-PAGE and then analyzed by immunoblotting. Equal protein levels in each lane were confirmed by Ponceau S staining of the membrane and by immunoblotting a protein whose levels are not regulated by either DNA damage or during cell cycle progression (e.g., Cul1 or Skp1). To make the assay as linear as possible, densitometric quantification of bands was performed using Quantity One software (Bio-Rad) on low-saturation exposures. To be able to directly compare protein levels of different gels and independent experiments, an equal WCE (e.g., 30 μg of HeLa WCE) was loaded in each gel as a standard reference.

EXAMPLES

The following examples are included to demonstrate certain embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Claspin is a Substrate of APC/C$^{Cdh1}$ in the G1 Phase of the Cell Cycle.

It was previously known that the levels of Claspin oscillate throughout the cell cycle (Mailand et al., 2006; Mamely et al., 2006; Peschiaroli et al., 2006). The highest Claspin expression levels are observed in S phase and early G2, and levels decrease thereafter, becoming almost undetectable during mitosis and the following G1 phase, as shown in FIGS. 1A-E. In FIG. 1A U2OS cells were released from a prometaphase arrest (indicated as time 0) and collected at the indicated times. Protein extracts were analyzed by immunoblotting with antibodies to the indicated proteins. (AS, asynchronous cells). FIG. 1B shows cell cycle profiles of the cells used in the experiment shown in FIG. 1A as determined by flow cytometry.

For the experiments shown in FIG. 1C, T98G cells were switched to culture media containing 0.02% FBS to arrest them in G0/G1. Samples were collected at the indicated times after the beginning of the serum starvation and subjected to immunoblot analysis using antibodies to the indicated proteins. FIG. 1D shows cell cycle profiles of the cells used in the experiment shown in FIG. 1C as determined by flow cytometry.

In FIG. 1E U2OS cells were transfected with siRNA oligos to both βTrcp1 and βTrcp2 mRNAs. Cells were collected after being synchronized in prometaphase (PM) or G1 phase, and cell extracts were analyzed by immunoblotting with antibodies to the indicated proteins.

Levels of Claspin also decrease when cells withdraw from the cell cycle and enter quiescence (FIG. 1B). Since SCF$^{βTrcp}$ mediates the degradation of Claspin degradation at G2/M, experiments were designed to determine whether this ligase is also responsible for Claspin degradation in G1. Both βTrcp1 and βTrcp2 were downregulated using an established siRNA oligo and Claspin levels in both M and G1 were analyzed.

While silencing of βTrcp induced an accumulation of Claspin in prometaphase cells, no effect was visible in G1 cells (FIG. 1E), suggesting that a different ligase from SCF$^{βTrcp}$ targets Claspin for degradation in G0 and G1. Thus, experiments were designed to identify the uncharacterized G1 specific ubiquitin ligase by investigating the ability of Claspin to bind ubiquitin ligase subunits. The data showed that only Cdh1 was able to co-immunoprecipitate endogenous Claspin, whereas Fbxw4, Fbxw5, Fbxw6, Fbxw7, and Cdc20 (FIG. 2A), as well as thirteen different F-box proteins (Peschiaroli et al., 2006), failed to bind Claspin.

To test whether APC/C$^{Cdh1}$ has a role in the degradation of Claspin during G0/G1, the expression of Cdh1 was reduced in T98G cells using a validated is RNA (SEQ ID NO:21). T98G cells were serum starved following knockdown of Cdh1, and the expression levels of Claspin were analyzed at various time points thereafter. FIGS. 2A-D are immunoblots showing Claspin is degraded in G0 and G1 via the APC/C$^{Cdh1}$ ubiquitin ligase. FIG. 2A shows that Cdh1 interacts with Claspin in vivo. HEK293T cells were transfected with the indicated FLAG-tagged constructs or an empty vector (EV). Whole cell extracts (WCE) were immunoprecipitated (IP) with anti-FLAG resin, and immunocomplexes were probed with antibodies to the indicated proteins.

FIG. 2B shows T98G cells were transfected with a control (Ctrl) siRNA oligo or an siRNA oligo directed against Cdh1 mRNA. Cells were then switched to culture media containing 0.02% FBS to arrest them in G0/G1. Samples were collected at the indicated times after the beginning of the serum starvation and subjected to immunoblot analysis using antibodies to the indicated proteins. Skp2 and p27 were used as cell cycle markers.

FIG. 2C shows Claspin (ENL) is stable in G1. HeLa cells were infected with retroviruses expressing either FLAG-tagged wild type Claspin or FLAG-tagged Claspin (ENL) and subsequently treated for 16 hours with nocodazole to induce a mitotic block. Round, prometaphase cells were then collected by gentle shake-off and replated in fresh medium for the indicated times. Cells were harvested, and cell extracts were analyzed by immunoblotting with antibodies to the indicated proteins. Synchronization was monitored by flow cytometry and by the levels of cyclin B.

FIG. 2D shows Ubiquitin ligation assays of $^{35}$S-labeled, in vitro translated Claspin N-terminal fragments (amino acid 1-678) of either wild type Claspin or Claspin (ENL) were conducted in the presence of unlabeled, in vitro translated Cdh1. Samples were incubated at 30° C. for the indicated times. The lower autoradiography image represents a short exposure time, and the upper image represents a long exposure time. The bracket on the right side of the top panel marks a ladder of bands corresponding to polyubiquitylated Claspin.

These experiments illustrated that downregulation of Cdh1 strongly inhibited the degradation of Claspin in cells progressively accumulating in G0/G1 (FIG. 2B). Similarly, T98G cells released from a block in prometaphase retained Claspin expression throughout G1 phase upon silencing of Cdh1. Together, these data show a role for APC/C$^{Cdh1}$ in targeting Claspin for degradation during G0 and G1.

The Cdh1 binding motif of Claspin was systematically mapped. In FIG. 3A the indicated deletion mutants were transcribed/translated in vitro and tested for their binding to GST-tagged Cdh1 using in vitro pull-down assays. Claspin mutants that were pulled-down by GST-Cdh1 were separated by SDS-PAGE and visualized by autoradiography and designated with the symbol (+).

In FIG. 3B HEK293T cells were co-transfected with HA-tagged Cdh1 and the indicated FLAG-tagged deletion mutants of Claspin. Whole cell extracts (WCE, bottom panel) were immunoprecipitated (IP, upper two panels) with an anti-HA antibody, and the indicated proteins were detected by immunoblotting. FIG. 3C shows a schematic representation of the in vivo binding data shown in FIG. 3B.

In FIG. 3D in vitro transcribed/translated, $^{35}$S-labeled Cdh1 was assayed for in vitro binding to the indicated GST-tagged Claspin fragments. Bound Cdh1 was separated by SDS-PAGE and visualized by autoradiography. This series of binding experiments using multiple Claspin deletion mutants narrowed the binding motif to an N-terminal region located between amino acids 79-102 of SEQ ID NO:9 (FIGS. 3A-D).

FIG. 3E shows CLUSTALW alignment of Claspin orthologs with shading of conserved amino acids. Dark gray: identical residues; light gray: similar residues. Five groups of three amino acids mutated individually in Claspin are framed.

HEK293T cells were cotransfected with HA-tagged Cdh1 and the indicated FLAG-tagged Claspin mutants. Whole cell extracts (WCE, bottom two panels, FIG. 3B) were immunoprecipitated (IP, upper two panels FIG. 3B) with an anti-HA antibody, and the indicated proteins were detected by immunoblotting. Finally, five unique, triple-point-mutations to Alanine across Claspin amino acids 79-102 were inserted, following the pattern of evolutionary conserved residues (FIG. 3E), and these mutants were assayed for binding to Cdh1. The immunoblots are shown in FIG. 3F. Both mutant #2 [Claspin (EEN)] and mutant #3 [Claspin (ENL)] failed to bind Cdh1 (FIG. 3F). Thus, these studies identified the motif "EENxENL" (SEQ ID NO:29) located at residues 86-92 of Claspin (SEQ ID NO: 9), as the site mediating binding to Cdh1. Accordingly, in contrast to wild type Claspin, Claspin (ENL) was stable in HeLa cells progressing through G1 (FIG. 2C).

These data show that the Cdh1-binding site in Claspin is not a canonical degron for APC/C substrates (i.e. D-box or KEN box motifs). Non-standard degrons have also been described for Aurora A (the A-box) (Littlepage and Ruderman, 2002) and Orc1 (the O-box) (Araki et al., 2005).

To further illustrate that Claspin is ubiquitylated via APC/$C^{Cdh1}$, the ubiquitylation of Claspin was reconstituted in vitro. The N-terminus of Claspin (amino acids 1-678 of SEQ ID NO:9) was efficiently ubiquitylated only when Cdh1 was present (FIG. 2D and FIGS. 4A-B). FIGS. 4A-B show that the N-terminus of claspin is ubiquitylated in a Cdh1-dependent manner. FIG. 4A shows in vitro ubiquitin ligation assays with $^{35}$S-labeled, in vitro transcribed/translated Claspin N-terminus (NT, amino acids 1-678). FIG. 4B shows cyclin B (as a positive control) in vitro ubiquitin ligation assays conducted in the presence or absence of Cdh1 using different UBCs. Samples were incubated at 30° C. and analyzed at the indicated times. The bracket on the right side marks a ladder of bands corresponding to polyubiquitylated proteins. These experiments show that the ubiquitylation of Claspin is dependent on the presence of Cdh1 and is stimulated by Ubc1 (also called E2-25K), which promotes ubiquitylation of APC/$C^{Cdh1}$ substrates by Ubc10. Ubiquitylation of APC/$C^{Cdh1}$ substrates by Ubc10 is described by Rodrigo-Brenni and Morgan, 2007.

In contrast, no Cdh1-dependent ubiquitylation of Claspin (ENL) was observed (FIG. 2D). Similarly, the C-terminus of Claspin (amino acids 679-1333 of SEQ ID NO:9), lacking the Cdh1-binding domain, was not ubiquitylated despite the presence of Cdh1.

Thus, experiments in cell systems including an in vivo model system, and in an in vitro reconstituted model, show that Cdh1 promotes the ubiquitylation and consequent degradation of Claspin in a manner that requires an intact Cdh1-interaction motif.

Example 2

Upon DNA damage in G2, Usp28 protects Claspin, but not Plk1, from APC/$C^{Cdh1}$-mediated degradation Usp28 deubiquitylates and consequently stabilizes Claspin in response to DNA damage (Zhang et al., 2006). After genotoxic stress, the recognition of Claspin by the SCF$^{\beta Trcp}$ ubiquitin ligase is impaired due to the inhibition of Plk1 (Mailand et al., 2006; Mamely et al., 2006; Peschiaroli et al., 2006; Smits et al., 2000). Under these conditions, Claspin is continuously ubiquitylated via an unidentified ubiquitin ligase that is different from SCF$^{\beta Trcp}$. A G2 phase-specific reactivation of APC/$C^{Cdh1}$ after DNA damage has been described in vertebrates (Sudo et al., 2001), but the reason for this reactivation is not known. The present experiments confirm that Cdh1 re-associates with Cdc27 (an APC/C core subunit) in human G2 cells subjected to genotoxic stresses, and that this APC/$C^{Cdh1}$ is active (FIGS. 5A-I).

FIG. 5A shows results after HeLa-S3 cells were synchronized at G1/S using a double thymidine block and then released to allow progression towards G2. At four hours post-release, cells were either left untreated or irradiated (IR) with 10 Gy before harvesting two hours thereafter. Subsequently, whole cell extracts (FIG. 5B, WCE) were immunoprecipitated (IP) with either a mouse anti-Cdh1 antibody or purified, non-specific mouse immunoglobulins (NS IgG), and the indicated proteins were analyzed by immunoblotting. DNA content analyses by FACS (FIGS. 5C, D, and E) were performed to ascertain equal cell cycle distribution of the two samples.

FIG. 5F shows immunoblots after U2OS cells were synchronized at G1/S and then released to allow progression towards G2. At seven hours post-release, cells were pulsed for one hour with either solvent (–) or doxorubicin (DRB) (+) and harvested two hours thereafter. Whole cell extracts (WCE) were immunoprecipitated with a monoclonal anti-Cdc27 antibody or non-specific, purified mouse immunoglobulins (NS IgG). Immunoprecipitates and extracts were immunoblotted with either anti-Cdh1 or anti-Cdc27 antibodies.

FIG. 5G shows results after U2OS cells infected with either an empty virus (EV) or retroviruses expressing FLAG-tagged Cdh1 were synchronized at G1/S and released as in FIG. 5F. At seven hours post-release, cells were pulsed for one hour with either solvent or doxorubicin (DRB) and then harvested at the indicated times. Subsequently, whole cell extracts (WCE) were immunoprecipitated (IP) with anti-FLAG resin, and the indicated proteins were analyzed by immunoblotting. DNA content analyses measured by FACS as shown in FIG. 5I and show the cell cycle distribution of the samples.

FIG. 5H shows results after HeLa-S3 cells were synchronized at G1/S using a double thymidine block and then released to allow progression towards G2. At seven hours post release, cells were either left untreated or irradiated (IR) with 10 Gy before harvesting two hours thereafter. Subsequently, cell extracts were immunoprecipitated with an anti-Cdc27 antibody, and immunoprecipitates were used for in vitro ubiquitylation assays using in vitro transcribed/translated Plk1 as a substrate. Note that this ubiquitylation reaction relied only on the presence of Cdh1 co-immunoprecipitated with Cdc27 (i.e. in the absence of in vitro transcribed/translated unlabelled Cdh1, as in all other ubiquitylation assays shown herein) to allow a direct comparison of endogenous APC/$C^{Cdh1}$ under the two different conditions.

In line with these results, experiments were designed to investigate whether APC/$C^{Cdh1}$ targets Claspin during G2 in response to DNA damage, which would explain the need for Usp28. In these experiments, the expression of Cdh1, Usp28, or both Cdh1 and Usp28 were silenced in U2OS cells using previously validated siRNA oligos (SEQ ID NO:21, SEQ ID NO:23). After transfection, cells were synchronized at G1/S and then allowed to progress through the cell cycle. Seven hours after the release from G1/S (when cells were in G2), cells were pulsed with doxorubicin for one hour to induce DNA damage and harvested at different times thereafter (FIGS. 6A-E). The results showed that downregulation of Usp28 resulted in decreased levels of Claspin (FIG. 6A, lanes 14 and 15). However, when both Usp28 and Cdh1 were silenced together, the expression of Claspin was partially restored (FIG. 6A, lanes 19 and 20), indicating that Usp28 counteracts Cdh1-dependent degradation of Claspin.

The immunoblots in FIG. 6A show extracts of U2OS cells that were transfected with the indicated siRNA oligos and synchronized at G1/S using a double thymidine block. Cells were then released from the block to allow progression towards G2. At seven hours post release, cells were pulsed for one hour with either solvent (−) or doxorubicin (DRB) (+) and collected at the indicated times thereafter. Whole cell extracts were analyzed by immunoblotting with antibodies to the indicated proteins. Synchrony was verified by flow cytometry. To facilitate comparison, a gray line separates samples treated with doxorubicin from untreated samples.

The graphs in FIGS. 6B, C, and D show the quantification of the levels of Claspin, Plk1, and Chk1 phosphorylated on Ser317 shown in (FIG. 6A) at the 10 hour timepoint averaged with two additional, independent experiments. The value given for the amount of protein present in the control sample two hours after the end of the doxorubicin pulse was set as 1 (n=3, ±SD).

The immunoblots in FIG. 6E show extracts of U2OS cells that were synchronized and treated with DRB as described in FIG. 6A. Samples were collected at the indicated times and processed for immunoblot analysis with antibodies to the indicated proteins.

To determine if Claspin is protected from proteolysis by Usp28 in DNA-damaged G2 cells, experiments were designed to determine what substrates are targeted for degradation by APC/C$^{Cdh1}$. In these experiments, the levels of 15 G1 substrates of Cdh1 (Claspin, Plk1, Cdc25A, Ubc10, cyclin A, cyclin B, Cdc6, Aurora A, Geminin, Tk1, Tmpk, Skp2, Cks1, Cdc20, and Bub1) were analyzed. U2OS cells were synchronized in G2 and pulsed with doxorubicin, as described for FIG. 6A. Samples were collected at different times thereafter and subjected to immunoblotting. The levels of Plk1 decreased in response to DNA damage (FIG. 6E) in a manner similar to Cdc25A, whose degradation after genotoxic stresses is dependent on SCF$^{\beta Trcp}$ (Busino et al., 2003; Jin et al., 2003). The other 13 substrates of APC/C$^{Cdh1}$ remained unchanged or showed slight increases in their abundance (FIG. 6E).

Next, it was determined whether Plk1 degradation is dependent on the reactivated APC/C$^{Cdh1}$ complex. These resulted showed that levels of Plk1 were considerably reduced in the presence of doxorubicin at the 10-hour time point compared to the untreated sample (compare lane 3 to lane 5 in FIG. 6A). In contrast, when cells were treated with Cdh1 siRNA oligos (SEQ ID NO:21), Plk1 levels remained unchanged despite the presence of DNA damage (compare lane 3 to lanes 10 and 20 in FIG. 6A). Downregulation of Usp28 did not affect Plk1 levels or Plk1 half-life (FIG. 6A and FIG. 7A), indicating that Usp28 does not oppose ubiquitylation of Plk1 as it does with Claspin.

FIGS. 7A-C show Usp28 downregulation destabilizes Claspin but not Plk1. U2OS cells were transfected with the indicated siRNA oligos and synchronized at G1/S using a double thymidine block. Cells were then released from the block to allow progression towards G2. Seven hours post release, doxorubicin (DRB) (+) and cycloheximide (CHX) were added to the cells, which were collected at the indicated times thereafter. Cell lysates were then immunoblotted with antibodies to the indicated proteins. FIG. 7B-C show the quantification of the levels of Plk1 and Claspin shown in FIG. 7A.

FIG. 7D shows downregulation of either Cdh1 or Cdc14B results in the stabilization of Plk1 and in the destabilization of Claspin in DNA damaged cells. U2OS cells were transfected with the indicated siRNA oligos and synchronized at G1/S using a double thymidine block. Cells were then released from the block to allow progression towards G2. Seven hours post-release, cells were pulsed for one hour with either solvent (−) or doxorubicin (DRB) (+). Sixteen hours later, cycloheximide (CHX) was added to the culture for the indicated times prior to harvesting. Cell lysates were then immunoblotted with antibodies to the indicated proteins. FIG. 7E-F show the quantification of the levels of Plk1 and Claspin shown in top panels. FIG. 7G shows Cdc14B mRNA levels of cells used in top panels (FIGS. 7D-E) were analyzed at the "0 hrs" time point using real time PCR in triplicate measurements (±SD). The value given for the amount of Cdc14B mRNA present in cells treated with control oligos was set as 1.

FIG. 7H shows Expression of Cdh1 (4×A) does not allow Plk1 stabilization after DNA damage, despite the downregulation of Cdc14B. U2OS cells were retrovirally infected with either wild type Cdh1 or Cdh1 (4×A) mutant and subsequently transfected with siRNA oligos directed against Cdc14B mRNA. Cells were synchronized at G1/S using a double thymidine block and then released from the block to allow progression towards G2. Seven hours post release, cells were pulsed for one hour with either solvent (−) or doxorubicin (DRB) (+). Sixteen hours later, cycloheximide (CHX) was added to the culture for the indicated times prior to harvesting. Cell lysates were then immunoblotted with antibodies to the indicated proteins.

FIG. 7 I-J show the quantification of the levels of Plk1 and Claspin shown in top panels (FIG. 7H). FIG. 7K shows Cdc14B mRNA levels of cells used in top panels analyzed at the "0 hrs" time point using real time PCR in triplicate measurements (±SD). The value given for the amount of Cdc14B mRNA present in the sample expressing wild type Cdh1 and treated with control oligos was set as 1.

Knockdown of Cdh1 and/or Usp28 had no effect on Cdc25A (FIG. 6A). Interestingly compared to samples treated with control oligos, downregulation of Cdh1 induced a reduction in the levels of Claspin and in the activating phosphorylation of Chk1 on Ser317 (FIGS. 6A, B). This last result shows that APC/C$^{Cdh1}$ activity is necessary to sustain Claspin expression in response to genotoxic stress in G2. Since Plk1 promotes Claspin degradation, the stabilization of Plk1, which occurred in cells where Cdh1 expression was silenced, may explain why Claspin levels decrease under these conditions.

The above results show that APC/C$^{Cdh1}$ targets Claspin and Plk1 in response to DNA damage in G2 and that Usp28 selectively counteracts this action on Claspin. In addition, these results suggest that the APC/C$^{Cdh1}$-mediated degradation of Plk1 promotes Claspin stabilization and the consequent activation of Chk1.

Example 3

Cdh1-Dependent Degradation of Plk1 is Required for an Efficient DNA Damage-Induced G2 Checkpoint A destruction box in Plk1 is required for the APC/C$^{Cdh1}$-dependent degradation of Plk1 during late M and in G1 (Lindon and Pines, 2004). A stable Plk1 mutant [Plk1 (R337A, L340A)] was generated to investigate the biological function of Plk1 degradation in response to DNA damage in G2. U2OS cells were retrovirally infected with either wild type Plk1 or Plk1 (Plk1 R337A, L340A) (i.e., the mutant Plk1) were synchronized in G2, pulsed for one hour with doxorubicin, and followed for an additional three hour period. These results showed that Plk1 (R337A,L340A) was not degraded following treatment with doxorubicin, whereas a significant decrease in the levels of wild type Plk1 was observed (FIGS. 8A, B, C, and D). The difference in Plk1 levels corresponded to the difference in the half-lives of wild type Plk1 versus Plk1 (R337A,L340A) (FIG. 8E, F). This finding shows that DNA damage-induced degradation of Plk1 in G2 is mediated by its Cdh1-binding site.

U2OS cells retrovirally infected with the indicated Plk1 constructs were synchronized and treated with DRB as described in FIG. 6A. Cells were then collected at the indicated times and immunoblotted with antibodies to the indicated proteins. To facilitate comparison, a gray line separates samples treated with doxorubicin from untreated samples. The immunoblots are shown in FIG. 8A.

The graphs in FIG. 8B-D show the quantification of the levels of Claspin, Plk1, and Chk1 phosphorylated on Ser317 shown in FIG. 8A at the 10 hour timepoint averaged with an additional, independent experiment. The value given for the amount of protein present in the control sample two hours after the end of the doxorubicin pulse was set as 1 (n=2).

U2OS cells were infected, synchronized, and pulsed with doxorubicin as in FIG. 8A, except that cycloheximide (CHX) was added seven hours after release from G1/S. At different times after the addition of CHX, cells were collected, and cell lysates were immunoblotted with antibodies to the indicated proteins. The immunoblots are shown in FIG. 8E.

The graph in FIG. 8F shows the quantification of the levels of wild type Plk1 and Plk1 (R337A, L340A) shown in FIG. 8E averaged with two additional, independent experiments (n=3, ±SD).

U2OS cells infected with either an empty virus (EV) or retroviruses encoding wild type Plk1, Plk1 (R337A, L340A), or Cdc25A (S82A) were synchronized and treated with DRB as described in FIG. 8A. Thereafter, cells were incubated in fresh medium containing nocodazole to trap cells in mitosis. Samples were then collected at the indicated times, and the percentage of mitotic cells was monitored by immunodetection of Histone H3 phosphorylated on Ser10 using flow cytometry (n=3, ±SD). The graph of the flow cytometric results is shown in FIG. 8G.

U2OS cells treated as in (FIG. 8A) were collected 23 hours after release from G1/S (16 hours after the doxorubicin pulse), and then cell lysates were immunoblotted with antibodies to the indicated proteins. The immunoblots are shown in FIG. 8H.

Following DNA damage, the lack of Plk1 (R337A, L340A) degradation was associated with decreased levels of Claspin and reduced phosphorylation of Chk1 (FIGS. 3A, B), similar to what is observed when Cdh1 is silenced (FIGS. 6A, B). Since Plk1 initiates the SCF$^{\beta Trcp}$-dependent degradation of Claspin following recovery from DNA damage stresses, these data argue for a role of Cdh1 in limiting Plk1 levels to preserve Claspin stability and Chk1 activation in response to DNA damage in G2.

To investigate the impact of stable Plk1 on the maintenance of the checkpoint, U2OS cells treated as in FIG. 8A were incubated with nocodazole (to trap cells in mitosis) and followed for longer time points (up to 31 hours after release from G1/S, i.e. 24 hours after the pulse with doxorubicin) (FIG. 8G). In addition to cells expressing wild type Plk1 or Plk1 (R337A,L340A), this experiment included cells expressing a stable Cdc25A (S82A) mutant, which is known to impair the checkpoint response to DNA damage (Busino et al., 2003). Mitotic entry was determined by immunostaining for Ser10 phosphorylated Histone H3. Cells infected with an empty viral vector showed only marginal mitotic entry, indicative of an intact G2 checkpoint, while cells expressing wild type Plk1 or Cdc25A (S82A) displayed an increase in cells entering mitosis. Strikingly and surprisingly, mitotic entry was significantly more pronounced in cells expressing Plk1 (R337A, L340A), indicating that Cdh1-mediated degradation of Plk1 is a critical step to establish and maintain the DNA damage checkpoint in G2. The relatively moderate elevation of mitotic entry observed when wild type Plk1 was expressed is likely due to the increased demand on the proteolytic machinery to degrade the excess of Plk1.

Figure 9:
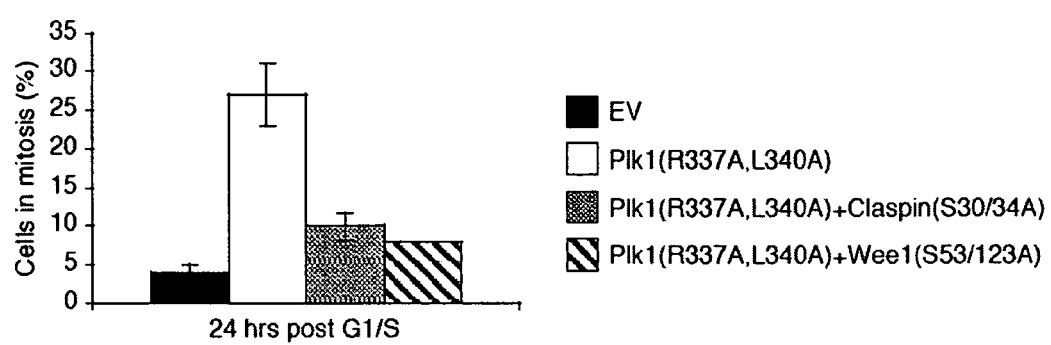
FIG. 9 shows expression of either a stable Claspin mutant or a stable Wee1 mutant prevents Plk1 from bypassing the checkpoint.

Importantly, the expression of a stable Claspin mutant (lacking the βTrCP degron) prevented Plk1 (R337A, L340A) from bypassing the checkpoint (FIG. 9), confirming that the induced degradation of Claspin is a major mechanism for Plk1 to induce premature mitosis. In FIG. 9, the experiment was performed as in FIG. 8G, except U2OS cells were also infected with retroviral constructs encoding both Plk1 (R337A,L340A) and either a Claspin mutant lacking the βTrcp degron [Claspin (S30/34A)] (Peschiaroli et al., 2006) or a Wee1 mutant lacking the βTrcp degron [Wee1 (S53/123A)] (Watanabe et al., 2004). The percentage of mitotic cells was monitored by immunodetection of Histone H3 phosphorylated on Ser10 using flow cytometry (n=3, ±SD for the first three bars and n=2 for the last one).

To elucidate the molecular mechanisms by which cells expressing Plk1 (R337A, L340A) are able to bypass this checkpoint, cell extracts were also analyzed by immunoblotting (FIG. 8H). All major events downstream from Plk1, which ultimately lead to the activation of Cdk1 and entry into mitosis, were observed in DNA-damaged cells expressing the stable Plk1 mutant but not wild type Plk1. FIG. 8H shows that compared to wild type Plk1 (lane 2), Plk1 (R337A, L340A) expression (lane 4) resulted in: (i) degradation of Claspin, with the consequent reduction in activating phosphorylation of Chk1; (ii) degradation of the Cdk1 inhibitor Wee1 [another SCF$^{\beta Trcp}$ substrate, whose degradation is promoted by Plk1 (Watanabe et al., 2004)]; (iii) elevated Cdc25A levels (likely due to low Chk1 activity); (iv) dephosphorylation of Cdk1 on Tyr15 (likely due to low levels of Wee1 and high Cdc25A expression); (v) lower p21 levels; and (vi) phosphorylation of Histone H3 on Ser10. Thus, cells entered mitosis despite the presence of DNA damage, visualized by the presence of H2AX phosphorylation (bottom panel in FIG. 8H and FIG. 10A-F).

Figure 10:
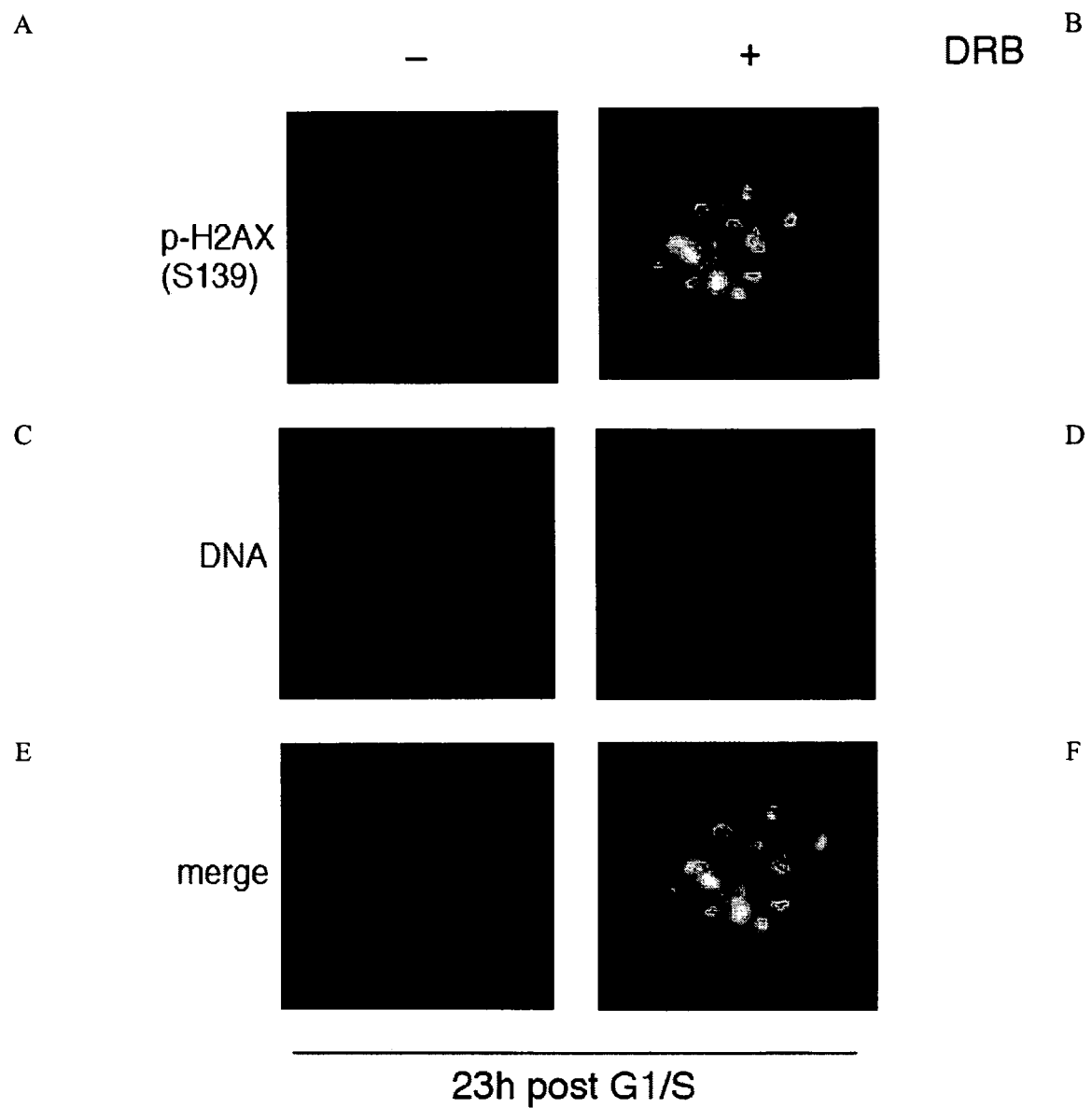
FIGS. 10A-F shows cells expressing stable Plk1 enter mitosis despite the presence of DNA damage.

FIGS. 10A-F show U2OS cells infected with a retrovirus encoding Plk1 (R337A,L340A) were synchronized at G1/S using a double thymidine block. Cells were then released from the block to allow progression towards G2. At seven hours post release, cells were pulsed for one hour with either solvent (−) or doxorubicin (DRB) (+). Thereafter, cells were incubated in fresh medium containing nocodazole to trap cells in mitosis. Samples were collected 23 hours after release from G1/S and analyzed by indirect immunofluorescence with an antibody specific for phosphorylated H2AX (FIGS. 10A-B) and DAPI (to visualize condensed DNA) (FIG. 10C-D). Chromosomes of all cells that entered mitosis after DRB treatment were positive for phospho-H2AX, showing that despite unrepaired DNA lesions cells expressing stable Plk1 reached mitosis. The merged results overlaying both stains are shown in FIGS. 10E-F.

Therefore, these data show that Cdh1-driven degradation of Plk1 in response to DNA damage is vital to maintain an efficient G2 checkpoint.

Example 4

Cdc14B relocates to the nucleus and associates with Cdh1 in G2 in a DNA-damage-dependent manner.

To be able to associate with and activate APC/C in late mitosis, Cdh1 must be dephosphorylated at sites that were phosphorylated by CDKs during S and G2 (Lukas et al., 1999; Mitra et al., 2006; Sorensen et al., 2001). The present data indicates that APC/C$^{Cdh1}$ is activated in G2 following DNA damage to target Plk1 and further indicates that a phosphatase may be required to remove the inhibitory phosphates from Cdh1. Studies in yeast have shown that Cdc14 dephosphorylates Cdh1 in late mitosis (D'Amours and Amon, 2004; Sullivan and Morgan, 2007). Two Cdc14 paralogs exist in mammals: Cdc14A and Cdc14B. Whereas Cdc14A is localized to the centrosomes, Cdc14B localizes to the nucleolus (Cho et al., 2005; Mailand et al., 2002). As a first step to study whether one of the Cdc14 phosphatases may dephosphorylate and activate Cdh1 in G2 phase in response to a genotoxic stress, experiments were designed to illustrate their subcellular localizations after treatment with doxorubicin or ionizing radiation. These experiments showed that Cdc14B was initially localized to the nucleolus; however surprisingly, following DNA damage, it moved to the nucleoplasm (FIG. 11A). In contrast, no change in subcellular localization was observed for Cdc14A. FIG. 11A shows that Cdc14B moves from the nucleolus to the nucleoplasm in response to DNA damage. U2OS cells transfected with a construct expressing GFP-tagged Cdc14B were synchronized as described in FIG. 6A, and then either treated with DRB [+/− caffeine (CAF)] or subjected to ionizing radiations (IR). Cells were then collected and analyzed by direct immunofluorescence. FIG. 11A shows micrographs of representative cells showing the subcellular localization of Cdc14B. FIG. 11B shows the quantification of cells with nuclear Cdc14B fluorescence at the indicated times post pulse with doxorubicin (n=3, ±SD).

FIG. 11C shows that Cdc14B translocation to the nucleus is independent of ATM. The experiment was performed as in FIG. 11A, except that asynchronous ATM+/+ and ATM−/− fibroblasts were used (n=2). The quantification of the cells with nuclear fluorescence is shown in FIG. 11D.

FIG. 11E shows the graphic results of an experiment performed as in FIG. 11A, except that GFP-tagged Cdc14B (T426A) was used (n=3).

FIG. 11F shows Cdh1 binds to Cdc14B in a DNA damage-dependent manner. U2OS cells infected with either an empty retrovirus (EV) or viruses encoding FLAG-tagged Cdc14B were synchronized and treated with DRB as described in FIG. 11A. Cells were collected two hours later, and whole cell extracts (WCE) were immunoprecipitated (IP) with anti-FLAG resin. The indicated proteins were detected by immunoblotting.

Interestingly, the nuclear localization of Cdc14B did not depend on ATM, as relocalization from the nucleolus was also observed in the presence of caffeine (FIG. 11A) and in ATM−/− fibroblasts (FIG. 11C). Human Cdc14B (SEQ ID NO:15) has three ATM phosphorylation consensus sites (one SQ and two TQs), two of which are not conserved in many other mammals. In contrast, the third site (Thr426) is conserved in all vertebrates. The Thr426 was mutated to Ala and this mutant Cdc14B (T426A) continued to move to the nucleus after DNA damage (FIG. 11E), confirming that ATM does not play a role in Cdc14B translocation.

Next, to test whether Cdc14B and Cdh1 physically interact in response to DNA damage in G2, co-immunoprecipitation experiments in G2 U2OS cells were performed. Surprisingly, an interaction between the two proteins was only observed after treatment with doxorubicin (FIG. 11F). Thus, during the G2 DNA damage response, Cdc14B moves to nucleus and binds Cdh1.

Example 5

Cdc14B Activates APC/C$^{Cdh1}$ after DNA Damage in G2

The finding that Cdc14B and Cdh1 interact in a DNA damage-dependent manner in G2 indicated that Cdc14B is involved in the reactivation of APC/C$^{Cdh1}$. To further test this hypothesis, the effect of silencing Cdc14B was determined. U2OS cells were transfected with previously validated siRNA oligos directed against either Cdc14B (SEQ ID NO:22) or Cdh1 (SEQ ID NO:21) and then synchronized. Upon reaching G2 (seven hours after release from G1/S), cells were pulsed with doxorubicin and collected at different times points thereafter (FIG. 12A).

In FIG. 12A U2OS cells were transfected with the indicated siRNA oligos and the cells were synchronized and treated with DRB as described in FIG. 6A. The cells were collected at the indicated times, and cell lysates were analyzed by immunoblotting with antibodies to the indicated proteins.

The graphs in FIGS. 12B, C, and D show the quantification of Claspin, Plk1, and Chk1 phosphorylated on Ser317 shown in FIG. 5A, at the 10 hour timepoint averaged with an additional, independent experiment. The value given for the amount of protein present in the control sample two hours after the end of the doxorubicin pulse was set as 1 (n=2).

U2OS cells, transfected with the indicated siRNA oligos, were treated as in FIG. 12A. Twenty-three hours after release from G1/S (16 hours after the doxorubicin pulse), cells were collected, and cell lysates were analyzed by immunoblotting with antibodies to the indicated proteins. The immunoblots are shown in FIG. 12E.

FIG. 12F shows Cdc14B mRNA levels of cells used in FIG. 5A and FIG. 5C that were analyzed eight hours after release from G1/S using real time PCR in triplicate measurements (±SD). The value given for the amount of Cdc14B mRNA present in the sample treated with control oligos was set as 1.

Strikingly, silencing of Cdc14B resulted in the stabilization of Plk1 to an extent comparable to that obtained from silencing Cdh1 (FIG. 6A and FIGS. 12A-B). Moreover, reduced levels of Claspin and impaired phosphorylation of Chk1 at Ser317 were observed in the Cdc14B knockdown samples, suggesting that the elevated Plk1 levels produced an effect on downstream targets. Thus, the presence of Cdc14B appears vital for Plk1 degradation in G2 upon genotoxic stress.

To investigate the impact of silencing Cdc14B on the maintenance of the G2 checkpoint, U2OS cells treated as in FIG. 12A were followed for a longer time course (up to 23 hours after release from G1/S). Even at these late time points, Plk1 was stabilized when Cdc14B was downregulated (FIG. 12E and FIG. 7D). Importantly, similar to what was observed when the stable Plk1 mutant was expressed (FIG. 8H), events downstream of Plk1, which lead to entry into mitosis, were observed in the Cdc14B knockdown samples (FIGS. 12E, F): increased degradation of Claspin and Wee1, reduction in the activating phosphorylation of Chk1, elevated Cdc25A levels, reduction in the inactivating phosphorylation of Cdk1, and phosphorylation of Histone H3 on Ser10.

Thus, Cdc14B, similar to Cdh1, is critical to establish and maintain the DNA damage checkpoint in G2. Interestingly, while downregulation of Cdc14B induced checkpoint bypass, the combination of Cdh1 and Cdc14B siRNAs had no additional effect (FIG. 14), showing that both proteins function in the same pathway.

The phosphatase activity of Cdc14B towards Cdh1 is predicted to occur on sites that are phosphorylated by CDKs. The four sites phosphorylated in Cdh1 by CDKs during S and G2 have been previously described (Lukas et al., 1999; Sorensen et al., 2001). To further investigate the role of Cdc14B in activating Cdh1 in G2 upon DNA damage, U2OS cells were infected with retroviruses expressing either wild type Cdh1 or Cdh1 (4×A), a constitutively active, phosphorylation-deficient Cdh1 mutant, in which the four CDK phosphorylation sites are mutated to Alanine. Subsequently, these cells were subjected to experiments analogous to those shown in FIG. 12-A-F.

FIG. 13A shows results after U2OS cells were retrovirally infected with either wild type Cdh1 or Cdh1 (4×A) mutant and subsequently transfected with the indicated siRNA oligos. Cells were then synchronized and treated with DRB as described herein for FIG. 6A, collected at the indicated times, and immunoblotted with antibodies to the indicated proteins. To facilitate comparison, a gray line separates samples treated with doxorubicin from untreated samples.

The graphs in FIGS. 13B, C, and D show the quantification of the levels of Claspin, Plk1, and Chk1 phosphorylated on Ser317 shown in (FIG. 13A) at the indicated timepoint averaged with an additional, independent experiment. The value given for the amount of protein present in the control sample two hours after the end of the doxorubicin pulse was set as 1 (n=2).

The immunoblots in FIG. 13E show U2OS cells expressing wild type Cdh1 or Cdh1 (4×A) that were transfected with the indicated siRNA oligos and treated as in (FIG. 13A). Twenty-three hours after release from G1/S (16 hours after the doxorubicin pulse), cells were collected, and cell lysates were analyzed by immunoblotting with antibodies to the indicated proteins.

Figure 13:
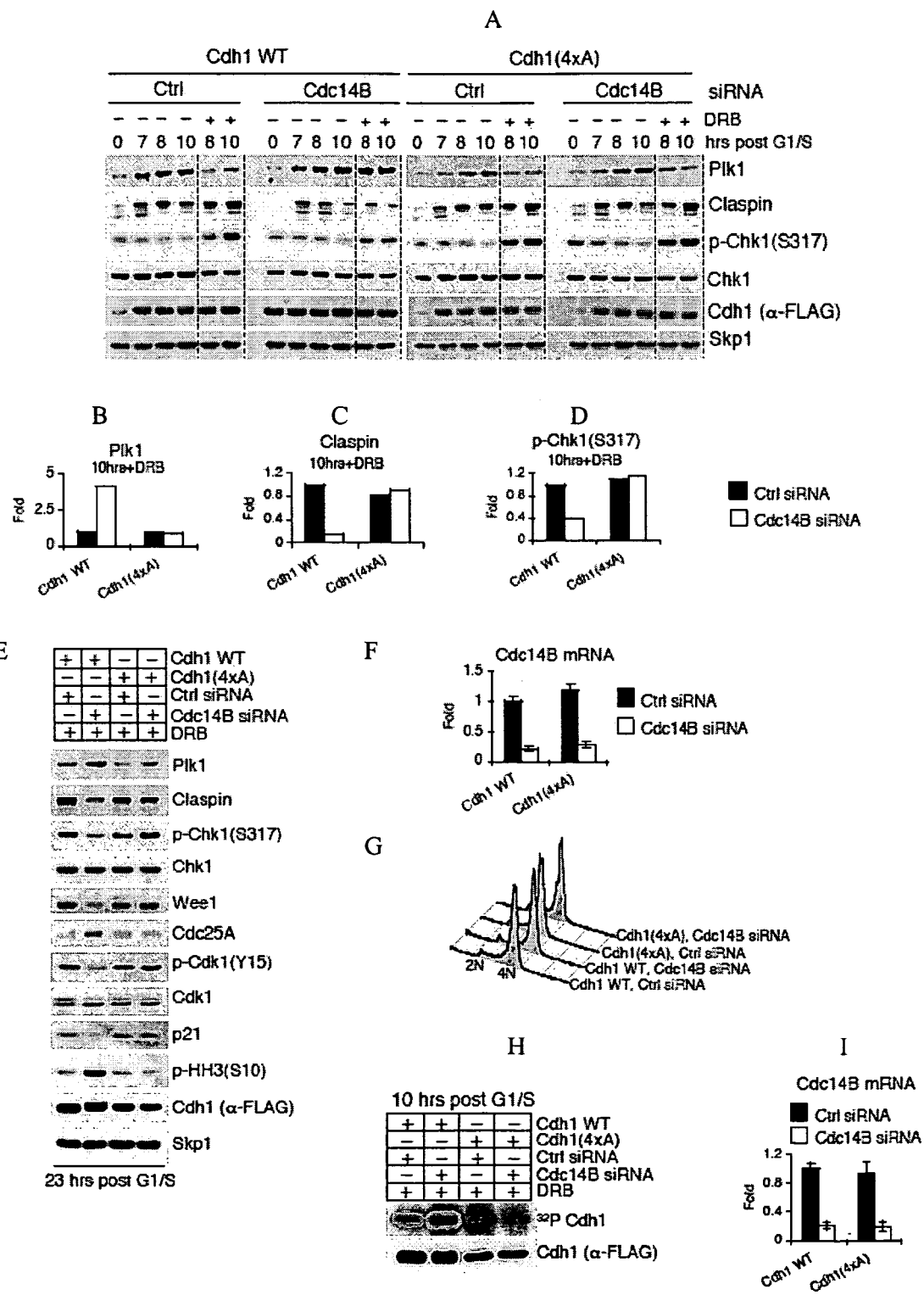
FIGS. 13A-I are immunoblots and graphs showing a constitutively active Cdh1 mutant is refractory to the silencing of Cdc14B.
Figure 14:
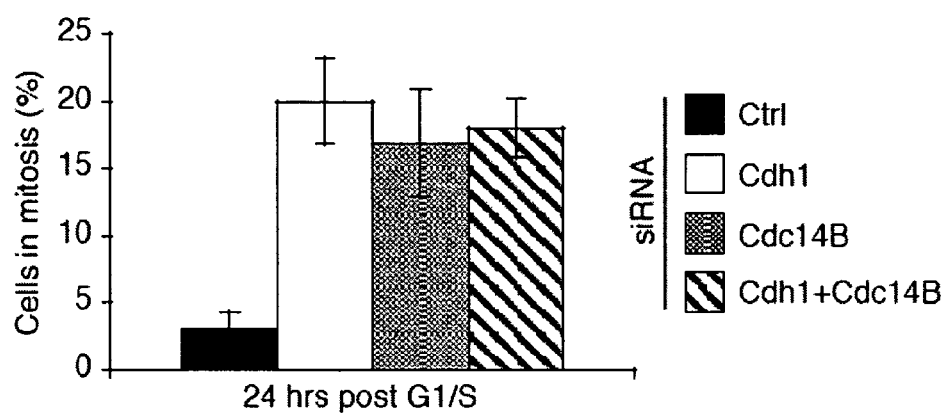
FIG. 14 is a graph illustrating that co-silencing of Cdh1 and Cdc14B is not synergistic in bypassing the checkpoint.

In FIG. 14, the experiment was performed as in FIG. 13E, except that U2OS cells were also transfected with siRNA oligos targeting both Cdh1 and Cdc14B. The percentage of mitotic cells was monitored by immunodetection of Histone H3 phosphorylated on Ser10 using flow cytometry (n=3). These results show that co-silencing of Cdh1 and Cdc14B is not synergistic in bypassing the checkpoint.

In FIG. 13F Cdc14B mRNA levels of cells used in (FIG. 13A) and (FIG. 13E) were analyzed eight hours after release from G1/S using real time PCR in triplicate measurements (±SD). The value given for the amount of Cdc14B mRNA present in the sample expressing wild type Cdh1 and treated with control oligos was set as 1.

In FIG. 13G synchrony in G2 was ascertained by flow cytometry for cells used in (FIG. 13A) at the time of doxorubicin treatment. Identical synchrony in G2 was obtained for cells used in (FIG. 13E).

In FIG. 13H, the immunoblotting experiment was performed as in (FIG. 13A), except that an in vivo labeling with $^{32}$P-orthophosphate was performed during the last three hours before cells were collected. Cdh1 was then immunoprecipitated under denaturing conditions, resolved by SDS-PAGE, and visualized by autoradiography (upper panel) or immunoblotting (bottom panel). FIG. 13 I shows Cdc14B mRNA levels analyzed by real time PCR.

As in non-infected cells, the silencing of Cdc14B in cells expressing wild type Cdh1 resulted in the stabilization of Plk1 in response to DNA damage and in downstream events regulated by Plk1 (FIGS. 13A-G). In marked contrast, silencing of Cdc14B did not stabilize Plk1 in cells expressing Cdh1 (4×A) (FIGS. 13A-G and FIG. 7H). Consequently, Claspin was not degraded, and Chk1 was efficiently phosphorylated upon DNA damage. Moreover, despite the downregulation of Cdc14B, cells expressing Cdh1 (4×A) displayed high levels of Wee1, inactivating phosphorylation of Cdk1, high levels of p21, and low levels of phosphorylation of Histone H3 on Ser10 (FIG. 13E, compare lane 2 and 4), showing that in the presence of a constitutively active Cdh1 mutant, Cdc14B becomes dispensable for sustaining the G2 checkpoint.

Importantly, these results show that after DNA damage, the in vivo phosphorylation of wild type Cdh1—but not that of Cdh1 (4×A)—increased after Cdc14B silencing (FIG. 13H), indicating that in response to genotoxic stress, Cdc14B dephosphorylates Cdh1 on the four sites phosphorylated by Cdk2.

These results indicate that upon DNA damage in G2, Cdh1 is the relevant target of Cdc14B and that CDK-mediated phosphorylation of Cdh1 is the relevant constraint that is removed by Cdc14B.

Example 6

The Cdc14B-Cdh1-Plk1 axis is deregulated in human tumors

These data show that the Cdc14B-Cdh1-Plk1 axis controls the G2 DNA damage checkpoint (see model in FIG. 15A). FIG. 15A is a schematic model of the G2 DNA damage response checkpoint. Black signifies activated forms of the respective proteins, and gray indicates inactive forms or degraded proteins. After induction of double strand breaks (DSB) in G2, ATM activates Chk2. In addition, ATM activates certain exonucleases to induce DSB resection, resulting in RPA coated, single-stranded DNA (ssDNA), which contributes to the recruitment of ATR. In parallel, Cdc14B is released from the nucleolus to the nucleoplasm, activating APC/$C^{Cdh1}$, which in turn targets Plk1 for proteasomal degradation. Because of the low levels of Plk1, phosphorylation of Claspin and Wee1 is reduced, preventing βTrcp-mediated degradation. Claspin is protected from APC/$C^{Cdh1}$-mediated degradation by Usp28. Stable Claspin promotes the ATR-mediated activation of Chk1, which, together with Chk2, targets Cdc25A (inducing its degradation) and p53 (promoting its stabilization and consequent induction of p21). As a result, Cdk1 activity is attenuated, and cells arrest in G2. Stable Wee1 contributes to this inhibition by directly phosphorylating Cdk1. The reduction in Cdk1 activity further removes the constraints on APC/$C^{Cdh1}$ activity.

FIGS. 15 B-D show poor patient survival correlates with low levels of Cdc14B and Cdh1 and high levels of Plk1 (gray). Data evaluated from the Rembrandt glioma database from the worldwide web (NCI-NIH) generated Kaplan-Meier survival curves of 219 patients with gliomas of all histological grades grouped by gene expression levels of Cdc14B (top plot), Cdh1 (middle plot), and Plk1 (bottom plot). The associated P values are shown for each plot.

To investigate a potential involvement of this pathway in human cancer, the Oncomine database was searches for the differential expression of Cdc14B, Cdh1, and Plk1 in normal versus tumor tissues. Analysis of the database results show the expression of Cdc14B (always) and Cdh1 (in most cases) to be significantly decreased in many common tumors, such as breast, prostate, ovary, liver, and brain tumors (FIGS. S10A-L). FIGS. 16A-R show the analysis of mRNA levels of Cdc14B, Cdh1, and Plk1 in different human tumors. All raw data was provided by the Oncomine database. The associated P values are shown for each study.

FIGS. 16 A, G, and M show initial data from (Chen et al., 2002) reanalyzed to show expression levels of Cdc14B (A), Cdh1 (G), and Plk1 (M) in non-tumor liver (Normal) and hepatocellular carcinoma (Carcinoma).

FIGS. 16 B, H, and N show initial data from (Richardson et al., 2006) reanalyzed to show expression levels of Cdc14B (B), Cdh1 (H), and Plk1 (N) in normal breast (Normal) and breast carcinoma (Carcinoma).

FIGS. 16 C, I, and O show initial data from (Sotiriou et al., 2006) reanalyzed to show expression levels of Cdc14B (C), Cdh1 (I), and Plk1 (Q) in Grade 1, Grade 2, and Grade 3 breast cancers.

FIGS. 16 D, J, and P show initial data from (Tomlins et al., 2007) reanalyzed to show expression levels of Cdc14B (D), Cdh1 (J), and Plk1 (P) in benign prostate (Normal) and prostate carcinoma (Carcinoma).

FIGS. 16 E, K, and Q show initial data from (Hendrix et al., 2006) reanalyzed to show expression levels of Cdc14B (E), Cdh1 (K), and Plk1 (O) in normal ovary (NO), ovarian endometrioid adenocarcinoma (OEA), ovarian serous adenocarcinoma (OSA), and ovarian mucinous adenocarcinoma (OMA).

FIGS. 16 F, L, and R show initial data from (Sun et al., 2006) reanalyzed to show expression levels of Cdc14B (F), Cdh1 (L), and Plk1 (R) in normal brain (NB), glioblastoma multiform (GBM), astrocytoma (AS), and oligodendroglioma (OD).

Conversely, levels of Plk1 were consistently and significantly increased in most tumors (FIGS. 16 M-R). Importantly, the decrease in Cdc14B expression and the increase in Plk1 levels significantly correlate with the grade of breast cancer.

Finally, downregulation of Cdc14B and Cdh1 and/or upregulation of Plk1 correlate with survival in glioma patients (FIG. 15B). These results suggest that a failure in the Cdc14B-Cdh1-Plk1 axis is likely to impair the G2 DNA damage checkpoint, with the consequent acquisition of genomic instability.

Discussion of Results

Following genotoxic stresses, Claspin promotes ATR-mediated phosphorylation and activation of Chk1 (Harper and Elledge, 2007). In G2, during the recovery from DNA replication stress or DNA damage, Claspin is phosphorylated by Plk1 and consequently degraded via $SCF^{\beta Trcp}$ (Mailand et al., 2006; Mamely et al., 2006; Peschiaroli et al., 2006). This process contributes to turning off the checkpoint to promote the entry of cells into mitosis. $SCF^{\beta Trcp}$-dependent ubiquitylation of Claspin remains active at least until prometaphase; however, Claspin reaccumulates only at the G1/S transition of the next cell cycle, suggesting that Claspin degradation is active during G1.

Several substrates degraded via SCF ligases in specific phases of the cell cycle are eliminated by the means of APC/C at different times. For example, p21 and M11 are degraded at G1/S via $SCF^{Skp2}$ and at G2/M via $APC/C^{Cdc20}$ (Amador et al., 2007; Liu et al., 2007). Similarly, Cdc25A, whose degradation is mediated by $SCF^{\beta Trcp}$ during S, is eliminated in G1 via $APC/C^{Cdh1}$ (Busino et al., 2003; Donzelli et al., 2002; Jin et al., 2003). The present results illustrate that, in contrast to degradation of Claspin in G2 via $SCF^{\beta Trcp}$, Claspin proteolysis in G1 cells is directed by $APC/C^{Cdh1}$ (FIGS. 1-4).

$APC/C^{Cdh1}$ maintains the G0/G1 state by ensuring that many positive regulators of S and M do not accumulate prematurely, a function important for genome stability (Guardavaccaro and Pagano, 2006; Peters, 2006). Claspin plays a poorly understood, positive role in DNA replication, which appears distinct from its role in checkpoint signaling. In fact, not only does expression of Claspin represent a reliable marker of cell proliferation in both human cancer and normal tissues (Tsimaratou et al., 2007), but Claspin overexpression has also been shown to increase cell proliferation (Lin et al., 2004). The present results support that Claspin represents another substrate that $APC/C^{Cdh1}$ keeps at low levels during G1 to avoid premature entry into S.

This initial result proved to be an invaluable portal to gain entry into the signaling network that mediates the G2 checkpoint, starting from the following observation. Upon DNA damage in G2, Claspin is no longer phosphorylated on its degron, blocking recognition by βTrcp (Peschiaroli et al., 2006). Therefore, the present experiments were undertaken to determine why Usp28 is required to deubiquitylate and stabilize Claspin upon DNA damage (Zhang et al., 2006). The present results demonstrate that $APC/C^{Cdh1}$ is reactivated in response to DNA damage (FIG. 5), thereby inducing ubiquitylation of Claspin, which is neutralized by Usp28 (FIGS. 6A-B).

These results lead to a novel question. If Claspin is ubiquitylated in response to DNA damage as a byproduct of $APC/C^{Cdh1}$ activation, but is protected from degradation by Usp28, what are the relevant substrate(s) that are degraded via $APC/C^{Cdh1}$ under these conditions? To address this question, in the present experiments, 15 substrates that are known to be targeted by this ligase in G0/G1 were surveyed and the data show that only two were downregulated: Plk1 and Cdc25A (FIG. 6E). The latter is known to be degraded via $SCF^{\beta Trcp}$ after genotoxic stresses (Busino et al., 2003; Jin et al., 2003), and, in fact, its levels did not promptly increase when Cdh1 was silenced (FIG. 6A). In contrast, Plk1 degradation was abolished when Cdh1 levels were lowered by siRNA (FIGS. 6A, B, C, D, and FIGS. 12A-E), showing that Cdh1 promotes Plk1 degradation. The lack of Claspin phosphorylation and consequent stabilization (Peschiaroli et al., 2006) is attributed to the inactivation of Plk1 that occurs after DNA damage (Smits et al., 2000), but how Plk1 is inactivated had remained largely unknown. The present experiments show that Plk1 is degraded via $APC/C^{Cdh1}$ following DNA damage. Downregulation of Cdh1 or the expression of a stable Plk1 mutant both resulted in the downregulation of Claspin in G2 DNA-damaged cells (FIGS. 6A, B, FIGS. 8A, H and FIGS. 5A, E). Thus, $APC/C^{Cdh1}$ exerts a dual control on Claspin stability: during G1, it promotes Claspin degradation, whereas after genotoxic stresses in G2, it allows Claspin stabilization by mediating the degradation of Plk1, which in turn disables Claspin proteolysis via $SCF^{\beta Trcp}$.

Knockdown of Cdh1 or the expression of a Cdh1-insensitive mutant of Plk1 also resulted in additional defects in the following cellular responses to DNA damage: activating phosphorylation of Chk1 (that correlates with the accumulation of Claspin), Cdc25A degradation, accumulation of Wee1, inactivating phosphorylation of Cdk1, induction of p21, and low levels of phosphorylation of Histone H3 on Ser10 (FIG. 6A, FIGS. 8A, H, FIGS. 12A, E, and FIG. 15A). Importantly, the present results show that $APC/C^{Cdh1}$-mediated degradation of Plk1 is essential for the establishment of an efficient G2 checkpoint that prevents entry into M upon genotoxic stresses (FIGS. 8G, H).

The degradation of Cdc25A and induction of p21 represent two established mechanisms that contribute to the inactivation of Cdk1 in response to DNA damage. The present results show for the first time that $APC/C^{Cdh1}$-mediated degradation of Plk1 is upstream of these events (see model in FIG. 15A). Moreover, by promoting Wee1 stabilization, the degradation of Plk1 also induces a direct inhibition of Cdk1. Thus, Plk1 proteolysis via APC/C$^{Cdh1}$ appears to be necessary for effective inhibition of Cdk1 after genotoxic stresses.

Figure 11:
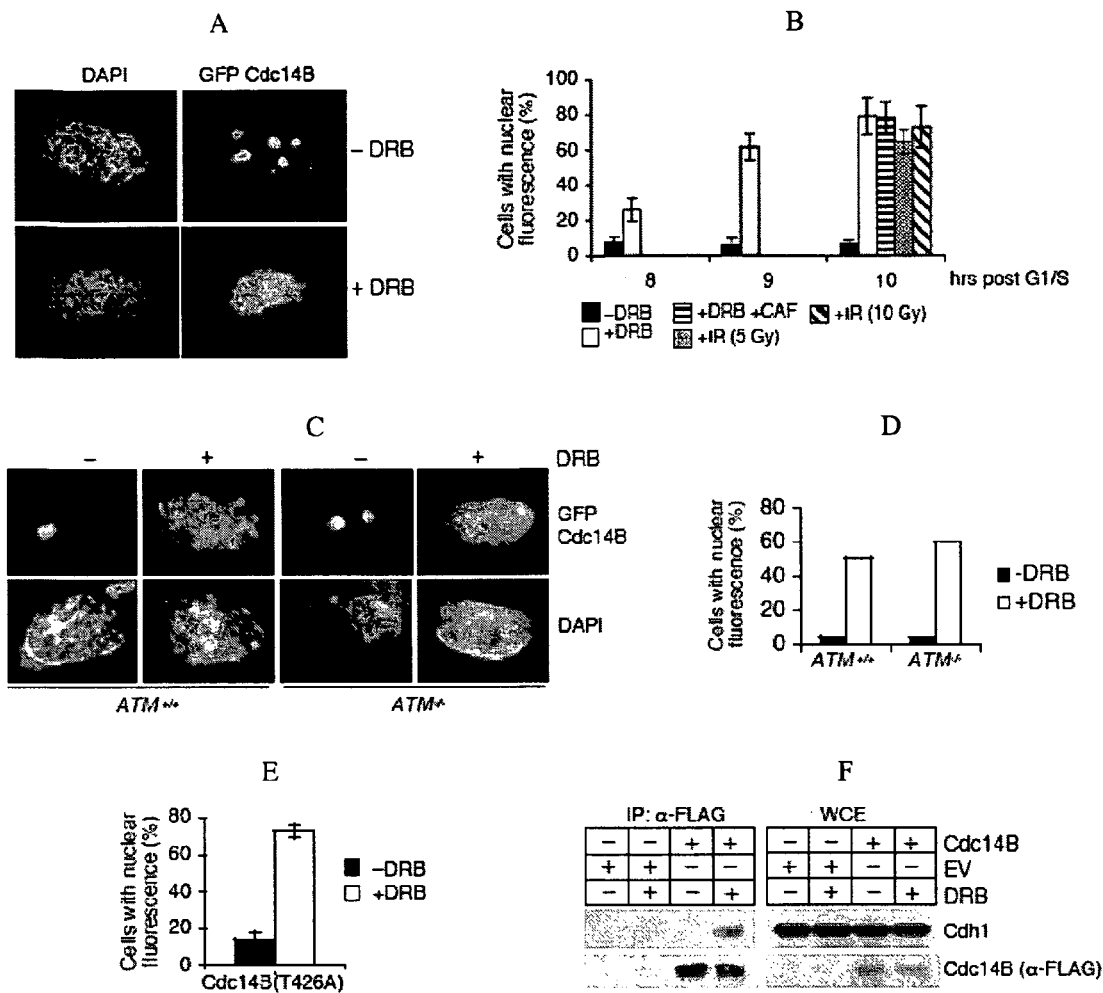
FIGS. 11A-F illustrate that Cdh1 associates with Cdc14B in G2 in response to DNA damage.
Figure 12:
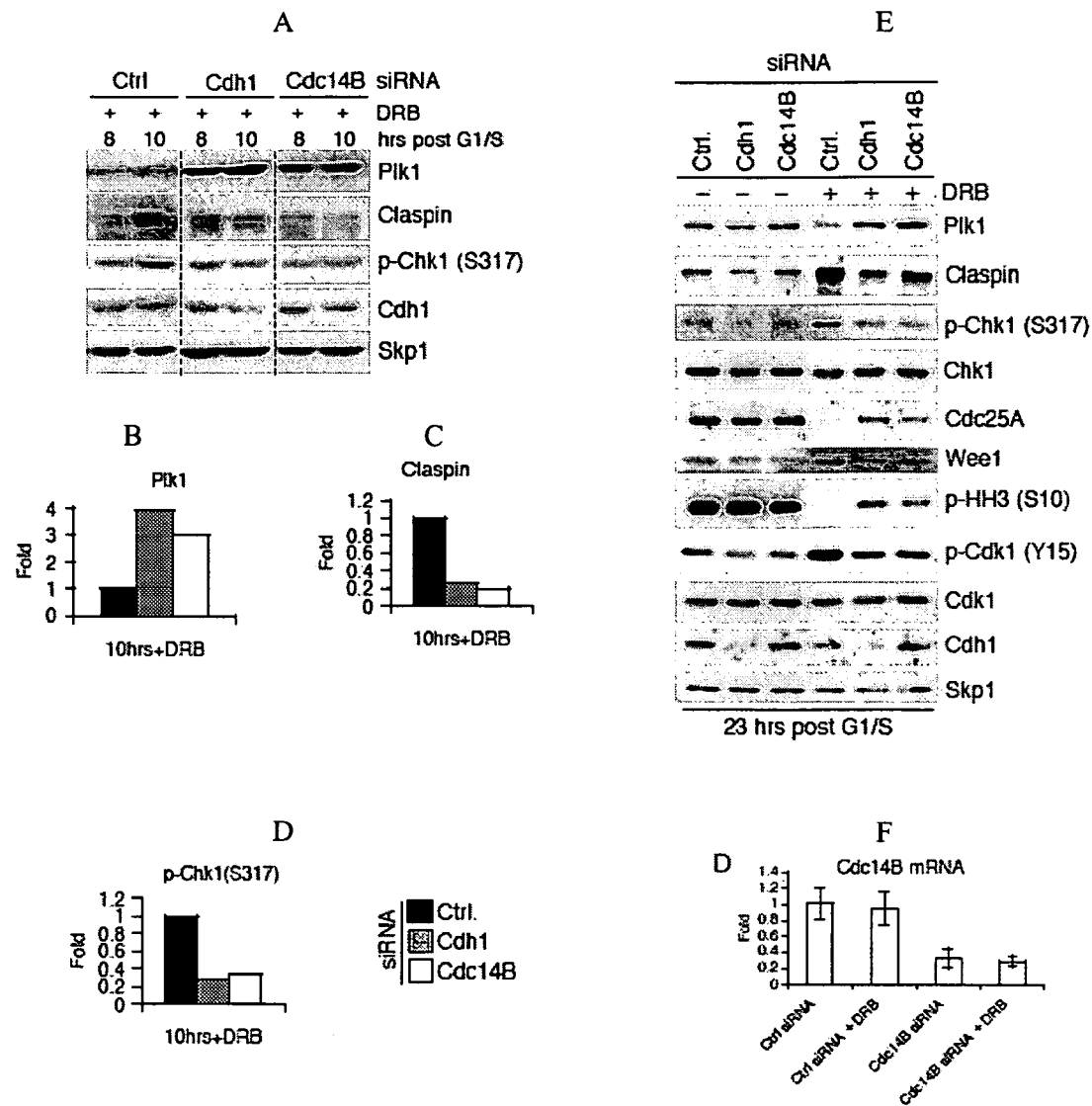
FIGS. 12A-F illustrate that DNA damage-dependent reactivation of APC/$C^{Cdh1}$ in G2 requires Cdc14B.

The molecular mechanisms leading to APC/C$^{Cdh1}$ reactivation in response to DNA damage were also investigated. CDK-dependent phosphorylation of Cdh1 dissociates Cdh1 from APC/C to prevent its activation from G1/S until anaphase. In yeast, Cdh1 activation in anaphase involves Cdh1 dephosphorylation by the Cdc14 phosphatase, but whether this mechanism is conserved in mammals is unknown. Interestingly, the levels of Cdc14 in yeast and frog do not oscillate during the cell cycle, but the protein is sequestered in the nucleolus until mitosis (D'Amours and Amon, 2004; Kaiser et al., 2004). Likewise, the expression of human Cdc14B mRNA does not change during cell cycle progression (Whitfield et al., 2002), and Cdc14B protein is localized to the nucleolus (Cho et al., 2005). The present results show that in response to DNA damage, human Cdc14B translocates from the nucleolus to the nucleoplasm, where it physically binds and activates Cdh1 (FIGS. 11-13). This result explains why Cdc14B is not expressed exclusively at G2/M, like other mitotic regulators. Rather, it is sequestered in the nucleolus during interphase, allowing prompt release in response to genotoxic stresses.

Since the expression of Cdh1 (4xA) makes Cdc14B dispensable upon DNA damage in G2, and silencing of Cdc14B increases the phosphorylation of wild type Cdh1 but not that of Cdh1 (4xA) (FIG. 13), it is proposed that Cdc14B activates Cdh1 by reversing the CDK-mediated phosphorylation of Cdh1.

Interestingly, Cdc14B release from the nucleolus is not dependent on ATM (whose activation is considered the most upstream signaling event after chromosomal breakage) (FIGS. 11A-E). The mechanism of mitotic release/activation of Cdc14 is relatively well understood in yeast, where the process is initiated by the "early anaphase release network" and completed by the "mitotic exit network" (D'Amours and Amon, 2004; Sullivan and Morgan, 2007).

In addition to Claspin, other Cdh1 substrates (e.g., cyclin A, cyclin B, and Geminin) are stable in damaged cells despite the reactivation of APC/C$^{Cdh1}$. Nevertheless, they are not destabilized when either Cdh1 and/or Usp28 are downregulated (FIG. 6A). Thus, these results indicate that two pools of APC/C$^{Cdh1}$ exist in G2. One pool (targeting cyclins and Geminin) is inactive both in the presence and absence of genotoxic stress, likely because it is inhibited by Emi1. (In fact, FIG. 5F shows that Emi1 binding to Cdc27 is not influenced by DNA damage.) The other pool (targeting Claspin and Plk1) is inhibited by phosphorylation and is reactivated in response to DNA damage, with Claspin ubiquitylation counteracted by Usp28.

While DUBs reverting protein modification by ubiquitin (e.g., monoubiquitylation and polyubiquitylation via Lys63) and ubiquitin-like molecules that do not target proteins for degradation are simple to envision, it is more difficult to envision why proteins should be stabilized by deubiquitylation rather than by lack of ubiquitylation. The present results show that in some cases, regulation by DUBs is necessary to counteract the activity of ubiquitin ligases on selective substrates. The specificity of DUBs, however, is poorly understood, and it is currently unknown how Usp28 targets Claspin but not Plk1.

The present analysis of the available databases also shows that the levels of Cdc14B, Plk1, and Cdh1 are deregulated in human tumors, and this deregulation correlates with the survival of cancer patients (FIG. 15B and FIG. 16). Abnormal levels or activity of these proteins is likely to disrupt orderly cell cycle progression. Furthermore, the present results illustrate that a failure in the Cdc14B-Cdh1-Plk1 axis induces an inefficient G2 DNA damage checkpoint, with the consequent risk of genomic instability.

In conclusion, while it was previously appreciated that the major function of APC/C$^{Cdh1}$ is the maintenance of the G0/G1 state, the present results demonstrate that in response to DNA damage, APC/C$^{Cdh1}$ is reactivated to allow the elimination of the pro-mitotic kinase Plk1. Importantly, APC/C$^{Cdh1}$-mediated degradation of Plk1 is essential for the establishment and maintenance of an efficient G2 checkpoint. Finally, the present data provide evidence that APC/C$^{Cdh1}$ is activated by Cdc14B released from the nucleolus upon genotoxic stresses. These findings indicate that the Cdc14B-Cdh1-Plk axis is a hub in the G2 DNA damage response in mammalian cells that is important for the inhibition of Cdk1 and the prevention of entry into mitosis. In contrast to the βTrCP-mediated degradation of Cdc25A and the p53-dependent induction of p21, Cdc14B, Plk1, and Cdh1 are well conserved from yeast to human, suggesting that the regulatory network described herein represents an "ancient" response to genotoxic stress that is conserved along evolution.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

While the compositions and methods of this invention have been described in terms of specific embodiments, it will be apparent to those of skill in the art that variations may be applied to the compositions and methods and in the steps or in the sequence of steps of the method described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope of the invention as defined by the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

REFERENCES

Amador, V., Ge, S., Santamaria, P., Guardavaccaro, D., and Pagano, M. (2007). APC/C (Cdc20) controls the ubiquitin-mediated degradation of p21 in prometaphase. Mol Cell 27, 462-473.

Bartek, J., and Lukas, J. (2007). DNA damage checkpoints: from initiation to recovery or adaptation. Curr Opin Cell Biol 19, 238-245.

Bassermann, F., von Klitzing, C., Munch, S., Bai, R., Kawaguchi, H., Morris, W., Peschel, C., and Duyster, J. (2005). NIPA defines an SCF-type mammalian E3 ligase that regulates mitotic entry. Cell 122, 45-57.

Busino, L., Donzelli, M., Chiesa, M., Guardavaccaro, D., Ganoth, D., Dorrello, N., Hershko, A., Pagano, M., and Draetta, G. F. (2003). Degradation of Cdc25A by bTrCP during S phase and in response to DNA damage. Nature 426, 87-91.

Cho, P., Liu, Y., Gomez, M., Dunlap, J., Tyers, M., and Wang, Y. (2005). The dual-specificity phosphatase CDC14B bundles and stabilizes microtubules. Mol Cell Biol 25, 4541-4551.

D'Amours, D., and Amon, A. (2004). At the interface between signaling and executing anaphase-Cdc14 and the FEAR network. Genes Dev 18, 2581-2595.

Donzelli, M., Squatrito, M., Ganoth, D., Hershko, A., Pagano, M., and Draetta, G. (2002). Dual mode of degradation of Cdc25 A phosphatase. Embo J 21, 4875-4884.

Dorrello, N. V., Peschiaroli, A., Guardavaccaro, D., Colburn, N. H., Sherman, N. E., and Pagano, M. (2006). S6K1- and bTRCP-mediated degradation of PDCD4 promotes protein translation and cell growth. Science 314, 467-471.

Guardavaccaro, D., Frescas, D., Dorrello, N., Peschiaroli, A., Multani, A., Cardozo, T., Lasorella, A., Iavarone, A., Chang, S., Hernando, E., and Pagano, M. (2008). Control of chromosome stability by the bTrCP-REST-Mad2 axis. Nature 452, 365-369.

Guardavaccaro, D., and Pagano, M. (2006). Stabilizers and destabilizers controlling cell cycle oscillators. Mol Cell 22, 1-4.

Harper, W., and Elledge, S. J. (2007). The DNA damage response: ten years after. Mol Cell 28, 739-745.

Jin, J., Shirogane, T., Xu, L., Nalepa, G., Qin, J., Elledge, S., and Harper, W. (2003). $SCF^{bTrcp}$ links Chk1 signaling to degradation of the Cdc25A protein phosphatase. Genes Dev 17, 3062-3074.

Kaiser, B. K., Nachury, M. V., Gardner, B. E., and Jackson, P. (2004). *Xenopus* Cdc14 a/bare localized to the nucleolus and centrosome and are required for embryonic cell division. BMC Cell Biol 5, 27.

Kastan, M., and Bartek, J. (2004). Cell-cycle checkpoints and cancer. Nature 432, 316-323.

Lin, S. Y., Li, K., Stewart, G., and Elledge, S. (2004). Human Claspin works with BRCA1 to both positively and negatively regulate cell proliferation. Proc Natl Acad Sci USA 101, 6484-6489.

Lindon, C., and Pines, J. (2004). Ordered proteolysis in anaphase inactivates Plk1 to contribute to proper mitotic exit in human cells. J Cell Biol 164, 233-241.

Liu, H., Cheng, E. H., and Hsieh, J. J. (2007). Bimodal degradation of MLL by $SCF^{Skp2}$ and $APC^{Cdc20}$ assures cell cycle execution: a critical regulatory circuit lost in leukemogenic MLL fusions. Genes Dev 21, 2385-2398.

Lukas, C., Sorensen, C., Kramer, E., Santoni, E., Lindeneg, C., Peters, J. M., Bartek, J., and Lukas, J. (1999). Accumulation of cyclin B1 requires E2F and cyclin-A-dependent rearrangement of the anaphase-promoting complex. Nature 401, 815-818.

Mailand, N., Bekker-Jensen, S., Bartek, J., and Lukas, J. (2006). Destruction of Claspin by $SCF^{bTrCP}$ restrains Chk1 activation and facilitates recovery from genotoxic stress. Mol Cell 23, 307-318.

Mailand, N., Lukas, C., Kaiser, B., Jackson, P., Bartek, J., and Lukas, J. (2002). Deregulated human Cdc14A phosphatase disrupts centrosome separation and chromosome segregation. Nat Cell Biol 4, 317-322.

Mamely, I., van Vugt, M., Smits, V., Semple, J., Lemmens, B., Perrakis, A., Medema, R., and Freire, R. (2006). Polo-like kinase-1 controls proteasome-dependent degradation of Claspin during checkpoint recovery. Curr Biol 16, 1950-1955.

Mitra, J., Enders, G., Azizkhan, J., and Lengel, K. (2006). Dual regulation of the anaphase promoting complex in human cells by cyclin A-Cdk2 and cyclin A-Cdk1 complexes. Cell Cycle 5, 661-666.

Peschiaroli, A., Dorrello, N., Guardavaccaro, D., Venere, M., Halazonetis, T., Sherman, N., and Pagano, M. (2006). $SCF^{bTrCP}$-mediated degradation of Claspin regulates recovery from the DNA replication checkpoint response. Mol Cell 23, 319-329.

Peters, J. M. (2006). The anaphase promoting complex/cyclosome: a machine designed to destroy. Nat Rev Mol Cell Biol 7, 644-656.

Smits, V., Klompmaker, R., Arnaud, L., Rijksen, G., Nigg, E., and Medema, R. (2000). Polo-like kinase-1 is a target of the DNA damage checkpoint. Nat Cell Biol 2, 672-676.

Sorensen, C., Lukas, C., Kramer, E., Peters, J. M., Bartek, J., and Lukas, J. (2001). A conserved cyclin-binding domain determines functional interplay between anaphase-promoting complex-Cdh1 and cyclin A-Cdk2 during cell cycle progression. Mol Cell Biol 21, 3692-3703.

Sudo, T., Ota, Y., Kotani, S., Nakao, M., Takami, Y., Takeda, S., and Saya, H. (2001). Activation of Cdh1-dependent APC is required for G1 cell cycle arrest and DNA damage-induced G2 checkpoint in vertebrate cells. Embo J 20, 6499-6508.

Sullivan, M., and Morgan, D. (2007). Finishing mitosis, one step at a time. Nat Rev Mol Cell Biol 8, 894-903.

Tsimaratou, K., Kletsas, D., Kastrinakis, N., Tsantoulis, P., Evangelou, K., Sideridou, M., Liontos, M., Poulias, I., Venere, M., Salmas, M., et al. (2007). Evaluation of claspin as a proliferation marker in human cancer and normal tissues. J Pathol 211, 331-339.

Watanabe, N., Arai, H., Nishihara, Y., Taniguchi, M., Watanabe, N., Hunter, T., and Osada, H. (2004). M-phase kinases induce phospho-dependent ubiquitination of somatic Wee1 by SCFbTrCP. Proc Natl Acad Sci USA 101, 4419-4424.

Whitfield, M., Sherlock, G., Saldanha, A., Murray, J., Ball, C., Alexander, K., Matese, J., Perou, C., Hurt, M., Brown, P., and Botstein, D. (2002). Identification of genes periodically expressed in the human cell cycle and their expression in tumors. Mol Biol Cell 13, 1977-2000.

Zhang, D., Zaugg, K., Mak, T., and Elledge, S. (2006). A role for the deubiquitinating enzyme USP28 in control of the DNA-damage response. Cell 126, 529-542.

Araki, M., Yu, H., and Asano, M. (2005). A novel motif governs APC-dependent degradation of *Drosophila* ORC1 in vivo. Genes Dev 19, 2458-2465.

Bashir, T., Dorrello, N. V., Amador, V., Guardavaccaro, D., and Pagano, M. (2004). Control of the SCF (Skp2-Cks1) ubiquitin ligase by the APC/C (Cdh1) ubiquitin ligase. Nature 428, 190-193.

Bassermann, F., von Klitzing, C., Munch, S., Bai, R. Y., Kawaguchi, H., Morris, S. W., Peschel, C., and Duyster, J. (2005). NIPA defines an SCF-type mammalian E3 ligase that regulates mitotic entry. Cell 122, 45-57.

Brummelkamp, T. R., Bernards, R., and Agami, R. (2002). A system for stable expression of short interfering RNAs in mammalian cells. Science 296, 550-553.

Carrano, A. C., Eytan, E., Hershko, A., and Pagano, M. (1999). SKP2 is required for ubiquitin-mediated degradation of the CDK inhibitor p27. Nat Cell Biol 1, 193-199.

Carrano, A. C., and Pagano, M. (2001). Role of the F-box protein Skp2 in adhesion-dependent cell cycle progression. J Cell Biol 153, 1381-1390.

Chen, X., Cheung, S. T., So, S., Fan, S. T., Barry, C., Higgins, J., Lai, K. M., Ji, J., Dudoit, S., Ng, I. O., et al. (2002). Gene expression patterns in human liver cancers. Mol Biol Cell 13, 1929-1939.

Donzelli, M., Squatrito, M., Ganoth, D., Hershko, A., Pagano, M., and Draetta, G. F. (2002). Dual mode of degradation of Cdc25 A phosphatase. Embo J 21, 4875-4884.

Dorrello, N. V., Peschiaroli, A., Guardavaccaro, D., Colburn, N. H., Sherman, N. E., and Pagano, M. (2006). S6K1- and betaTRCP-mediated degradation of PDCD4 promotes protein translation and cell growth. Science 314, 467-471.

Faha, B., Harlow, E., and Lees, E. (1993). The adenovirus E1A-associated kinase consists of cyclin E-p33cdk2 and cyclin A-p33cdk2. J Virol 67, 2456-2465.

Fong, A., and Sun, S. C. (2002). Genetic evidence for the essential role of beta-transducin repeat-containing protein in the inducible processing of NF-kappa B2/p100. J Biol Chem 277, 22111-22114.

Frescas, D., Guardavaccaro, D., Bassermann, F., Koyama-Nasu, R., and Pagano, M. (2007). JHDM1B/FBXL10 is a nucleolar protein that represses transcription of ribosomal RNA genes. Nature 450, 309-313.

Guardavaccaro, D., Frescas, D., Dorello, N., Peschiaroli, A., Multani, A., Cardozo, T., Lasorella, A., Iavarone, A., Chang, S., Hernando, E., Pagano, M. (2008). Control of chromosome stability by the TRCP-REST-MAD2 axis. Nature 452, 365-369.

Guardavaccaro, D., Kudo, Y., Boulaire, J., Barchi, M., Busino, L., Donzelli, M., Margottin-Goguet, F., Jackson, P. K., Yamasaki, L., and Pagano, M. (2003). Control of Meiotic and Mitotic Progression by the F Box Protein beta-Trcp1 In Vivo. Dev Cell 4, 799-812.

Heffernan, T. P., Simpson, D. A., Frank, A. R., Heinloth, A. N., Paules, R. S., Cordeiro-Stone, M., and Kaufmann, W. K. (2002). An ATR- and Chk1-dependent S checkpoint inhibits replicon initiation following UVC-induced DNA damage. Mol Cell Biol 22, 8552-8561.

Hendrix, N. D., Wu, R., Kuick, R., Schwartz, D. R., Fearon, E. R., and Cho, K. R. (2006). Fibroblast growth factor 9 has oncogenic activity and is a downstream target of Wnt signaling in ovarian endometrioid adenocarcinomas. Cancer Res 66, 1354-1362.

Jin, J., Shirogane, T., Xu, L., Nalepa, G., Qin, J., Elledge, S. J., and Harper, J. W. (2003). SCFbeta-TRCP links Chk1 signaling to degradation of the Cdc25A protein phosphatase. Genes Dev 17, 3062-3074.

Ke, P. Y., and Chang, Z. F. (2004). Mitotic degradation of human thymidine kinase 1 is dependent on the anaphase-promoting complex/cyclosome-CDH1-mediated pathway. Mol Cell Biol 24, 514-526.

Littlepage, L. E., and Ruderman, J. V. (2002). Identification of a new APC/C recognition domain, the A box, which is required for the Cdh1-dependent destruction of the kinase Aurora-A during mitotic exit. Genes Dev 16, 2274-2285.

Peschiaroli, A., Dorrello, N. V., Guardavaccaro, D., Venere, M., Halazonetis, T., Sherman, N. E., and Pagano, M. (2006). SCFbetaTrCP-mediated degradation of Claspin regulates recovery from the DNA replication checkpoint response. Mol Cell 23, 319-329.

Richardson, A. L., Wang, Z. C., De Nicolo, A., Lu, X., Brown, M., Miron, A., Liao, X., Iglehart, J. D., Livingston, D. M., and Ganesan, S. (2006). X chromosomal abnormalities in basal-like human breast cancer. Cancer Cell 9, 121-132.

Rodier, G., Coulombe, P., Tanguay, P. L., Boutonnet, C., and Meloche, S. (2008). Phosphorylation of Skp2 regulated by CDK2 and Cdc14B protects it from degradation by APC (Cdh1) in G1 phase. Embo J 27, 679-691.

Rodrigo-Brenni, M. C., and Morgan, D. O. (2007). Sequential E2s drive polyubiquitin chain assembly on APC targets. Cell 130, 127-139.

Sotiriou, C., Wirapati, P., Loi, S., Harris, A., Fox, S., Smeds, J., Nordgren, H., Farmer, P., Praz, V., Haibe-Kains, B., et al. (2006). Gene expression profiling in breast cancer: understanding the molecular basis of histologic grade to improve prognosis. J Natl Cancer Inst 98, 262-272.

Sun, L., Hui, A. M., Su, Q., Vortmeyer, A., Kotliarov, Y., Pastorino, S., Passaniti, A., Menon, J., Walling, J., Bailey, R., et al. (2006). Neuronal and glioma-derived stem cell factor induces angiogenesis within the brain. Cancer Cell 9, 287-300.

Tomlins, S. A., Mehra, R., Rhodes, D. R., Cao, X., Wang, L., Dhanasekaran, S. M., Kalyana-Sundaram, S., Wei, J. T., Rubin, M. A., Pienta, K. J., et al. (2007). Integrative molecular concept modeling of prostate cancer progression. Nat Genet 39, 41-51.

Zhang, D., Zaugg, K., Mak, T. W., and Elledge, S. J. (2006). A role for the deubiquitinating enzyme USP28 in control of the DNA-damage response. Cell 126, 529-542.

---

What is claimed is:

1. A method of screening for an agent for sensitizing a target cell to apoptosis or cell death comprising:
   i) contacting a cell expressing Cdc14B protein with a test compound;
   ii) comparing the amount of the Cdc14B protein to a control, wherein the control is the amount of Cdc14B protein in the absence of the test compound; and
   iii) selecting a test compound that decreases the amount of Cdc14B protein as an agent for sensitizing a target cell to apoptosis or cell death.

2. The method of claim 1, wherein the target cell is a diseased or abnormal cell that exhibits a disease or an abnormal condition selected from the group consisting of cancer, infection, immune disorder, cardiovascular disease, and inflammatory disorder.

3. The method of claim 1, wherein the test compound is an siRNA.

4. The method of claim 3, wherein the siRNA is SEQ ID NO: 22.

5. The method of claim 1, wherein the Cdc14B protein comprises the sequence SEQ ID NO: 15.

* * * * *

SEQUENCE LISTING

```
<160> NUMBER OF SEQ ID NOS: 33

<210> SEQ ID NO 1
<211> LENGTH: 605
<212> TYPE: PRT
<213> ORGANISM: Homo sapiens

<400> SEQUENCE: 1

Met Asp Pro Ala Glu Ala Val Leu Gln Glu Lys Ala Leu Lys Phe Met
1               5                   10                  15

Cys Ser Met Pro Arg Ser Leu Trp Leu Gly Cys Ser Ser Leu Ala Asp
                20                  25                  30

Ser Met Pro Ser Leu Arg Cys Leu Tyr Asn Pro Gly Thr Gly Ala Leu
            35                  40                  45

Thr Ala Phe Gln Asn Ser Ser Glu Arg Glu Asp Cys Asn Asn Gly Glu
        50                  55                  60

Pro Pro Arg Lys Ile Ile Pro Glu Lys Asn Ser Leu Arg Gln Thr Tyr
65                  70                  75                  80
```

```
Asn Ser Cys Ala Arg Leu Cys Leu Asn Gln Glu Thr Val Cys Leu Ala
                85                  90                  95

Ser Thr Ala Met Lys Thr Glu Asn Cys Val Ala Lys Thr Lys Leu Ala
            100                 105                 110

Asn Gly Thr Ser Ser Met Ile Val Pro Lys Gln Arg Lys Leu Ser Ala
            115                 120                 125

Ser Tyr Glu Lys Glu Lys Glu Leu Cys Val Lys Tyr Phe Glu Gln Trp
            130                 135                 140

Ser Glu Ser Asp Gln Val Glu Phe Val Glu His Leu Ile Ser Gln Met
145                 150                 155                 160

Cys His Tyr Gln His Gly His Ile Asn Ser Tyr Leu Lys Pro Met Leu
                165                 170                 175

Gln Arg Asp Phe Ile Thr Ala Leu Pro Ala Arg Gly Leu Asp His Ile
            180                 185                 190

Ala Glu Asn Ile Leu Ser Tyr Leu Asp Ala Lys Ser Leu Cys Ala Ala
            195                 200                 205

Glu Leu Val Cys Lys Glu Trp Tyr Arg Val Thr Ser Asp Gly Met Leu
    210                 215                 220

Trp Lys Lys Leu Ile Glu Arg Met Val Arg Thr Asp Ser Leu Trp Arg
225                 230                 235                 240

Gly Leu Ala Glu Arg Arg Gly Trp Gly Gln Tyr Leu Phe Lys Asn Lys
            245                 250                 255

Pro Pro Asp Gly Asn Ala Pro Pro Asn Ser Phe Tyr Arg Ala Leu Tyr
            260                 265                 270

Pro Lys Ile Ile Gln Asp Ile Glu Thr Ile Glu Ser Asn Trp Arg Cys
        275                 280                 285

Gly Arg His Ser Leu Gln Arg Ile His Cys Arg Ser Glu Thr Ser Lys
        290                 295                 300

Gly Val Tyr Cys Leu Gln Tyr Asp Asp Gln Lys Ile Val Ser Gly Leu
305                 310                 315                 320

Arg Asp Asn Thr Ile Lys Ile Trp Asp Lys Asn Thr Leu Glu Cys Lys
            325                 330                 335

Arg Ile Leu Thr Gly His Thr Gly Ser Val Leu Cys Leu Gln Tyr Asp
            340                 345                 350

Glu Arg Val Ile Ile Thr Gly Ser Ser Asp Ser Thr Val Arg Val Trp
            355                 360                 365

Asp Val Asn Thr Gly Glu Met Leu Asn Thr Leu Ile His His Cys Glu
    370                 375                 380

Ala Val Leu His Leu Arg Phe Asn Asn Gly Met Met Val Thr Cys Ser
385                 390                 395                 400

Lys Asp Arg Ser Ile Ala Val Trp Asp Met Ala Ser Pro Thr Asp Ile
            405                 410                 415

Thr Leu Arg Arg Val Leu Val Gly His Arg Ala Ala Val Asn Val Val
            420                 425                 430

Asp Phe Asp Asp Lys Tyr Ile Val Ser Ala Ser Gly Asp Arg Thr Ile
        435                 440                 445

Lys Val Trp Asn Thr Ser Thr Cys Glu Phe Val Arg Thr Leu Asn Gly
        450                 455                 460

His Lys Arg Gly Ile Ala Cys Leu Gln Tyr Arg Asp Arg Leu Val Val
465                 470                 475                 480

Ser Gly Ser Ser Asp Asn Thr Ile Arg Leu Trp Asp Ile Glu Cys Gly
            485                 490                 495

Ala Cys Leu Arg Val Leu Glu Gly His Glu Glu Leu Val Arg Cys Ile
            500                 505                 510
```

```
Arg Phe Asp Asn Lys Arg Ile Val Ser Gly Ala Tyr Asp Gly Lys Ile
            515                 520                 525

Lys Val Trp Asp Leu Val Ala Ala Leu Asp Pro Arg Ala Pro Ala Gly
        530                 535                 540

Thr Leu Cys Leu Arg Thr Leu Val Glu His Ser Gly Arg Val Phe Arg
545                 550                 555                 560

Leu Gln Phe Asp Glu Phe Gln Ile Val Ser Ser Ser His Asp Asp Thr
                565                 570                 575

Ile Leu Ile Trp Asp Phe Leu Asn Asp Pro Ala Ala Gln Ala Glu Pro
            580                 585                 590

Pro Arg Ser Pro Ser Arg Thr Tyr Thr Tyr Ile Ser Arg
        595                 600                 605

<210> SEQ ID NO 2
<211> LENGTH: 6146
<212> TYPE: DNA
<213> ORGANISM: Homo sapiens

<400> SEQUENCE: 2
taagagaggg cgggggaag gaagaggagg cgggatccgg gcgctgcgtt ggctgcggcc    60
tggcaccaaa gggcggccc cggcggagag cggacccagt ggcctcggcg attatggacc   120
cggccgaggc ggtgctgcaa gagaaggcac tcaagtttat gtgctctatg cccaggtctc   180
tgtggctggg ctgctccagc ctggcggaca gcatgccttc gctgcgatgc ctgtataacc   240
cagggactgg cgcactcaca gctttccaga attcctcaga gagagaagac tgtaataatg   300
gcgaaccccc taggaagata ataccagaga agaattcact tagacagaca tacaacagct   360
gtgccagact ctgcttaaac caagaaacag tatgtttagc aagcactgct atgaagactg   420
agaattgtgt ggccaaaaca aaacttgcca atggcacttc cagtatgatt gtgcccaagc   480
aacggaaact ctcagcaagc tatgaaaagg aaaaggaact gtgtgtcaaa tactttgagc   540
agtggtcaga gtcagatcaa gtggaatttg tggaacatct tatatcccaa atgtgtcatt   600
accaacatgg gcacataaac tcgtatctta aacctatgtt gcagagagat ttcataactg   660
ctctgccagc tcggggattg gatcatattg ctgagaacat tctgtcatac ctggatgcca   720
aatcactatg tgctgctgaa cttgtgtgca aggaatggta ccgagtgacc tctgatggca   780
tgctgtggaa gaagcttatc gagagaatgg tcaggacaga ttctctgtgg agaggcctgg   840
cagaacgaag aggatgggga cagtatttat tcaaaaacaa acctcctgac gggaatgctc   900
ctcccaactc ttttttataga gcactttatc ctaaaattat acaagacatt gagacaatag   960
aatctaattg gagatgtgga agacatagtt tacagagaat tcactgccga agtgaaacaa  1020
gcaaaggagt ttactgttta cagtatgatg atcagaaaat agtaagcggc cttcgagaca  1080
acacaatcaa gatctgggat aaaaacacat ggaatgcaa gcgaattctc acaggccata  1140
caggttcagt cctctgtctc cagtatgatg agagagtgat cataacagga tcatcggatt  1200
ccacggtcag agtgtgggat gtaaatacag gtgaaatgct aaacacgttg attcaccatt  1260
gtgaagcagt tctgcacttg cgtttcaata atggcatgat ggtgacctgc tccaaagatc  1320
gttccattgc tgtatgggat atggcctccc caactgacat taccctccgg agggtgctgg  1380
tcggacaccg agctgctgtc aatgttgtag actttgatga caagtacatt gtttctgcat  1440
ctgggggatag aactataaag gtatggaaca caagtacttg tgaatttgta aggaccttaa  1500
atggacacaa acgaggcatt gcctgtttgc agtacagga caggctggta gtgagtggct  1560
catctgacaa cactatcaga ttatgggaca tagaatgtgg tgcatgttta cgagtgttag  1620
```

```
aaggccatga ggaattggtg cgttgtattc gatttgataa caagaggata gtcagtgggg    1680
cctatgatgg aaaaattaaa gtgtgggatc ttgtggctgc tttggacccc cgtgctcctg    1740
cagggacact ctgtctacgg acccttgtgg agcattccgg aagagttttt cgactacagt    1800
ttgatgaatt ccagattgtc agtagttcac atgatgacac aatcctcatc tgggacttcc    1860
taaatgatcc agctgcccaa gctgaacccc cccgttcccc ttctcgaaca tacacctaca    1920
tctccagata aataaccata cactgacctc atacttgccc aggacccatt aaagttgcgg    1980
tatttaacgt atctgccaat accaggatga gcaacaacag taacaatcaa actactgccc    2040
agtttccctg gactagccga ggagcagggc tttgagactc ctgttgggac acagttggtc    2100
tgcagtcggc ccaggacggt ctactcagca caactgactg cttcagtgct gctatcagaa    2160
gatgtcttct atcttttgtg aatgattgga acttttaaac ctcccctcct ctcctccttt    2220
cacctctgca cctagttttt tcccattggt tccagacaaa ggtgacttat aaatatattt    2280
agtgttttgc cagaatctct cttgctttgc cattaagcag aagaactagt ttccctgtat    2340
agcctgctgg gagagaccca ttctagggt atggggatg cagcttcaag cccagtgccc    2400
agtgtctccc tgttaactgc aggaatgcca agcacctggc cagagcagcc cagccccaat    2460
atgcttagga ggagacagag ttccctctgt atagcctctg ggacaagaaa aagaaaacac    2520
aagaatgtat acactggaag atttgggcct cctgcctgcc ttctctttgt ttctgttcct    2580
cttcccatct actcccctac gccccttcaa cctttttttct ctgtctgctt cacctgagaa    2640
gaaagtgtac gaagagagtg tcctcctctc acatgagcca gatcagccag aaaatgcaac    2700
acttggaaga gttaaatgct gttcagtgaa gatttcagcc ccaggccttt gctgcaagtg    2760
accctgtggc aacagtggat tctcagacat gatactctca tcatatttgc aactcttctc    2820
tctctttctt ccccacaccc aagaggagga ttggtggtag ggggcaggca gaggggtgg    2880 ggagaagttt cctgggctcc atcaatggct gcatcttttc tggactcagc agtctccttg    2940
attccatgta gagtgtggaa aggagttgct gattgcattt cctctcatta acaattgggt    3000
gtgtaataaa aagcattgta cttcatctta aatcactggt aaggctcagc ctacagaaag    3060
atttgaaatg ccagagcca atcgcttggt gcattctgcg taatggtttc catctccgat    3120
ttcctcatca gggcctgtga atacccaggt gcctgtatct ttgccaagac cgtgatcaag    3180
gtagcttaag agagatggtc aggagaaaac actgttttg ttttttttgt tgttttgttt    3240
tgttttggcc agttaaatat catctctcaa atattgatct caccgtgtca accttgcact    3300
gcacaacctt ccttctgctt ctcccacacc cagtatttgc agaagggcaa agctgcttaa    3360
gagagaggat cagggtgaag tttggcacac agggtttatt aatggggcaa aaactgcctt    3420
ttcttcctcc tcctgacctt attttgctct tcactctccc cagccaataa agcgtctgtg    3480
gcgattggtg aacagcataa acagctggac ctcagcaagg gtcaggcaaa cccagtcact    3540
cggaaggcag ctgtgtgagc tgccaagcta gtgggcttca ggtgcaaggg tacctgtgcc    3600
acaccaacct gggagcacac agaatactat taatgtgcac ccagctggtc tccccaggca    3660
agaaggtatc ctcttcccaa ggtgtaccca ctgaatgttg ttactacata ttgagagtca    3720
ttttatgcat atgcattcta cctttcctgc tttatgagta ttttttaagct tttagttcaa    3780 ggttatattc agaaaatatt tcccagtata atgatacatc gtagcctaag aaatatttc    3840 tcaatgtaat tcccttccca gctacccaaa tgctacagag aaatgttttc tacttggcca    3900
ctatcagggt tcgtcatcta ttgtgttgac tattaatggc ttttgattg ggtaaggatt    3960 ttgctataga tgaaggtaga gggctgtcag ccctgaaaaa cacacaggtc agacatttaa    4020
```

```
aaggcatggg tttcgagctg tctcaaaata ttgcccaata gccataattt taccagcctt    4080
tctgtcatat gctgctatta caaagtggaa gctgttgaat gtttattggt gcccagggtt    4140
ttgctctcca atctaggttc agttgaagga atattgtttc taagactgtt ttgagacatg    4200
tccagtacat cacaaaggag atcggggcga cccctgcaga tgtggagcca ttagcccagt    4260
tgaggatatt ctccaagttg tcctctctcc tgctgatgga aatgggaatg aagttaagtg    4320
gtctgaaaaa cttgaatcgt tcacatttct cagctctggg ggtcatttac cagtttgttg    4380
tagaagaaat aatcaggtaa gttaaaagtt catttccaga gaaggtaaac cccacttacc    4440
atctctgcat gatttcagtg ggaattgatt atcactaatc cccaactggg ctagaataaa    4500
tgtaaagttt gaccttttta aaacgaaaag agagacaaag tctcagcaca ttccaaggag    4560
tggtagaaac agagctgaag gtgtccccat tgtagattag tctcttctca ctaaaattta    4620
ctttccaacg tagggcctaa aggaaacctt tcttaaagac aggctgaaac cccttcaaag    4680
gcagatgagg aggtacagac acgtgacctt ttggtgcaca ctggagctac ttggacaaga    4740
ccagcatgcc ttgctgcacg tgtgtgtatt tcactgctga aacatccttt taacttggtg    4800
tgcaatttga aaggatgtga atcatggatg gaaggccatt tgtacatgtc ccttggcaaa    4860
attctttctg gtgtctccta acttcagaga cagggactct ttttggatct ctattgacaa    4920
gtaataaaag tctggccctc ataacttgtt tccgaactag aaaagtctgt gagacccta    4980 catcattctg gttttttgc ttgagtaaga acaatccttt tttatttttc ttctgtacag    5040
tctaaagcta cagagaaaaa aaaatgcact cttcccttgc cggctcctgg taccattggt    5100
ctgaacagct gtagttggtc tactccttac ttagcacttg attgtgtggg gaaacaaagg    5160
tgggaggggt ggggaatact ggaaataatc agggcaattt ttttcttttcc cataattgga    5220 ctagatacct tggtactgtt gaccttctca gcatctccct tttgccttag atggcaacac    5280
cctccagtct gtagcagagc agtccaaccc agattagtgc agcccggagg cttagggtgc    5340
agcctccctg gtcttcctcc acacagttgt tcaccaacag accagacctc ctttaaccac    5400
agtgtcaaca tagtatcgga aagagagcca tttcttaggg gaataaaaca gtttcgcttc    5460
tttagctcat ctgtggtgtc agaatccttg gagctgaaga gagaaatcaa aagagcatga    5520
tgatggctgc ctggtttcag gtggaactta atgcattgat ctttagaagc tccttctgtt    5580
ggaagttgag tacctgtgat ctaaaatgtc ctggaggcag atgacatcta aaatatgtgc    5640
tttccaacca gcacagctgg cgctcttagc tcctgattgg ttgtgtgttt tattaaggat    5700
cagtgcagtt aagtcgtatt ttaaagtgtt acctcccctc ctaacccttc cccttcttgg    5760
acactgaagg aaaaggccaa ctagggtgtt agccctctgg gcaccaagga aactaacagc    5820
tttctcaaag cggtgaccac tcaggccagc ccagacaaat ctgagggatg gccagtgcac    5880
tccaatgatg ggacaggcct aacaacacat gtaagcttcc ccgagagctt tcagctggtt    5940
cacctctttg ttctctagac tcttaagtac tgactgcttt gacttttgtg attatgttat    6000
ggtgatgtgt agtcagtgta ccaatatgtt cacaacctag gatcatgata atggagtgtg    6060
ttttgggttt tttttaactg ttcagaaaaa aagtaaatta caaatataag attaagtga    6120 aaaaaaaaaa aaaaaaaaa aaaaaa                                         6146

<210> SEQ ID NO 3
<211> LENGTH: 2151
<212> TYPE: DNA
<213> ORGANISM: Homo sapiens

<400> SEQUENCE: 3
```

```
tgcgttggct gcggcctggc accaaagggg cggccccggc ggagagcgga cccagtggcc      60
tcggcgatta tggacccggc cgaggcggtg ctgcaagaga aggcactcaa gtttatgaat     120
tcctcagaga gagaagactg taataatggc gaaccccta ggaagataat accagagaag      180
aattcactta gacagacata acagctgt gccagactct gcttaaacca agaaacagta       240
tgtttagcaa gcactgctat gaagactgag aattgtgtgg ccaaaacaaa acttgccaat     300
ggcacttcca gtatgattgt gcccaagcaa cggaaactct cagcaagcta tgaaaaggaa     360
aaggaactgt gtgtcaaata ctttgagcag tggtcagagt cagatcaagt ggaatttgtg     420
gaacatctta tcccaaat gtgtcattac caacatgggc ataaactc gtatcttaaa         480
cctatgttgc agagagattt cataactgct ctgccagctc ggggattgga tcatatcgct     540
gagaacattc tgtcatacct ggatgccaaa tcactatgtg ctgctgaact tgtgtgcaag     600
gaatggtacc gagtgacctc tgatggcatg ctgtggaaga agcttatcga gagaatggtc     660
aggacagatt ctctgtggag aggcctggca gaacgaagag gatggggaca gtatttattc     720
aaaaacaaac tcctgacgg gaatgctcct cccaactctt tttatagagc actttatcct     780
aaaattatac aagacattga gacaaatgaa tctaattgga gatgtggaag acatagttta     840
cagagaattc actgccgaag tgaaacaagc aaaggagttt actgtttaca gtatgatgat     900
cagaaaatag taagcggcct tcgagacaac acaatcaaga tctgggataa aaacacattg     960
gaatgcaagc gaattctcac aggccataca ggttcagtcc tctgtctcca gtatgatgag    1020
agagtgatca taacaggatc atcggattcc acggtcagag tgtgggatgt aaatacaggt    1080
gaaatgctaa acacgttgat tcaccattgt gaagcagttc tgcacttgcg tttcaataat    1140
ggcatgatgg tgacctgctc caaagatcgt tccattgctg tatgggatat ggcctcccca    1200
actgacatta ccctccggag ggtgctggtc ggacaccgag ctgctgtcaa tgttgtagac    1260
tttgatgaca gtacattgt ttctgcatct ggggatagaa ctataaaggt atggaacaca     1320
agtacttgtg aatttgtaag gaccttaaat ggacacaaac gaggcattgc ctgtttgcag    1380
tacagggaca ggctggtagt gagtggctca tctgacaaca ctatcagatt atgggacata    1440
gaatgtggtg catgtttacg agtgttagaa ggccatgagg aattggtgcg ttgtattcga    1500
tttgataaca agaggatagt cagtggggcc tatgatggaa aaattaaagt gtgggatctt    1560
gtggctgctt ggaccccccg tgctcctgca gggacactct gtctacggac ccttgtggag    1620
cattccggaa gagtttttcg actacagttt gatgaattcc agattgtcag tagttcacat    1680
gatgacacaa tcctcatctg ggacttccta aatgatccag ctgcccaagc tgaaccccc    1740
cgttcccctt ctcgaacata cacctacatc tccagataaa taaccataca ctgacctcat    1800
acttgcccag gacccattaa agttgcggta tttaacgtat ctgccaatac caggatgagc    1860
aacaacagta acaatcaaac tactgcccag tttccctgga ctagccgagg agcagggctt    1920
tgagactcct gttgggacac agttggtctg cagtcggccc aggacggtct actcagcaca    1980
actgactgct tcagtgctgc tatcagaaga tgtcttctat caattgtgaa tgattggaac    2040
ttttaaacct cccctcctct cctccttca cctctgcacc tagtttttc ccattggttc      2100
cagacaaagg tgacttataa atatatttag tgttttgcca gaaaaaaaaa a             2151
```

<210> SEQ ID NO 4  
<211> LENGTH: 569  
<212> TYPE: PRT  
<213> ORGANISM: Homo sapiens

<400> SEQUENCE: 4

```
Met Asp Pro Ala Glu Ala Val Leu Gln Glu Lys Ala Leu Lys Phe Met
1               5                   10                  15

Asn Ser Ser Glu Arg Glu Asp Cys Asn Asn Gly Glu Pro Pro Arg Lys
            20                  25                  30

Ile Ile Pro Glu Lys Asn Ser Leu Arg Gln Thr Tyr Asn Ser Cys Ala
        35                  40                  45

Arg Leu Cys Leu Asn Gln Glu Thr Val Cys Leu Ala Ser Thr Ala Met
    50                  55                  60

Lys Thr Glu Asn Cys Val Ala Lys Thr Lys Leu Ala Asn Gly Thr Ser
65                  70                  75                  80

Ser Met Ile Val Pro Lys Gln Arg Lys Leu Ser Ala Ser Tyr Glu Lys
                85                  90                  95

Glu Lys Glu Leu Cys Val Lys Tyr Phe Glu Gln Trp Ser Glu Ser Asp
            100                 105                 110

Gln Val Glu Phe Val Glu His Leu Ile Ser Gln Met Cys His Tyr Gln
        115                 120                 125

His Gly His Ile Asn Ser Tyr Leu Lys Pro Met Leu Gln Arg Asp Phe
    130                 135                 140

Ile Thr Ala Leu Pro Ala Arg Gly Leu Asp His Ile Ala Glu Asn Ile
145                 150                 155                 160

Leu Ser Tyr Leu Asp Ala Lys Ser Leu Cys Ala Ala Glu Leu Val Cys
                165                 170                 175

Lys Glu Trp Tyr Arg Val Thr Ser Asp Gly Met Leu Trp Lys Lys Leu
            180                 185                 190

Ile Glu Arg Met Val Arg Thr Asp Ser Leu Trp Arg Gly Leu Ala Glu
        195                 200                 205

Arg Arg Gly Trp Gly Gln Tyr Leu Phe Lys Asn Lys Pro Pro Asp Gly
210                 215                 220

Asn Ala Pro Pro Asn Ser Phe Tyr Arg Ala Leu Tyr Pro Lys Ile Ile
225                 230                 235                 240

Gln Asp Ile Glu Thr Ile Glu Ser Asn Trp Arg Cys Gly Arg His Ser
            245                 250                 255

Leu Gln Arg Ile His Cys Arg Ser Glu Thr Ser Lys Gly Val Tyr Cys
        260                 265                 270

Leu Gln Tyr Asp Asp Gln Lys Ile Val Ser Gly Leu Arg Asp Asn Thr
    275                 280                 285

Ile Lys Ile Trp Asp Lys Asn Thr Leu Glu Cys Lys Arg Ile Leu Thr
290                 295                 300

Gly His Thr Gly Ser Val Leu Cys Leu Gln Tyr Asp Glu Arg Val Ile
305                 310                 315                 320

Ile Thr Gly Ser Ser Asp Ser Thr Val Arg Val Trp Asp Val Asn Thr
                325                 330                 335

Gly Glu Met Leu Asn Thr Leu Ile His His Cys Glu Ala Val Leu His
            340                 345                 350

Leu Arg Phe Asn Asn Gly Met Met Val Thr Cys Ser Lys Asp Arg Ser
        355                 360                 365

Ile Ala Val Trp Asp Met Ala Ser Pro Thr Asp Ile Thr Leu Arg Arg
    370                 375                 380

Val Leu Val Gly His Arg Ala Val Asn Val Val Asp Phe Asp Asp
385                 390                 395                 400

Lys Tyr Ile Val Ser Ala Ser Gly Asp Arg Thr Ile Lys Val Trp Asn
                405                 410                 415

Thr Ser Thr Cys Glu Phe Val Arg Thr Leu Asn Gly His Lys Arg Gly
```

```
                420               425               430
Ile Ala Cys Leu Gln Tyr Arg Asp Arg Leu Val Val Ser Gly Ser Ser
                435               440               445
Asp Asn Thr Ile Arg Leu Trp Asp Ile Glu Cys Gly Ala Cys Leu Arg
            450               455               460
Val Leu Glu Gly His Glu Glu Leu Val Arg Cys Ile Arg Phe Asp Asn
465               470               475               480
Lys Arg Ile Val Ser Gly Ala Tyr Asp Gly Lys Ile Lys Val Trp Asp
                485               490               495
Leu Val Ala Ala Leu Asp Pro Arg Ala Pro Ala Gly Thr Leu Cys Leu
                500               505               510
Arg Thr Leu Val Glu His Ser Gly Arg Val Phe Arg Leu Gln Phe Asp
            515               520               525
Glu Phe Gln Ile Val Ser Ser His Asp Asp Thr Ile Leu Ile Trp
            530               535               540
Asp Phe Leu Asn Asp Pro Ala Ala Gln Ala Glu Pro Pro Arg Ser Pro
545               550               555               560
Ser Arg Thr Tyr Thr Tyr Ile Ser Arg
                565

<210> SEQ ID NO 5
<211> LENGTH: 6013
<212> TYPE: DNA
<213> ORGANISM: Homo sapiens

<400> SEQUENCE: 5
taagagaggg cgggggaag gaagaggagg cgggatccgg gcgctgcgtt ggctgcggcc       60
tggcaccaaa gggcggccc cggcggagag cggacccagt ggcctcggcg attatggacc      120
cggccgaggc ggtgctgcaa gagaaggcac tcaagtttat gaattcctca gagagagaag    180
actgtaataa tggcgaaccc cctaggaaga taataccaga gaagaattca cttagacaga    240
catacaacag ctgtgccaga ctctgcttaa accaagaaac agtatgttta gcaagcactg    300
ctatgaagac tgagaattgt gtggccaaaa caaaacttgc caatggcact tccagtatga    360
ttgtgcccaa gcaacggaaa ctctcagcaa gctatgaaaa ggaaaaggaa ctgtgtgtca    420
aatactttga gcagtggtca gagtcagatc aagtggaatt tgtggaacat cttatatccc    480
aaatgtgtca ttaccaacat gggcacataa actcgtatct taaacctatg ttgcagagag    540
atttcataac tgctctgcca gctcggggat tggatcatat tgctgagaac attctgtcat    600
acctggatgc caaatcacta tgtgctgctg aacttgtgtg caaggaatgg taccgagtga    660
cctctgatgg catgctgtgg aagaagctta tcgagagaat ggtcaggaca gattctctgt    720
ggagaggcct ggcagaacga agaggatggg acagtatttt attcaaaaac aaacctcctg    780
acgggaatgc tcctcccaac tctttttata gagcacttta tcctaaaatt atacaagaca    840
ttgagacaat agaatctaat tggagatgtg aagacatag tttacagaga attcactgcc    900
gaagtgaaac aagcaaagga gtttactgtt tacagtatga tgatcagaaa atagtaagcg    960
gccttcgaga caacacaatc aagatctggg ataaaaacac attggaatgc aagcgaattc   1020
tcacaggcca tacaggttca gtcctctgtc tccagtatga tgagagagtg atcataacag   1080
gatcatcgga ttccacggtc agagtgtggg atgtaaaatac aggtgaaatg ctaaacacgt   1140
tgattcacca ttgtgaagca gttctgcact tgcgtttcaa taatggcatg atggtgacct   1200
gctccaaaga tcgttccatt gctgtatggg atatggcctc cccaactgac attaccctcc   1260
ggagggtgct ggtcggacac cgagctgctg tcaatgttgt agactttgat gacaagtaca   1320
```

```
ttgtttctgc atctggggat agaactataa aggtatggaa cacaagtact tgtgaatttg   1380
taaggacctt aaatggacac aaacgaggca ttgcctgttt gcagtacagg gacaggctgg   1440
tagtgagtgg ctcatctgac aacactatca gattatggga catagaatgt ggtgcatgtt   1500
tacgagtgtt agaaggccat gaggaattgg tgcgttgtat tcgatttgat aacaagagga   1560
tagtcagtgg ggcctatgat ggaaaaatta aagtgtggga tcttgtggct gctttggacc   1620
cccgtgctcc tgcagggaca ctctgtctac ggacccttgt ggagcattcc ggaagagttt   1680
ttcgactaca gtttgatgaa ttccagattg tcagtagttc acatgatgac acaatcctca   1740
tctgggactt cctaaatgat ccagctgccc aagctgaacc ccccgttcc ccttctcgaa    1800 catacaccta catctccaga taaataacca tacactgacc tcatacttgc ccaggaccca   1860
ttaaagttgc ggtatttaac gtatctgcca ataccaggat gagcaacaac agtaacaatc   1920
aaactactgc ccagtttccc tggactagcc gaggagcagg gctttgagac tcctgttggg   1980
acacagttgg tctgcagtcg gcccaggacg gtctactcag cacaactgac tgcttcagtg   2040
ctgctatcag aagatgtctt ctatctttg tgaatgattg gaactttaa acctcccctc     2100 ctctcctcct ttcacctctg cacctagttt tttcccattg gttccagaca aaggtgactt   2160
ataaatatat ttagtgtttt gccagaatct ctcttgcttt gccattaagc agaagaacta   2220
gtttccctgt atagcctgct gggagagacc cacttctagg gtatggggga tgcagcttca   2280
agcccagtgc ccagtgtctc cctgttaact gcaggaatgc caagcacctg ccagagcag    2340 cccagcccca atatgcttag gaggagacag agttccctct gtatagcctc tgggacaaga   2400 aaagaaaac acaagaatgt atacactgga agatttgggc ctcctgcctg ccttctcttt    2460
gtttctgttc ctcttcccat ctactcccct acgcccttc aacctttttt ctctgtctgc    2520
ttcacctgag aagaaagtgt acgaagagag tgtcctcctc tcacatgagc cagatcagcc   2580
agaaaatgca acacttggaa gagttaaatg ctgttcagtg aagatttcag ccccaggcct   2640
ttgctgcaag tgaccctgtg gcaacagtgg attctcagac atgatactct catcatattt   2700
gcaactcttc tctctctttc ttccccacac ccaagaggag gattggtggt aggggcagg    2760 cagaggggt ggggagaagt tcctgggct ccatcaatgg ctgcatcttt tctggactca     2820
gcagtctcct tgattccatg tagagtgtgg aaaggagttg ctgattgcat ttcctctcat   2880
taacaattgg gtgtgtaata aaaagcattg tacttcatct taaatcactg gtaaggctca   2940
gcctacagaa agatttgaaa tggccagagc caatcgcttg gtgcattctg cgtaatggtt   3000
tccatctccg atttcctcat cagggcctgt gaatacccag gtgcctgtat ctttgccaag   3060
accgtgatca aggtagctta agagagatgg tcaggagaaa acactgtttt tgtttttttt   3120
gttgttttgt tttgttttgg ccagttaaat atcatctctc aaatattgat ctcaccgtgt   3180
caaccttgca ctgcacaacc ttccttctgc ttctcccaca cccagtattt gcagaagggc   3240
aaagctgctt aagagagagg atcagggtga agtttggcac acagggttta ttaatgggc    3300 aaaaactgcc ttttcttcct cctcctgacc ttattttgct cttcactctc cccagccaat   3360
aaagcgtctg tggcgattgg tgaacagcat aaacagctgg acctcagcaa gggtcaggca   3420
aacccagtca ctcggaaggc agctgtgtga gctgccaagc tagtgggctt caggtgcaag   3480
ggtacctgtg ccacaccaac ctgggagcac acagaatact attaatgtgc acccagctgg   3540
tctccccagg caagaaggta tcctcttccc aaggtgtacc cactgaatgt tgttactaca   3600
tattgagagt cattttatgc atatgcattc tacctttcct gctttatgag tattttaag    3660 ctttttagttc aaggttatat tcagaaaata tttcccagta taatgataca tcgtagccta  3720
```

-continued

```
agaaatattt tctcaatgta attcccttcc cagctaccca aatgctacag agaaatgttt    3780
tctacttggc cactatcagg gttcgtcatc tattgtgttg actattaatg gcttttgat    3840
tgggtaagga ttttgctata gatgaaggta gagggctgtc agccctgaaa aacacacagg    3900
tcagacattt aaaaggcatg ggtttcgagc tgtctcaaaa tattgcccaa tagccataat    3960
tttaccagcc tttctgtcat atgctgctat tacaaagtgg aagctgttga atgtttattg    4020
gtgcccaggg ttttgctctc caatctaggt tcagttgaag gaatattgtt tctaagactg    4080
ttttgagaca tgtccagtac atcacaaagg agatcgggc gacccctgca gatgtggagc    4140
cattagccca gttgaggata ttctccaagt tgtcctctct cctgctgatg gaaatgggaa    4200
tgaagttaag tggtctgaaa aacttgaatc gttcacattt ctcagctctg ggggtcattt    4260
accagtttgt tgtagaagaa ataatcaggt aagttaaaag ttcatttcca gagaaggtaa    4320
accccactta ccatctctgc atgatttcag tgggaattga ttatcactaa tccccaactg    4380
ggctagaata aatgtaaagt ttgacctttt taaaacgaaa agagagacaa agtctcagca    4440
cattccaagg agtggtagaa acagagctga aggtgtcccc attgtagatt agtctcttct    4500
cactaaaatt tactttccaa cgtagggcct aaaggaaacc tttcttaaag acaggctgaa    4560
accccttcaa aggcagatga ggaggtacag acacgtgacc ttttggtgca cactggagct    4620
acttggacaa gaccagcatg ccttgctgca cgtgtgtgta tttcactgct gagaacatcc    4680
tttaacttgg tgtgcaattt gaaaggatgt gaatcatgga tggaaggcca tttgtacatg    4740
tcccttggca aaattctttc tggtgtctcc taacttcaga gacagggact ctttttggat    4800
ctctattgac aagtaataaa agtctggccc tcataacttg tttccgaact agaaaagtct    4860
gtgagacccc tacatcattc tggttttttt gcttgagtaa gaacaatcct tttttatttt    4920
tcttctgtac agtctaaagc tacagagaaa aaaaaatgca ctcttcccctt gccggctcct    4980
ggtaccattg gtctgaacag ctgtagttgg tctactcctt acttagcact tgattgtgtg    5040
gggaaacaaa ggtgggaggg gtggggaata ctggaaataa tcagggcaat ttttttcttt    5100
cccataattg gactagatac cttggtactg ttgaccttct cagcatctcc cttttgcctt    5160
agatggcaac ccctccagt ctgtagcaga gcagtccaac ccagattagt gcagcccgga    5220
ggcttagggt gcagcctccc tggtcttcct ccacacagtt gttcaccaac agaccagacc    5280
tcctttaacc acagtgtcaa catagtatcg gaaagagagc catttcttag gggaataaaa    5340
cagtttcgct tctttagctc atctgtggtg tcagaatcct tggagctgaa gagagaaatc    5400
aaaagagcat gatgatggct gcctggtttc aggtggaact taatgcattg atctttagaa    5460
gctccttctg ttggaagttg agtacctgtg atctaaaatg tcctggaggc agatgacatc    5520
taaaatatgt gctttccaac cagcacagct ggcgctctta gctcctgatt ggttgtgtgt    5580
tttattaagg atcagtgcag ttaagtcgta ttttaaagtg ttacctcccc tcctaaccct    5640
tccccttctt ggacactgaa ggaaaaggcc aactagggtg ttagccctct gggcaccaag    5700
gaaactaaca gctttctcaa agcggtgacc actcaggcca gcccagacaa atctgaggga    5760
tggccagtgc actccaatga tgggacaggc ctaacaacac atgtaagctt ccccgagagc    5820
tttcagctgg ttcacctctt tgttctctag actcttaagt actgactgct ttgacttttg    5880
tgattatgtt atggtgatgt gtagtcagtg taccaatatg ttcacaacct aggatcatga    5940
taatggagtg tgtttgggt ttttttaac tgttcagaaa aaagtaaat tacaaatata    6000
agattaaagt gaa                                                      6013
```

```
<210> SEQ ID NO 6
<211> LENGTH: 524
<212> TYPE: PRT
<213> ORGANISM: Homo sapiens

<400> SEQUENCE: 6

Met Glu Leu Gly Pro Glu Pro Pro His Arg Arg Leu Leu Phe Ala
1               5                   10                  15

Cys Ser Pro Pro Ala Ser Gln Pro Val Val Lys Ala Leu Phe Gly
                20                  25                  30

Ala Ser Ala Ala Gly Gly Leu Ser Pro Val Thr Asn Leu Thr Val
                35                  40                  45

Met Asp Gln Leu Gln Gly Leu Gly Ser Asp Tyr Glu Gln Pro Leu Glu
    50                  55                  60

Val Lys Asn Asn Ser Asn Leu Gln Arg Met Gly Ser Ser Glu Ser Thr
65                  70                  75                  80

Asp Ser Gly Phe Cys Leu Asp Ser Pro Gly Pro Leu Asp Ser Lys Glu
                85                  90                  95

Asn Leu Glu Asn Pro Met Arg Arg Ile His Ser Leu Pro Gln Lys Leu
                100                 105                 110

Leu Gly Cys Ser Pro Ala Leu Lys Arg Ser His Ser Asp Ser Leu Asp
                115                 120                 125

His Asp Ile Phe Gln Leu Ile Asp Pro Asp Glu Asn Lys Glu Asn Glu
                130                 135                 140

Ala Phe Glu Phe Lys Lys Pro Val Arg Pro Val Ser Arg Gly Cys Leu
145                 150                 155                 160

His Ser His Gly Leu Gln Gly Lys Asp Leu Phe Thr Gln Arg Gln
                165                 170                 175

Asn Ser Ala Pro Ala Arg Met Leu Ser Ser Asn Glu Arg Asp Ser Ser
                180                 185                 190

Glu Pro Gly Asn Phe Ile Pro Leu Phe Thr Pro Gln Ser Pro Val Thr
                195                 200                 205

Ala Thr Leu Ser Asp Glu Asp Asp Gly Phe Val Asp Leu Leu Asp Gly
                210                 215                 220

Glu Asn Leu Lys Asn Glu Glu Glu Thr Pro Ser Cys Met Ala Ser Leu
225                 230                 235                 240

Trp Thr Ala Pro Leu Val Met Arg Thr Thr Asn Leu Asp Asn Arg Cys
                245                 250                 255

Lys Leu Phe Asp Ser Pro Ser Leu Cys Ser Ser Ser Thr Arg Ser Val
                260                 265                 270

Leu Lys Arg Pro Glu Arg Ser Gln Glu Glu Ser Pro Pro Gly Ser Thr
                275                 280                 285

Lys Arg Arg Lys Ser Met Ser Gly Ala Ser Pro Lys Glu Ser Thr Asn
                290                 295                 300

Pro Glu Lys Ala His Glu Thr Leu His Gln Ser Leu Ser Leu Ala Ser
305                 310                 315                 320

Ser Pro Lys Gly Thr Ile Glu Asn Ile Leu Asp Asn Asp Pro Arg Asp
                325                 330                 335

Leu Ile Gly Asp Phe Ser Lys Gly Tyr Leu Phe His Thr Val Ala Gly
                340                 345                 350

Lys His Gln Asp Leu Lys Tyr Ile Ser Pro Glu Ile Met Ala Ser Val
                355                 360                 365

Leu Asn Gly Lys Phe Ala Asn Leu Ile Lys Glu Phe Val Ile Ile Asp
                370                 375                 380

Cys Arg Tyr Pro Tyr Glu Tyr Glu Gly Gly His Ile Lys Gly Ala Val
```

```
                385                 390                 395                 400
Asn Leu His Met Glu Glu Val Glu Asp Phe Leu Leu Lys Lys Pro
                    405                 410                 415

Ile Val Pro Thr Asp Gly Lys Arg Val Ile Val Val Phe His Cys Glu
                420                 425                 430

Phe Ser Ser Glu Arg Gly Pro Arg Met Cys Arg Tyr Val Arg Glu Arg
            435                 440                 445

Asp Arg Leu Gly Asn Glu Tyr Pro Lys Leu His Tyr Pro Glu Leu Tyr
        450                 455                 460

Val Leu Lys Gly Gly Tyr Lys Glu Phe Phe Met Lys Cys Gln Ser Tyr
465                 470                 475                 480

Cys Glu Pro Pro Ser Tyr Arg Pro Met His His Glu Asp Phe Lys Glu
                485                 490                 495

Asp Leu Lys Lys Phe Arg Thr Lys Ser Arg Thr Trp Ala Gly Glu Lys
                500                 505                 510

Ser Lys Arg Glu Met Tyr Ser Arg Leu Lys Lys Leu
                515                 520

<210> SEQ ID NO 7
<211> LENGTH: 3717
<212> TYPE: DNA
<213> ORGANISM: Homo sapiens

<400> SEQUENCE: 7
gaacagcgaa gacagcgtga gcctgggccg ttgcctcgag gctctcgccc ggcttctctt      60
gccgacccgc cacgtttgtt tggatttaat cttcaggttg ccggcgcccg cccgcccgct     120
ggcctcgcgg tgtgagaggg aagcacccgt gcctgtggct ggtggctggc gcctggaggg     180
tccgcacacc cgcccggccg cgccgcttgc ccgcggcagc cgcgtccctg aaccgcggag     240
tcgtgtttgt gtttgacccc cgggcgccgg tggcgcgcgg ccgaggccgg tgtcggcggg     300
gcggggcggt cgcggcggag gcagaggaag agggagcggg agctctgcga ggccgggcgc     360
cgccatggaa ctgggcccgg agcccccgca ccgccgccgc ctgctcttcg cctgcagccc     420
ccctcccgcg tcgcagcccg tcgtgaaggc gctatttggc gcttcagccg ccggggggact     480 gtcgcctgtc accaacctga ccgtcactat ggaccagctg cagggtctgg gcagtgatta     540
tgagcaacca ctggaggtga gaacaacag taatctgcag agaatgggct cctccgagtc     600
aacagattca ggtttctgtc tagattctcc tgggccattg acagtaaag aaaaccttga     660 aaatcctatg agaagaatac attccctacc tcagaagctg ttgggatgta gtccagctct     720
gaagaggagc cattctgatt ctcttgacca tgacatcttt cagctcatcg acccagatga     780
gaacaaggaa aatgaagcct tgagtttaa aagccagta agacctgtat ctcgtggctg     840
cctgcactct catggactcc aggagggtaa agatctcttc acacagaggc agaactctgc     900
cccagctcgg atgctttcct caaatgaaag agatagcagt gaaccaggga atttcattcc     960 tcttttttaca ccccagtcac ctgtgacagc cactttgtct gatgaggatg atggcttcgt    1020
ggaccttctc gatggagaga atctgaagaa tgaggaggag accccctcgt gcatggcaag    1080
cctctggaca gctcctctcg tcatgagaac tacaaaccct gacaaccgat gcaagctgtt    1140 tgactccccct tccctgtgta gctccagcac tcggtcagtg ttgaagagac agaaccgatc    1200
tcaagaggag tctccacctg gaagtacaaa gaggaggaag agcatgtctg gggccagccc    1260
caaagagtca actaatccag agaaggccca tgagactctt catcagtctt tatccctggc    1320
atcttccccc aaaggaacca ttgagaacat tttggacaat gacccaaggg accttatagg    1380
```

```
agacttctcc aagggttatc tctttcatac agttgctggg aaacatcagg atttaaaata    1440
catctctcca gaaattatgg catctgtttt gaatggcaag tttgccaacc tcattaaaga    1500
gtttgttatc atcgactgtc gatacccata tgaatacgag ggaggccaca tcaagggtgc    1560
agtgaacttg cacatggaag aagaggttga agacttctta ttgaagaagc ccattgtacc    1620
tactgatggc aagcgtgtca ttgttgtgtt tcactgcgag ttttcttctg agagaggtcc    1680
ccgcatgtgc cggtatgtga gagagagaga tcgcctgggt aatgaatacc ccaaactcca    1740
ctaccctgag ctgtatgtcc tgaaggggg  atacaaggag ttctttatga aatgccagtc    1800
ttactgtgag ccccctagct accggcccat gcaccacgag gactttaaag aagacctgaa    1860
gaagttccgc accaagagcc ggacctgggc aggggagaag agcaagaggg agatgtacag    1920
tcgtctgaag aagctctgag gcggcagga  ccagccagca gcagcccaag cttccctcca    1980
tccccctttta ccctctttgc tgcagagaaa cttaagcaaa ggggacagct gtgtgacatt    2040
tggagagggg gcctgggact tccatgcctt aaacctacct cccacactcc caaggttgga    2100
gcccagggca tcttgctggc tacgcctctt ctgtccctgt tagacgtcct ccgtccatat    2160
cagaactgtg ccacaatgca gttctgagca ccgtgtcaag ctgctctgag ccacagtggg    2220
atgaaccagc cggggcctta tcgggctcca gccatctcat gaggggagag gagacggagg    2280
ggagtagaga agttacacag aaatgctgct ggccaaatag caaagacaac ctgggaagga    2340
aaggtctttg tgggataatc catatgttta atttattcaa cttcatcaat cactttattt    2400
tattttttt  tctaactcct ggagacttat tttactgctt cattaggttg aaatactgcc    2460
attctaggta gggtttttatt atcccaggga ctacctcggc ttttaattta aaaaaaaaaa    2520
agaagtgggt aagaaaatgc aaacctgtta taagttatcg gacagaaagc taggtgctct    2580
gtcaccccca ggaggcgctg tggtactggg gctgctgcta tttaagccaa gaactgaggt    2640
cctggtgaga gcgttggacc caggcttggc tgcctgacat aagctaaatc tcccagaccc    2700
accactggct accgatatct atttggtggg aggtgtggcc ctgttcttcc tcaccccagt    2760
tccatgacat tggctggtat aggagccaca gtcaggaaag cacttgaggc agcatctgtt    2820
gggccacccc cggctcagtg ctggaatgtt gcagtgtagg tttcccaggg aaggggggtg    2880
ggggtaggtg ggctccacag gatgggggag gagcatgtcc actgagtatc ttccttatgt    2940
tgctgtgata ttgatagctt ttattttcta atttttaaaa aatggtcata ttatgagtca    3000
aagagtatca aatcagtgtt ggatggacca cccaagggtg aggagagggg ctggaagccc    3060
tgggcattag gagaagggag tgggtgctgg catggacatg actggataga attttctcag    3120
gagggagctt ggtggatttt gaaggtaaaa cttttctgggt ttatcatgtt ttaattttag    3180
agacaggag  tgatgaatca tcaccggttg tccccttatc taactccata aaagtgggaa    3240
tttcaaaaga acacctcatc caaggagctg gggcagactt cattgattct agagagacct    3300
gtttcagtgc ctactcatcc ctgccctctg gtgccagcct ccttaccatc acggcttcac    3360
tgaggtgtag gtgggttttt cttaaacagg agacagtctc tccctcttaa cctcaacttc    3420
ttggggtggg aatcagtgat actggagatg gctagttgct gtgttacggg tttgagttac    3480
atttggctat aaaacaatct tgttgggaaa aatgtggggg agaggacttc ttcctacacg    3540
cgcattgaga cagattccaa ctggttaatg atattgtttg taagaaagag attctgttgg    3600
ttgactgcct aaagagaaag gtgggatggc cttcagatta taccagctta gctagcatta    3660
ctaaccaact gttggaagct ctgaaaataa aagatcttga acccataaaa aaaaaaa      3717
```

<210> SEQ ID NO 8

<211> LENGTH: 4299
<212> TYPE: DNA
<213> ORGANISM: Homo sapiens

<400> SEQUENCE: 8

```
atgacaggcg aggtgggttc tgaggttcac ctagaaatca atgacccaaa cgtcatttca     60
caagaggaag cagatagtcc ttcagatagt ggacagggca gctatgaaac aattggaccc    120
ttgagtgaag gagattcaga tgaagagata tttgtaagta agaagttgaa aaacaggaag    180
gttctacaag acagtgattc cgaaacagag gacacaaatg cctctccaga gaaaactacc    240
tatgacagtg ccgaggagga aaataaagag aatttatatg ctgggaaaaa tacaaaaatc    300
aaaaggattt acaaaactgt ggcagacagt gatgaaagtt acatggaaaa gtctttgtat    360
caggaaaatc ttgaagcgca agtgaaacct tgcttagagc tgagtcttca gtctggaaac    420
tctacagact ttaccactga cagaaagagt tccaaaaagc acatacatga taagaaggga    480
actgcaggaa aagcaaaagt aaaatcaaaa agaagacttg agaagaggaa gagaaaaatg    540
gaaaaaatta gacagctaaa aaagaaggaa acaaaaaacc aggaagatga tgtagaacag    600
ccatttaatg acagtggctg tcttcttgtg gataaagacc ttttgaaac tgggttggag    660
gatgaaaata actctccatt ggaagatgaa gagtcattag aatcaataag agcagctgta    720
aaaaacaaag taaaaaagca caagaaaaaa gaaccatctt tggagagtgg ggtccattca    780
tttgaggaag aagtgagtt atcaaaagga accacgagga aggaaagaaa ggcagccaga    840
ttaagtaaag aagcattaaa acaactgcat agtgagactc agcgccttat tcgagagtct    900
gcactgaacc ttccatatca tatgcctgag aataaaacca ttcatgattt cttcaaacgt    960
aaacccggc ccacttgcca cggaaatgcc atggcactat tgaagtcatc taaatatcag   1020
tcaagccatc acaaagaaat catagacact gcaaatacta ctgaaatgaa cagtgatcac   1080
catagtaaag gttctgagca gacaacaggt gcagaaaatg aagtggaaac taatgcactc   1140
cctgtagttt caaaggaaac ccagatcatt actggatcag atgagtcttg caggaaggat   1200
ttggtaaaaa atgaagagct agaaattcag gagaaacaga agcagagtga cattagacct   1260
tcacctgggg acagctcagt gttgcaacag gaatccaact tcctcgggaa caatcacagt   1320
gaggaatgtc aggttggagg gcttgtagca tttgaacctc atgccctgga gggtgaaggc   1380
ccccaaaatc cagaagaaac agatgagaaa gtggaagagc tgagcagca aaataaatca   1440
tcagcagttg ggccacctga aaaagtgaga cggtttactc tggatagact taagcaactg   1500
ggagtagatg tttccattaa ccacggcta ggtgctgatg aagattcctt tgtgatactt   1560
gaacctgaaa ccaacagaga actggaagcc ttgaagcagc gtttctggaa gcatgctaat   1620
ccagcagcca acccagggc tggtcagaca gtgaatgtga acgtcatagt gaaagacatg   1680
ggcactgatg gaaaggaaga gctaaaagca gatgtggtac ctgtgacttt agcacctaag   1740
aagttggatg gagcaagcca cacaaaacca ggtgaaaagc ttcaggtgtt aaaagctaaa   1800
ctgcaagaag caatgaaact ccgaaggttt gaggagcgcc agaagcgcca agcactgttt   1860
aaattagata tgaagatgg gtttgaggaa gaggaggagg aagaggaaga atgacagat   1920
gagtctgagg aagatggaga agagaaggta gagaaagaag agaaagagga gaactagag   1980
gaagaggagg agaagaagaa ggaggaggaa gaagaaggaa atcaggagac tgcagaattc   2040
cttcttagta gtgaagaaat agaaacaaaa gatgaaaaag aaatggataa agaaaataat   2100
gatggcagta gtgaaattgg caaggcagtt ggcttcctct ctgttcccaa gtctctctca   2160
tcagattcta ctttacttct gtttaaggac agctcttcca agatgggtta ctttcctact   2220
```

| | | |
|---|---|---|
| gaagaaaaat cagaaacaga tgaaaactca ggcaagcagc ctagcaaact ggatgaggat | 2280 | |
| gattcatgtt cattgctaac aaaggagagc agccacaata gcagctttga gctgattggc | 2340 | |
| tccacgattc catcctatca gccttgcaac agacaaacag gccgtgggac cagttttttc | 2400 | |
| cctacagcag gaggattcag atctccttcc cctgggctat ttcgagccag tttggtcagc | 2460 | |
| tcagcttcta agagttcagg gaaactgtct gagccttcac ttcccataga ggattcccag | 2520 | |
| gatctgtata acgcctcccc agagcctaag acacttttcc taggagcagg agacttccag | 2580 | |
| ttctgtttag aagatgacac tcagagccaa ctgttggatg cagatgggtt cttaaatgtt | 2640 | |
| agaaaccaca ggaatcagta ccaagctttg aagcctcgat tgccattggc cagtatggat | 2700 | |
| gagaatgcca tggatgccaa catggatgag ctgttggatt tgtgtactgg aaagttcaca | 2760 | |
| tctcaggctg aaaaacatct acccaggaag agtgacaaga aagagaacat ggaggaactt | 2820 | |
| ctgaaccttt gttcaggaaa attcacttct caggatgcct ccactccagc ctcatcagag | 2880 | |
| ttaaataaac aggagaagga gagcagcatg ggtgatccaa tggaagaagc acttgctctt | 2940 | |
| tgctcaggct cttttcccac agacaaggaa gaggaagacg aggaggagga atttggagac | 3000 | |
| tttcggcttg tttcaaatga taatgagttt gatagtgatg aggatgaaca cagtgactct | 3060 | |
| ggtaatgatc tggcactgga agaccatgaa gatgatgatg aagaagaact cctgaagcga | 3120 | |
| tctgagaagt tgaaaaggca aatgaggttg aggaaatacc tggaggatga ggcagaggtg | 3180 | |
| tcaggaagtg atgtgggaag cgaagatgag tatgatgggg aagaaattga tgaatatgaa | 3240 | |
| gaggacgtaa ttgatgaagt acttccttct gatgaggaac tgcagagtca aatcaagaaa | 3300 | |
| atacacatga aaactatgtt ggatgatgat aagcgacagc tacgtttata ccaagagagg | 3360 | |
| taccttgctg atggggatct gcacagcgat ggtcctgggc gaatgaggaa gtttcgatgg | 3420 | |
| aaaaacatag atgatgcttc ccagatggac ttgttccaca gagactctga tgatgatcag | 3480 | |
| actgaagaac agcttgatga gtcagaagcc aggtggagga aggagcgaat tgaacgagag | 3540 | |
| cagtggcttc gggacatggc acagcagggg aaaattacag ctgaagaaga agaagaaatt | 3600 | |
| ggggaggaca gtcagtttat gatactggcc aagaaagtta cagccaaagc actgcagaag | 3660 | |
| aatgccagtc gccctatggt tattcaggaa tcaaagtctt tgctcagaaa tccttttgaa | 3720 | |
| gccatcagac caggaagtgc tcaacaggtg aagacaggct cactgctaaa ccagcccaaa | 3780 | |
| gctgtgcttc agaaactggc tgctctctct gaccataacc ccagtgctcc tcgaaattca | 3840 | |
| agaaactttg tctttcatac actttctcct gtcaaggctg aggcggcaaa ggaatcgtct | 3900 | |
| aagtctcagg taaagaaaag gggtccatct ttcatgactt ctccttcacc taagcacctc | 3960 | |
| aaaacagatg atagcacttc aggattgacg cgaagcatct tcaaatattt ggagagctaa | 4020 | |
| caccatcaaa ggtgccaaaa tctacattga gactgctttg agaagtttct agcactgaaa | 4080 | |
| gttggaattg acactccagc caatgatcct tccttctttc ataatcaatg caataagatt | 4140 | |
| gcagacagaa attccagtga tttctactgc acagctctgg acatctcttt tcctagtatt | 4200 | |
| attccctgaa ttggccactg atttcaattc tgcagtattt acaacatcaa caactcatgg | 4260 | |
| aatacttggg tgaggtttcc ttttttttt ttttttttaa | 4299 | |

<210> SEQ ID NO 9
<211> LENGTH: 1339
<212> TYPE: PRT
<213> ORGANISM: Homo sapiens

<400> SEQUENCE: 9

Met Thr Gly Glu Val Gly Ser Glu Val His Leu Glu Ile Asn Asp Pro
1               5                   10                  15

```
Asn Val Ile Ser Gln Glu Glu Ala Asp Ser Pro Ser Asp Ser Gly Gln
            20                  25                  30

Gly Ser Tyr Glu Thr Ile Gly Pro Leu Ser Glu Gly Asp Ser Asp Glu
            35                  40                  45

Glu Ile Phe Val Ser Lys Lys Leu Lys Asn Arg Lys Val Leu Gln Asp
 50                  55                  60

Ser Asp Ser Glu Thr Glu Asp Thr Asn Ala Ser Pro Glu Lys Thr Thr
 65                  70                  75                  80

Tyr Asp Ser Ala Glu Glu Asn Lys Glu Asn Leu Tyr Ala Gly Lys
                85                  90                  95

Asn Thr Lys Ile Lys Arg Ile Tyr Lys Thr Val Ala Asp Ser Asp Glu
            100                 105                 110

Ser Tyr Met Glu Lys Ser Leu Tyr Gln Glu Asn Leu Glu Ala Gln Val
            115                 120                 125

Lys Pro Cys Leu Glu Leu Ser Leu Gln Ser Gly Asn Ser Thr Asp Phe
            130                 135                 140

Thr Thr Asp Arg Lys Ser Ser Lys Lys His Ile His Asp Lys Glu Gly
145                 150                 155                 160

Thr Ala Gly Lys Ala Lys Val Lys Ser Lys Arg Arg Leu Glu Lys Glu
                165                 170                 175

Glu Arg Lys Met Glu Lys Ile Arg Gln Leu Lys Lys Glu Thr Lys
            180                 185                 190

Asn Gln Glu Asp Asp Val Glu Gln Pro Phe Asn Asp Ser Gly Cys Leu
            195                 200                 205

Leu Val Asp Lys Asp Leu Phe Glu Thr Gly Leu Glu Asp Glu Asn Asn
210                 215                 220

Ser Pro Leu Glu Asp Glu Ser Leu Glu Ser Ile Arg Ala Ala Val
225                 230                 235                 240

Lys Asn Lys Val Lys Lys His Lys Lys Lys Glu Pro Ser Leu Glu Ser
            245                 250                 255

Gly Val His Ser Phe Glu Gly Ser Glu Leu Ser Lys Gly Thr Thr
            260                 265                 270

Arg Lys Glu Arg Lys Ala Ala Arg Leu Ser Lys Glu Ala Leu Lys Gln
            275                 280                 285

Leu His Ser Glu Thr Gln Arg Leu Ile Arg Glu Ser Ala Leu Asn Leu
            290                 295                 300

Pro Tyr His Met Pro Glu Asn Lys Thr Ile His Asp Phe Phe Lys Arg
305                 310                 315                 320

Lys Pro Arg Pro Thr Cys His Gly Asn Ala Met Ala Leu Leu Lys Ser
            325                 330                 335

Ser Lys Tyr Gln Ser Ser His His Lys Glu Ile Ile Asp Thr Ala Asn
            340                 345                 350

Thr Thr Glu Met Asn Ser Asp His His Ser Lys Gly Ser Glu Gln Thr
            355                 360                 365

Thr Gly Ala Glu Asn Glu Val Glu Thr Asn Ala Leu Pro Val Val Ser
            370                 375                 380

Lys Glu Thr Gln Ile Ile Thr Gly Ser Asp Glu Ser Cys Arg Lys Asp
385                 390                 395                 400

Leu Val Lys Asn Glu Glu Leu Glu Ile Gln Lys Gln Lys Gln Ser
            405                 410                 415

Asp Ile Arg Pro Ser Pro Gly Asp Ser Ser Val Leu Gln Gln Glu Ser
            420                 425                 430

Asn Phe Leu Gly Asn Asn His Ser Glu Glu Cys Gln Val Gly Gly Leu
```

```
                435                 440                 445
Val Ala Phe Glu Pro His Ala Leu Glu Gly Glu Gly Pro Gln Asn Pro
450                 455                 460
Glu Glu Thr Asp Glu Lys Val Glu Pro Glu Gln Gln Asn Lys Ser
465                 470                 475                 480
Ser Ala Val Gly Pro Pro Glu Lys Val Arg Arg Phe Thr Leu Asp Arg
            485                 490                 495
Leu Lys Gln Leu Gly Val Asp Val Ser Ile Lys Pro Arg Leu Gly Ala
                500                 505                 510
Asp Glu Asp Ser Phe Val Ile Leu Glu Pro Glu Thr Asn Arg Glu Leu
            515                 520                 525
Glu Ala Leu Lys Gln Arg Phe Trp Lys His Ala Asn Pro Ala Ala Lys
530                 535                 540
Pro Arg Ala Gly Gln Thr Val Asn Val Asn Val Ile Val Lys Asp Met
545                 550                 555                 560
Gly Thr Asp Gly Lys Glu Glu Leu Lys Ala Asp Val Val Pro Val Thr
            565                 570                 575
Leu Ala Pro Lys Lys Leu Asp Gly Ala Ser His Thr Lys Pro Gly Glu
                580                 585                 590
Lys Leu Gln Val Leu Lys Ala Lys Leu Gln Glu Ala Met Lys Leu Arg
            595                 600                 605
Arg Phe Glu Glu Arg Gln Lys Arg Gln Ala Leu Phe Lys Leu Asp Asn
610                 615                 620
Glu Asp Gly Phe Glu Glu Glu Glu Glu Glu Glu Met Thr Asp
625                 630                 635                 640
Glu Ser Glu Glu Asp Gly Glu Glu Lys Val Glu Lys Glu Glu Lys Glu
            645                 650                 655
Glu Glu Leu Glu Glu Glu Glu Glu Lys Glu Glu Glu Glu Glu Glu
                660                 665                 670
Gly Asn Gln Glu Thr Ala Glu Phe Leu Leu Ser Ser Gly Glu Ile Glu
            675                 680                 685
Thr Lys Asp Glu Lys Glu Met Asp Lys Glu Asn Asn Asp Gly Ser Ser
690                 695                 700
Glu Ile Gly Lys Ala Val Gly Phe Leu Ser Val Pro Lys Ser Leu Ser
705                 710                 715                 720
Ser Asp Ser Thr Leu Leu Phe Lys Asp Ser Ser Lys Met Gly
            725                 730                 735
Tyr Phe Pro Thr Glu Glu Lys Ser Glu Thr Asp Glu Asn Ser Gly Lys
                740                 745                 750
Gln Pro Ser Lys Leu Asp Glu Asp Ser Cys Ser Leu Leu Thr Lys
            755                 760                 765
Glu Ser Ser His Asn Ser Ser Phe Glu Leu Ile Gly Ser Thr Ile Pro
770                 775                 780
Ser Tyr Gln Pro Cys Asn Arg Gln Thr Gly Arg Gly Thr Ser Phe Phe
785                 790                 795                 800
Pro Thr Ala Gly Gly Phe Arg Ser Pro Ser Pro Gly Leu Phe Arg Ala
            805                 810                 815
Ser Leu Val Ser Ser Ala Ser Lys Ser Ser Gly Lys Leu Ser Glu Pro
                820                 825                 830
Ser Leu Pro Ile Glu Asp Ser Gln Asp Leu Tyr Asn Ala Ser Pro Glu
            835                 840                 845
Pro Lys Thr Leu Phe Leu Gly Ala Gly Asp Phe Gln Phe Cys Leu Glu
850                 855                 860
```

-continued

Asp Asp Thr Gln Ser Gln Leu Leu Asp Ala Asp Gly Phe Leu Asn Val
865                 870                 875                 880

Arg Asn His Arg Asn Gln Tyr Gln Ala Leu Lys Pro Arg Leu Pro Leu
                885                 890                 895

Ala Ser Met Asp Glu Asn Ala Met Asp Ala Asn Met Asp Glu Leu Leu
            900                 905                 910

Asp Leu Cys Thr Gly Lys Phe Thr Ser Gln Ala Glu Lys His Leu Pro
        915                 920                 925

Arg Lys Ser Asp Lys Lys Glu Asn Met Glu Glu Leu Leu Asn Leu Cys
    930                 935                 940

Ser Gly Lys Phe Thr Ser Gln Asp Ala Ser Thr Pro Ala Ser Ser Glu
945                 950                 955                 960

Leu Asn Lys Gln Glu Lys Glu Ser Ser Met Gly Asp Pro Met Glu Glu
                965                 970                 975

Ala Leu Ala Leu Cys Ser Gly Ser Phe Pro Thr Asp Lys Glu Glu Glu
            980                 985                 990

Asp Glu Glu Glu Glu Phe Gly Asp Phe Arg Leu Val Ser Asn Asp Asn
        995                 1000                1005

Glu Phe Asp Ser Asp Glu Asp Glu His Ser Asp Ser Gly Asn Asp
    1010                1015                1020

Leu Ala Leu Glu Asp His Glu Asp Asp Glu Glu Glu Leu Leu
    1025                1030                1035

Lys Arg Ser Glu Lys Leu Lys Arg Gln Met Arg Leu Arg Lys Tyr
    1040                1045                1050

Leu Glu Asp Glu Ala Glu Val Ser Gly Ser Asp Val Gly Ser Glu
    1055                1060                1065

Asp Glu Tyr Asp Gly Glu Glu Ile Asp Glu Tyr Glu Glu Asp Val
    1070                1075                1080

Ile Asp Glu Val Leu Pro Ser Asp Glu Glu Leu Gln Ser Gln Ile
    1085                1090                1095

Lys Lys Ile His Met Lys Thr Met Leu Asp Asp Asp Lys Arg Gln
    1100                1105                1110

Leu Arg Leu Tyr Gln Glu Arg Tyr Leu Ala Asp Gly Asp Leu His
    1115                1120                1125

Ser Asp Gly Pro Gly Arg Met Arg Lys Phe Arg Trp Lys Asn Ile
    1130                1135                1140

Asp Asp Ala Ser Gln Met Asp Leu Phe His Arg Asp Ser Asp Asp
    1145                1150                1155

Asp Gln Thr Glu Glu Gln Leu Asp Glu Ser Glu Ala Arg Trp Arg
    1160                1165                1170

Lys Glu Arg Ile Glu Arg Glu Gln Trp Leu Arg Asp Met Ala Gln
    1175                1180                1185

Gln Gly Lys Ile Thr Ala Glu Glu Glu Glu Ile Gly Glu Asp
    1190                1195                1200

Ser Gln Phe Met Ile Leu Ala Lys Lys Val Thr Ala Lys Ala Leu
    1205                1210                1215

Gln Lys Asn Ala Ser Arg Pro Met Val Ile Gln Glu Ser Lys Ser
    1220                1225                1230

Leu Leu Arg Asn Pro Phe Glu Ala Ile Arg Pro Gly Ser Ala Gln
    1235                1240                1245

Gln Val Lys Thr Gly Ser Leu Leu Asn Gln Pro Lys Ala Val Leu
    1250                1255                1260

Gln Lys Leu Ala Ala Leu Ser Asp His Asn Pro Ser Ala Pro Arg
    1265                1270                1275

```
Asn Ser Arg Asn Phe Val Phe His Thr Leu Ser Pro Val Lys Ala
    1280                1285                1290

Glu Ala Ala Lys Glu Ser Ser Lys Ser Gln Val Lys Lys Arg Gly
    1295                1300                1305

Pro Ser Phe Met Thr Ser Pro Ser Pro Lys His Leu Lys Thr Asp
    1310                1315                1320

Asp Ser Thr Ser Gly Leu Thr Arg Ser Ile Phe Lys Tyr Leu Glu
    1325                1330                1335

Ser

<210> SEQ ID NO 10
<211> LENGTH: 493
<212> TYPE: PRT
<213> ORGANISM: Homo sapiens

<400> SEQUENCE: 10

Met Asp Gln Asp Tyr Glu Arg Arg Leu Leu Arg Gln Ile Val Ile Gln
1               5                   10                  15

Asn Glu Asn Thr Met Pro Arg Val Thr Glu Met Arg Arg Thr Leu Thr
                20                  25                  30

Pro Ala Ser Ser Pro Val Ser Ser Pro Ser Lys His Gly Asp Arg Phe
            35                  40                  45

Ile Pro Ser Arg Ala Gly Ala Asn Trp Ser Val Asn Phe His Arg Ile
    50                  55                  60

Asn Glu Asn Glu Lys Ser Pro Ser Gln Asn Arg Lys Ala Lys Asp Ala
65                  70                  75                  80

Thr Ser Asp Asn Gly Lys Asp Gly Leu Ala Tyr Ser Ala Leu Leu Lys
                85                  90                  95

Asn Glu Leu Leu Gly Ala Gly Ile Glu Lys Val Gln Asp Pro Gln Thr
            100                 105                 110

Glu Asp Arg Arg Leu Gln Pro Ser Thr Pro Glu Lys Lys Gly Leu Phe
        115                 120                 125

Thr Tyr Ser Leu Ser Thr Lys Arg Ser Ser Pro Asp Asp Gly Asn Asp
130                 135                 140

Val Ser Pro Tyr Ser Leu Ser Pro Val Ser Asn Lys Ser Gln Lys Leu
145                 150                 155                 160

Leu Arg Ser Pro Arg Lys Pro Thr Arg Lys Ile Ser Lys Ile Pro Phe
                165                 170                 175

Lys Val Leu Asp Ala Pro Glu Leu Gln Asp Asp Phe Tyr Leu Asn Leu
            180                 185                 190

Val Asp Trp Ser Ser Leu Asn Val Leu Ser Val Gly Leu Gly Thr Cys
        195                 200                 205

Val Tyr Leu Trp Ser Ala Cys Thr Ser Gln Val Thr Arg Leu Cys Asp
    210                 215                 220

Leu Ser Val Glu Gly Asp Ser Val Thr Ser Val Gly Trp Ser Glu Arg
225                 230                 235                 240

Gly Asn Leu Val Ala Val Gly Thr His Lys Gly Phe Val Gln Ile Trp
                245                 250                 255

Asp Ala Ala Ala Gly Lys Lys Leu Ser Met Leu Glu Gly His Thr Ala
            260                 265                 270

Arg Val Gly Ala Leu Ala Trp Asn Ala Glu Gln Leu Ser Ser Gly Ser
        275                 280                 285

Arg Asp Arg Met Ile Leu Gln Arg Asp Ile Arg Thr Pro Pro Leu Gln
    290                 295                 300
```

```
Ser Glu Arg Arg Leu Gln Gly His Arg Gln Glu Val Cys Gly Leu Lys
305                 310                 315                 320

Trp Ser Thr Asp His Gln Leu Leu Ala Ser Gly Gly Asn Asp Asn Lys
            325                 330                 335

Leu Leu Val Trp Asn His Ser Ser Leu Ser Pro Val Gln Gln Tyr Thr
            340                 345                 350

Glu His Leu Ala Ala Val Lys Ala Ile Ala Trp Ser Pro His Gln His
            355                 360                 365

Gly Leu Leu Ala Ser Gly Gly Thr Ala Asp Arg Cys Ile Arg Phe
370                 375                 380

Trp Asn Thr Leu Thr Gly Gln Pro Leu Gln Cys Ile Asp Thr Gly Ser
385                 390                 395                 400

Gln Val Cys Asn Leu Ala Trp Ser Lys His Ala Asn Glu Leu Val Ser
            405                 410                 415

Thr His Gly Tyr Ser Gln Asn Gln Ile Leu Val Trp Lys Tyr Pro Ser
            420                 425                 430

Leu Thr Gln Val Ala Lys Leu Thr Gly His Ser Tyr Arg Val Leu Tyr
            435                 440                 445

Leu Ala Met Ser Pro Asp Gly Glu Ala Ile Val Thr Gly Ala Gly Asp
450                 455                 460

Glu Thr Leu Arg Phe Trp Asn Val Phe Ser Lys Thr Arg Ser Thr Lys
465                 470                 475                 480

Glu Ser Val Ser Val Leu Asn Leu Phe Thr Arg Ile Arg
            485                 490

<210> SEQ ID NO 11
<211> LENGTH: 5008
<212> TYPE: DNA
<213> ORGANISM: Homo sapiens

<400> SEQUENCE: 11
gctaaccttg ccgcgggccg agccctgcct cgccatggac caggactatg agcggcgcct      60
gcttcgccag atcgtcatcc agaatgagaa cacgatgcca cgcgtcacag agatgcggcg     120
gaccctgacg cctgccagct ccccagtgtc ctcgcccagc aagcacggag accgcttcat     180
cccctccaga gccggagcca actggagcgt gaacttccac aggattaacg agaatgagaa     240
gtctcccagt cagaaccgga aagccaagga cgccacctca gacaacgcca agacggcct     300
ggcctactct gccctgctca gaatgagct gctgggtgcc ggcatcgaga aggtgcagga     360
cccgcagact gaggaccgca ggctgcagcc tccacgcct gagaagaagg gtctgttcac     420
gtattccctt agcaccaagc gctccagccc cgatgacggc aacgatgtgt ctccctactc     480
cctgtctccc gtcagcaaca agagccagaa gctgctccgg tccccccgga aacccacccg     540
caagatctcc aagatcccct tcaaggtgct ggacgcgccc gagctgcagg acgacttcta     600
cctcaatctg gtggactggt cgtccctcaa tgtgctcagc gtggggctag gcacctgcgt     660
gtacctgtgg agtgcctgta ccagccaggt gacgcggctc tgtgacctct cagtggaagg     720
ggactcagtg acctccgtgg gctggtctga gcggggaac ctggtggcgg tgggcacaca     780
caagggcttc gtgcagatct gggacgcagc cgcaggaag aagctgtcca tgttggaggg     840
ccacacggca cgcgtcgggg cgctggcctg gaatgctgag cagctgtcgt ccggagccg     900
cgaccgcatg atcctgcaga gggacatccg caccccgcca ctgcagtcgg agcggcggct     960
gcagggccac cggcaggagg tgtgcgggct caagtggtcc acagaccacc agctcctcgc    1020
ctcggggggc aacgacaaca agctgctggt ctggaatcac tcgagcctga gccccgtgca    1080
```

```
gcagtacacg gagcacctgg cggccgtgaa ggccatcgcc tggtccccac atcagcacgg    1140
gctgctggcc tcgggggcg gcacagctga ccgctgtatc cgcttctgga acacgctgac     1200
aggacaacca ctgcagtgta tcgacacggg ctcccaagtg tgcaatctgg cctggtccaa    1260
gcacgccaac gagctggtga gcacgcacgg ctactcacag aaccagatcc ttgtctggaa    1320 gtaccctcc ctgacccagg tggccaagct gaccgggcac tcctaccgcg tgctgtacct    1380
ggcaatgtcc cctgatgggg aggccatcgt cactggtgct ggagacgaga ccctgaggtt    1440
ctggaacgtc tttagcaaaa cccgttcgac aaaggagtct gtgtctgtgc tcaacctctt    1500
caccaggatc cggtaaacct gccaggcagg accgtgccac accagctgtc cagagtcgga    1560
ggaccccagc tcctcagctt gcatggactc tgccttccca gcgcttgtcc cccgaggaag    1620
gcggctgggc gggcggggag ctgggcctgg aggatcctgg agtctcatta aatgcctgat    1680
tgtgaaccat gtccaccagt atctggggtg gcacgtggt cggggaccct cagcagcagg    1740
ggctctgtct cccttcccaa agggcgagaa ccacattgga cggtcccggc tcagaccgtc    1800
tgtactcaga gcgacggatg ccccctggga ccctcactgc ctccgtctgt tcatcacctg    1860
cccaccggag ccgcatgctc ttcctggaac tgcccacgtc tgcacagaac agaccaccag    1920
acgccagggc tgattggtgg gggcctgaga ccccggttg cccattcatg gctgcacccc    1980
accatgtcaa acccaagacc agccccaagg ccagaccaag gcatgtaggc ctgggcaggt    2040
ggctcggggc cactggcgga gccagtctgt ggatccaaga gacagtcccc acctgggctt    2100
cacggcatcc ttgcagccac ctctgctgtc actgctcgaa gcagcagtct ctctggaagc    2160
atctgtgtca tggccatcgc ccggcggtca gtgggcttca gatgggcctg tgcatcctgg    2220
ccaagcgtca ccctcacact ggaggaggat gtctgctctg gacttatcac cccaggagaa    2280
ctgaacccgg acctgctcac tgccctggct ggagaggagc acaacagatg ccacgtcttc    2340
gtgcattcgc caacacgtgc cctcacaggg ccagcgtcct ccttccctgc gcaagacttg    2400
cgtcccccat gcctgctggg tggctgggtc ctgtggaggc cagcagcggt gtggcccccg    2460 ccccaggct gcctgtgtct tcacctgtcc tgtccaccag cgccaacagc cgtggggaag    2520
ccaaggagac ccaaggggtc caggaggtgg gcgcccctcca tccttcgaga agcttcccag    2580
gctcctctgc ttctctgtct catgctccca ggctgcacag caggcaggga gggaggcaag    2640
gcaggggagt ggggcctgag ctgagcactg cccccctcacc ccccaccac cccttcccat    2700 ttcatcggtg gggacgtgga gagggtgggg cgggctgggg ttggagggtc ccacccacca    2760
ccctgctgtg cttgggaacc cccactcccc actcccaca tcccaacatc ctggtgtctg     2820
tccccagtgg ggttggcgtg catgtgtaca tatgtatttg tgacttttct ttggatttgt    2880
tttgtgtttt tgttgactag tcctggaaat gtttgaggct agacggggag gggccaggac    2940
ccacccactg ctcctggggg atgaggtcct ggttttaaag cccgtcatt tcaagcgggt     3000 cgatcttcca cattcactgg agagactctc cccaccctctg tctgggtggg gcgcggaccc    3060
ctcactgtgc gcctgtgcag ggggtgctgg tgcacgtggc agtgtggatt ccagtggtc     3120 acgtcttac tgtttcaagg tttttaaata agaaaaccaa ccctgccttc gcccatgccc     3180 gccctgccc gcagttgcca aagagccgcc ttgtcgctgt gggcgtcagg gcttggctgg    3240
ctcagtgcac aacccacagt ggccttcaga ggctcctcct gggactggga accgccgcag    3300
ggccaggcgg acggcgtgag gtttgtgttg gggctggttc tgcccatgct aggggtgggg    3360
ggagctccca ggacagacca gccttgtttc tcatgtaatg cagtgacgct gtcattaaac    3420
acgtggattc atgtgtggcc gggactggct ggctctaggt ccccggctcg ggtggggtca    3480
```

```
cacggtcctg ccctagagcc cccatctggc cctggagctg cagaagcagc ttctgagggg       3540
cttcccaggc ctgcatttca cagatgggga gctcagccct cgaaggccgc agagacgcct       3600
cccaggcccg tctgccaggg cgccggccac aatcctgcag ggccaaggac tggactccag       3660
gcaagtccct gcgctccagc tggacggccc tgttccaggg aggaggtgct cggttgacac       3720
catcagggag ggagggtggg cactgctggg ctgagttcac ccccagggct ggccagatgg       3780
ggccaggagg gacagagcaa gggggtgaa ggccgtggtg ggagggtccc atgatgatgg        3840
gccagggctc gtgtagaaat gggggaattg gttccccatg gcccaggaca gctgagagga       3900
ggtggagggg ccccagggga gtgtacgtca ggctttgcgg ggcacggggg ccactcagca       3960
gcgctgggc aggtgcctct gctgtcagct ccacccgaca ggcagacgaa ggccagtggg       4020
gccatcgctt cctggggcga ccctggcagt ggttgggaga cgcccagatg gaggggaggg      4080
ctgaccaagg gccccgcagg gcgggctgca acttttctgt tgatcctgga atgtagctgg       4140
tgcagtgaga gggaaagaga attgaaaaac tcaggctgcc ataggttctg cgatgagagg       4200
tgcaggaggc aggagcctgg cccaggggt gctggtgcct ccccgggtgc tgggcggaga        4260
gaacaggagg aatggctggg aagtggctga gggagccagg aggccggggg ccgggggct        4320
gcagggagg ctgtgggggt cctggcagcc aggaggcccc aggtggtttt gaggctcgct        4380
cttgcgcggt gcctgagaag agggtgaagg agctggggca ggcccatcc tgggcattgg        4440
agatgatgaa accgagcaga cctggcccat gtggagctgg catgggggac acagcccaga       4500
gacagagaag cttatgagga agtgaggagg tggcgtcaca agggtgggga gggggccttg       4560
gggaagggcg gccttggatc agaggctcac cacaagcctg gcatttcagc cagggctgga       4620
gaaggcaggg acgcctgggt gagaggcaaa gggcacagcc atgcaaaggc cctggggcag       4680
gacggcacct ggtatgcggg aggaacagag tgaggagagg agggcagggc gtgcagggcc       4740
ttgtgggcct cagggaggac ttgggcacct accccgaggg agtggagctc ctgggtgcgt       4800
gtccagatgg gaaaggcagg gtcgtatctg tggggacctg acaagggcag gggaagcgga       4860
gaccagggtg caggctccgc ccccacccaa ggccgggccc agccagagga ggggcagggc       4920
agggcaggag gtttctggat gtttgttggg tttggtttgg ttttgtttg ttttgtttat        4980
tgtggtaaaa tacaaaatct accgtctt                                          5008
```

<210> SEQ ID NO 12
<211> LENGTH: 499
<212> TYPE: PRT
<213> ORGANISM: Homo sapiens

<400> SEQUENCE: 12

```
Met Ala Gln Phe Ala Phe Glu Ser Asp Leu His Ser Leu Leu Gln Leu
1               5                   10                  15

Asp Ala Pro Ile Pro Asn Ala Pro Pro Ala Arg Trp Gln Arg Lys Ala
            20                  25                  30

Lys Glu Ala Ala Gly Pro Ala Pro Ser Pro Met Arg Ala Ala Asn Arg
        35                  40                  45

Ser His Ser Ala Gly Arg Thr Pro Gly Arg Thr Pro Gly Lys Ser Ser
    50                  55                  60

Ser Lys Val Gln Thr Thr Pro Ser Lys Pro Gly Gly Asp Arg Tyr Ile
65                  70                  75                  80

Pro His Arg Ser Ala Ala Gln Met Glu Val Ala Ser Phe Leu Leu Ser
                85                  90                  95

Lys Glu Asn Gln Pro Glu Asn Ser Gln Thr Pro Thr Lys Lys Glu His
            100                 105                 110
```

```
Gln Lys Ala Trp Ala Leu Asn Leu Asn Gly Phe Asp Val Glu Glu Ala
            115                 120                 125

Lys Ile Leu Arg Leu Ser Gly Lys Pro Gln Asn Ala Pro Glu Gly Tyr
        130                 135                 140

Gln Asn Arg Leu Lys Val Leu Tyr Ser Gln Lys Ala Thr Pro Gly Ser
145                 150                 155                 160

Ser Arg Lys Thr Cys Arg Tyr Ile Pro Ser Leu Pro Asp Arg Ile Leu
                165                 170                 175

Asp Ala Pro Glu Ile Arg Asn Asp Tyr Tyr Leu Asn Leu Val Asp Trp
            180                 185                 190

Ser Ser Gly Asn Val Leu Ala Val Ala Leu Asp Asn Ser Val Tyr Leu
        195                 200                 205

Trp Ser Ala Ser Ser Gly Asp Ile Leu Gln Leu Gln Met Glu Gln
    210                 215                 220

Pro Gly Glu Tyr Ile Ser Ser Val Ala Trp Ile Lys Glu Gly Asn Tyr
225                 230                 235                 240

Leu Ala Val Gly Thr Ser Ser Ala Glu Val Gln Leu Trp Asp Val Gln
                245                 250                 255

Gln Gln Lys Arg Leu Arg Asn Met Thr Ser His Ser Ala Arg Val Gly
            260                 265                 270

Ser Leu Ser Trp Asn Ser Tyr Ile Leu Ser Ser Gly Ser Arg Ser Gly
        275                 280                 285

His Ile His His His Asp Val Arg Val Ala Glu His His Val Ala Thr
    290                 295                 300

Leu Ser Gly His Ser Gln Glu Val Cys Gly Leu Arg Trp Ala Pro Asp
305                 310                 315                 320

Gly Arg His Leu Ala Ser Gly Gly Asn Asp Asn Leu Val Asn Val Trp
                325                 330                 335

Pro Ser Ala Pro Gly Glu Gly Gly Trp Val Pro Leu Gln Thr Phe Thr
            340                 345                 350

Gln His Gln Gly Ala Val Lys Ala Val Ala Trp Cys Pro Trp Gln Ser
        355                 360                 365

Asn Val Leu Ala Thr Gly Gly Gly Thr Ser Asp Arg His Ile Arg Ile
    370                 375                 380

Trp Asn Val Cys Ser Gly Ala Cys Leu Ser Ala Val Asp Ala His Ser
385                 390                 395                 400

Gln Val Cys Ser Ile Leu Trp Ser Pro His Tyr Lys Glu Leu Ile Ser
                405                 410                 415

Gly His Gly Phe Ala Gln Asn Gln Leu Val Ile Trp Lys Tyr Pro Thr
            420                 425                 430

Met Ala Lys Val Ala Glu Leu Lys Gly His Thr Ser Arg Val Leu Ser
        435                 440                 445

Leu Thr Met Ser Pro Asp Gly Ala Thr Val Ala Ser Ala Ala Ala Asp
450                 455                 460

Glu Thr Leu Arg Leu Trp Arg Cys Phe Glu Leu Asp Pro Ala Arg Arg
465                 470                 475                 480

Arg Glu Arg Glu Lys Ala Ser Ala Ala Lys Ser Ser Leu Ile His Gln
                485                 490                 495

Gly Ile Arg

<210> SEQ ID NO 13
<211> LENGTH: 191
<212> TYPE: PRT
<213> ORGANISM: Homo sapiens
```

<400> SEQUENCE: 13

| | | | | | | | | | | | | | | |
|---|---|---|---|---|---|---|---|---|---|---|---|---|---|---|
|Met|Ala|Ala|Glu|Ser|Gly|Glu|Leu|Ile|Gly|Ala|Cys|Glu|Phe|Met|Lys
1| | | |5| | | | |10| | | | |15|

Asp Arg Leu Tyr Phe Ala Thr Leu Arg Asn Arg Pro Lys Ser Thr Val
    20       25       30

Asn Thr His Tyr Phe Ser Ile Asp Glu Glu Leu Val Tyr Glu Asn Phe
      35      40      45

Tyr Ala Asp Phe Gly Pro Leu Asn Leu Ala Met Val Tyr Arg Tyr Cys
 50      55      60

Cys Lys Leu Asn Lys Lys Leu Lys Ser Tyr Ser Leu Ser Arg Lys Lys
65      70      75      80

Ile Val His Tyr Thr Cys Phe Asp Gln Arg Lys Arg Ala Asn Ala Ala
      85      90      95

Phe Leu Ile Gly Ala Tyr Ala Val Ile Tyr Leu Lys Lys Thr Pro Glu
    100      105      110

Glu Ala Tyr Arg Ala Leu Leu Ser Gly Ser Asn Pro Pro Tyr Leu Pro
    115      120      125

Phe Arg Asp Ala Ser Phe Gly Asn Cys Thr Tyr Asn Leu Thr Ile Leu
130      135      140

Asp Cys Leu Gln Gly Ile Arg Lys Gly Leu Gln His Gly Phe Phe Asp
145      150      155      160

Phe Glu Thr Phe Asp Val Asp Glu Tyr Glu His Tyr Glu Val Ile Leu
      165      170      175

Phe Thr Pro Leu Lys Pro Thr Phe Leu Ile Ser Lys Ser Ile Met
    180      185      190

<210> SEQ ID NO 14
<211> LENGTH: 1965
<212> TYPE: DNA
<213> ORGANISM: Homo sapiens

<400> SEQUENCE: 14

```
ccgggggcga gtgacctcag ctggccacga cccagccctc ccccgtgcgt atctcgctta      60
agatggcagc ggagtcaggg gaactaatcg gggcttgtga gttcatgaaa gatcggttat     120
attttgctac tttaaggaat agaccaaaaa gcacagtaaa tacccactat ttctccatcg     180
atgaggagct ggtctatgaa aatttctatg cagattttgg accgctgaac ttggcaatgg     240
tgtacagata ttgctgcaaa ctaaacaaga actaaaatc atacagtttg tcaagaaaga     300
aaatagtgca ctacacctgt tttgaccaac ggaaaagagc aaatgcagca ttttttgatag     360
gtgcctatgc agtaatctat ttaaagaaga caccagaaga agcctacaga gcactcctgt     420
ctggctcaaa ccccccctat cttccattca gggatgcttc ctttggaaat tgcacttaca     480
atctcaccat tctcgactgt ttgcagggaa tcagaaaggg attacaacat ggatttttg     540
actttgagac atttgatgtg gatgaatatg aacattatga ggttatcctc ttcacgcccc     600
tgaagcctac tttccttatt tcaaaaagca taatgtgact gcagttgtga ggctaaacaa     660
aaagatttat gaggcaaagc gcttcacaga cgctggcttc gagcactatg acctcttctt     720
catagatggc agcacaccca gtgacaacat cgtgcgaagg ttcctgaaca tctgtgagaa     780
caccgaaggg gccatcgccg ttcactgcaa agctggtctt ggaagaacag ggacattgat     840
agcctgttat gtaatgaaac actacaggtt tacacatgct gaaataattg cttggattag     900
aatatgccgg ccaggctcta ttataggacc ccagcagcac ttcctggaag aaaaacaagc     960
atcattgtgg gtccaaggag acatttttccg atccaaactg aaaaatcgac catccagtga    1020
```

```
aggaagtatt aataaaattc tttctggcct agatgatatg tctattggtg gaaatctttc    1080
aaaaacacaa acatggaac gatttggaga ggataactta aagatgatg atgtggaaat    1140 gaaaaatggt ataacccagg gagacaaact acgtgcctta aaaagtcaga cagccacg    1200 tacctcacca tcctgtgcat ttaggtcaga tgatacaaaa ggacatccaa gagcagtgtc    1260
ccagcctttc agattaagtt catccctgca aggatctgca gttactttga agacatcaaa    1320
aatggcactg tccccttcag caacggccaa gaggatcaac agaacttctt tgtcttcggg    1380
tgccactgta agaagctttt ccataaactc ccggctagcc agttctctag ggaacttgaa    1440
tgctgcaaca gatgatccag agaacaaaaa gacctcctca tcctctaagg caggcttcac    1500
agccagcccg tttaccaacc tcttgaatgg cagctcccag ccaactacca gaaattaccc    1560
tgagctcaac aataatcagt acaacagaag cagcaacaga acgggggca acctgaacag    1620 ccccccaggc ccccacagcg ccaagacaga ggagcacacc accatcctcc gaccctccta    1680
caccgggctt tcttcttctt cagcgagatt cctgagccgt tctatccctg taagtgcgca    1740
gacaccacct cctggtcctc agaaccctga atgcaacttc tgtgccttgc cttcccagcc    1800
gaggctgcca ccaaagaaat ttaatagtgc caaggaagcc ttctgagcga tgccttccct    1860
ctgtgctgtg aaactgtcta tgcactacat tctgctagct cctcttcaag taaacgccaa    1920
gtcacaactg gaaaaaaaaa aaaaaaaaa aaaaaaaaa aaaaa              1965
```

<210> SEQ ID NO 15
<211> LENGTH: 459
<212> TYPE: PRT
<213> ORGANISM: Homo sapiens

<400> SEQUENCE: 15

```
Met Lys Arg Lys Ser Glu Arg Arg Ser Ser Trp Ala Ala Ala Pro Pro
1               5                   10                  15

Cys Ser Arg Arg Cys Ser Ser Thr Ser Pro Gly Val Lys Lys Ile Arg
            20                  25                  30

Ser Ser Thr Gln Gln Asp Pro Arg Arg Arg Asp Pro Gln Asp Asp Val
        35                  40                  45

Tyr Leu Asp Ile Thr Asp Arg Leu Cys Phe Ala Ile Leu Tyr Ser Arg
    50                  55                  60

Pro Lys Ser Ala Ser Asn Val His Tyr Phe Ser Ile Asp Asn Glu Leu
65                  70                  75                  80

Glu Tyr Glu Asn Phe Tyr Ala Asp Phe Gly Pro Leu Asn Leu Ala Met
                85                  90                  95

Val Tyr Arg Tyr Cys Cys Lys Ile Asn Lys Lys Leu Lys Ser Ile Thr
            100                 105                 110

Met Leu Arg Lys Lys Ile Val His Phe Thr Gly Ser Asp Gln Arg Lys
        115                 120                 125

Gln Ala Asn Ala Ala Phe Leu Val Gly Cys Tyr Met Val Ile Tyr Leu
    130                 135                 140

Gly Arg Thr Pro Glu Glu Ala Tyr Arg Ile Leu Ile Phe Gly Glu Thr
145                 150                 155                 160

Ser Tyr Ile Pro Phe Arg Asp Ala Ala Tyr Gly Ser Cys Asn Phe Tyr
                165                 170                 175

Ile Thr Leu Leu Asp Cys Phe His Ala Val Lys Lys Ala Met Gln Tyr
            180                 185                 190

Gly Phe Leu Asn Phe Asn Ser Phe Asn Leu Asp Glu Tyr Glu His Tyr
        195                 200                 205
```

```
Glu Lys Ala Glu Asn Gly Asp Leu Asn Trp Ile Ile Pro Asp Arg Phe
    210                 215                 220

Ile Ala Phe Cys Gly Pro His Ser Arg Ala Arg Leu Glu Ser Gly Tyr
225                 230                 235                 240

His Gln His Ser Pro Glu Thr Tyr Ile Gln Tyr Phe Lys Asn His Asn
                245                 250                 255

Val Thr Thr Ile Ile Arg Leu Asn Lys Arg Met Tyr Asp Ala Lys Arg
            260                 265                 270

Phe Thr Asp Ala Gly Phe Asp His His Asp Leu Phe Phe Ala Asp Gly
        275                 280                 285

Ser Thr Pro Thr Asp Ala Ile Val Lys Glu Phe Leu Asp Ile Cys Glu
    290                 295                 300

Asn Ala Glu Gly Ala Ile Ala Val His Cys Lys Ala Gly Leu Gly Arg
305                 310                 315                 320

Thr Gly Thr Leu Ile Ala Cys Tyr Ile Met Lys His Tyr Arg Met Thr
                325                 330                 335

Ala Ala Glu Thr Ile Ala Trp Val Arg Ile Cys Arg Pro Gly Ser Val
            340                 345                 350

Ile Gly Pro Gln Gln Gln Phe Leu Val Met Lys Gln Thr Asn Leu Trp
        355                 360                 365

Leu Glu Gly Asp Tyr Phe Arg Gln Lys Leu Lys Gly Gln Glu Asn Gly
    370                 375                 380

Gln His Arg Ala Ala Phe Ser Lys Leu Leu Ser Gly Val Asp Asp Ile
385                 390                 395                 400

Ser Ile Asn Gly Val Glu Asn Gln Asp Gln Glu Pro Glu Pro Tyr
                405                 410                 415

Ser Asp Asp Glu Ile Asn Gly Val Thr Gln Gly Asp Arg Leu Arg
            420                 425                 430

Ala Leu Lys Ser Arg Arg Gln Ser Lys Thr Asn Ala Ile Pro Leu Thr
            435                 440                 445

Leu Ser Ile Ser Arg Thr Lys Thr Val Leu Arg
    450                 455

<210> SEQ ID NO 16
<211> LENGTH: 5472
<212> TYPE: DNA
<213> ORGANISM: Homo sapiens

<400> SEQUENCE: 16
cacggaacag ccctcctggg gtccccacga gccgcgtcct gctgtgcccc ggcgcctacg      60
cagcagcggc cgcggccgcg gtgggcacgc acggttaccc cgggcagctc cggccgccag     120
ctgcagcccc gtcgcctcgg ccgcgccagc cggctgcggg cacctggggg cgggctgggg     180
gcgccggccg cggcaggagg cgctgtagcg agggctgcgg cgccggtcct gcggcggccg     240
cgggaggcag cggggcaggc gctgtgggcc gggctcctcc tccggctcct gcgcgaccgc     300
ctcccgccgg gctctgccgg cgcccgccgt ccccgcagcg ccgctctgcg cccgccgccc     360
cgagcgcccg cgcggggctg gcgggagcct cggcgggcgc gcgggcgcgc ggggccatgg     420
tcgtggcccc ctgacgggcc gcggccgcct ccatgaagcg gaaaagcgag cggcggtcga     480
gctgggccgc cgcgcccccc tgctcgcggc gctgctcgtc gacctcgccg ggtgtgaaga     540
agatccgcag ctccacgcag caagacccgc gccgccggga cccccaggac gacgtgtacc     600
tggacatcac cgatcgcctt tgttttgcca ttctctacag cagaccaaag agtgcatcaa     660
atgtacatta tttcagcata gataatgaac ttgaatatga gaacttctac gcagattttg     720
```

```
gaccactcaa tctggcaatg gtttacagat attgttgcaa gatcaataag aaattaaagt      780
ccattacaat gttaaggaag aaaattgttc attttactgg ctctgatcag agaaaacaag      840
caaatgctgc cttccttgtt ggatgctaca tggttatata tttggggaga accccagaag      900
aagcatatag aatattaatc tttggagaga catcctatat tcctttcaga gatgctgcct      960
atggaagttg caatttctac attcacttc ttgactgttt tcatgcagta aagaaggcaa     1020
tgcagtatgg cttccttaat ttcaactcat ttaaccttga tgaatatgaa cactatgaaa     1080
aagcagaaaa tggagattta aattggataa taccagaccg atttattgcc ttctgtggac     1140
ctcattcaag agccagactt gaaagtggtt accaccaaca ttctcctgag acttatattc     1200 aatatttaa gaatcacaat gttactacca ttattcgtct gaataaaagg atgtatgatg      1260
ccaaacgctt tacggatgct ggcttcgatc accatgatct tttctttgcg gatggcagca     1320
cccctactga tgccattgtc aaagaattcc tagatatctg tgaaaatgct gagggtgcca     1380
ttgcagtaca ttgcaaagct ggccttggtc gcacgggcac tctgatagcc tgctacatca     1440
tgaagcatta caggatgaca gcagccgaga ccattgcgtg ggtcaggatc tgcagacctg     1500
gctcggtgat tgggcctcag cagcagtttt tggtgatgaa gcaaaccaac ctctggctgg     1560
aaggggacta ttttcgtcag aagttaaagg ggcaggagaa tggacaacac agagcagcct     1620
tctccaaact tctctctggc gttgatgaca tttccataaa tggggtcgag aatcaagatc     1680
agcaagaacc cgaaccgtac agtgatgatg acgaaatcaa tggagtgaca caaggtgata     1740
gacttcgggc cttgaaaagc agaagacaat ccaaaacaaa cgctattcct ctcactctct     1800
ccatttcaag gactaaaaca gtcttgcgtt aagtaaaaac ctgtgaccag agctgaagga     1860
agactctagg actgaaaact gcaacagaaa ttagcacaat ttgaaaacaa aacaaaattg     1920
caaaagcctt agttgctttt tccacctaag aagttgatca atggagaaaa tgtccactgg     1980
agtttgaata tgaactttg agtttgggtg caagcaaatg actcagagaa gggtccagct     2040
ctcaagctga atgacaaaca tgctgttgta aatttagtct caggtgtaaa tacccaagcc     2100
ctctggtacc cagggagctg gctggtctgt ggtgcatgtg tgtccctgtg atggcaatca     2160
ttgtagttgc tggccttcag aagaattgag gatctgatgg aggttttta tgtatttatt       2220 ttctgttcac cttgtgaccc tgtgtcaaaa tttataaga tacaaaaggc attactgaaa       2280
tggtactttc tgtaatttga tactatttgg cttaatcatc ttcacttgac tatttgtaat     2340
actgttgtaa tgttaactct gttaagtacc caagctgctt gtcttccacc aaagagtgct     2400
ttattaacaa gaatctgtga aaatcacatt taaacactgt tgcatgttgt aagaccaggt     2460
ggtaccttag taacctaaaa cttgcaagag aatattaatg gtagctttag aagactcagg     2520
aggagaaact gacttcagag ttggaagatg ttgcaagtcg ttccttttc tgtccttcag      2580 ggactgaaga actgggaggc tgcccattgt ttggttgcca gtcatacaaa ttaaaatcat     2640
atttccttcc atgaatggaa gaaacacact attggttttt ccccttggaa acagcaatcc     2700
caaataatgt cggcttacaa aaaaaaaaag ttaccacttt tttagagtcc ttccctgtaa     2760
cattggattt tttttttccc ttatgagatc cacctaaggc cattgacgtg gcctgcgatc     2820
tcagtgacaa tgatctgctt ctggatctca ctgttgcctt tggttaggga acacaactag     2880
taactctgca gagtgcctt ccccgcagcc ctactggaac acagcagagt ctgtgccatg      2940
aagcagttac agaaacagaa ttgatgtgct gctaaaaaaa aaaaaaaaa tggggcccga     3000 aataaaagaa tatatagtac tcacctcagt tccttccata agaagtgggt ggtttaatga     3060
ttgttaagcc attttttgcct gtgccgggag catggagggc tgagatgtcg acaggcagtg   3120
```

-continued

```
ggaaacaaat gccctcctaa gccacaaggc gtgcgccaga ttagtaggca actccatttt    3180
aagaagctgc cttttttcaca aaactggaag aaataaaagc ggttggaata aacaagttaa    3240
aagtctttaa tgcaaaaagt aattgaaagg cagtgcctcc attttggtgt actttcttgg    3300
aagaaagtat aaaattgacc ggcatcatga gagacggaag atgccgtgtt ctcagccaaa    3360
caagcaactc tttccccgcc aggcactgtc gggtggggtc aggccagctt ttaaacactg    3420
gggactggat cacagaaaaa cagtggtttt ctgtccctgg aaatgaatag cacaaagac     3480 ccacttggct gtgggcagac tactcttcaa taagatttgg gtgggaggag gaacattcct    3540
tttgctattt tgagctgaga caatataaat attcaaactg tgccatgcat aaagcattga    3600
attctcaggg cacctcttct tccccttacc ccttttaagg ccatcccctc cattaataat    3660
aatccaggta gttgtgaaaa tcgtgcttct atctgatccc ttcttagttt ggcttttcat    3720
cccatcagaa caagtaaacg taggcgccac agctcttgtg agtactgtct ccctcacggt    3780
gaatgagcct cctggtgttt cgtccaagaa aagaaagggt gtcactggaa ccacagccct    3840
ttttcatttt ataaactgcc tcttcatgtt gcctgctcaa gtttccacct agaattgcta    3900
tcactgtggc tctttctaaa aatctttcta tttaactggt tcactgaaat tagtcataga    3960
aaacttgtga tttggtgaag aggcattcct tgtaataacc aaatgacttg ggatggtgtg    4020
catagcaagg gcagtgttac acttatgagg actgtctcta gcatccagga agtctctggg    4080
tctgagggat ggaaagttct tcctgctatg aatgagagtg gactcttccc ctcaccccca    4140
actgaaacca caaacaacca gaatcttctg gaattctgac ttagagtcgt tgttatagaa    4200
gaccttgttg ctatggaaca tgaaactgtg tgtcagatgg agagatcccc ttaacctaag    4260
agccttaaat agccctgaaa gtacactggg acggtttgcg atggaattaa aattggaagt    4320 gaatatttt aggtgctctt gaagcttttct ggggactcaa aattatcaaa agtcagggac    4380
agtccggagg aagagcgtct gcaaaactgg gttcctagaa gtatagacgg acttagcttt    4440
ttgtagaatt tggtgaggag cagcgcctcg tgagagcaga atggcctggc gtggccagtg    4500
cttcccggca gcacgcagct ctgcggcctc cagaattccc ctgttctgag cttgatgccc    4560
ctagcctgtc ccctacctac ttcctcccct cctctctagc cctctcacag gggtgattgc    4620
tacctctctg ttttcttggg cctaggcaag ttttagagga gttcccaagc attgttatga    4680
ggccagtgtg ctcgctgggc tgggcgggat ggcctgggct tgtgtgtggc ctgagggctc    4740
tcctggggcc ttctcttttc ccagtcacct ttggagccac agaagcagtg cactccattgg   4800 atgtctgttc ttaacacagc ttctctttct acattaaaaa aaatcattat tgcatttgg    4860 aaagcagtgc tcatcaaaag caacttttaa aacctatttt attgttcctt taaatgttct    4920
ctcccgctga aactgccctg gagaggctat ctgctgctct tccatttacc cacatcaggt    4980
tattctccat gtcactcagt ggagatgact ccagatgtgt ttaaagactg gacaattcac    5040
ctatactgtg taggaaatta cctccttaat tacctggtag aattgtcagc agacatgttc    5100
atccgatgat agtactgcag ttttctatta ataatttgca gactttttatc taacctgcac    5160 tcatgtacag attattaaaa gttttaaaat gtaactgatc agtattgatc aatcattgtc    5220 ttgattttt tttacagcgt atatttctaa tcatattttt taaagccaag agaactggtt    5280
gaatgaatgt ttatttttcct gaaggtattt ttaagataaa gcttcctaat ggcgtgtaaa    5340
ctttgcatat gtatgtagtt tgatacatat tgtcacattt gaaaatcttg tgggttgtaa    5400
ctggttttat acaaaatatc gaatagtgga aattgtataa ttacaatcat gtaattaaaa    5460
gtattaaccc aa                                                        5472
```

<210> SEQ ID NO 17
<211> LENGTH: 603
<212> TYPE: PRT
<213> ORGANISM: Homo sapiens

<400> SEQUENCE: 17

```
Met Ser Ala Ala Val Thr Ala Gly Lys Leu Ala Arg Ala Pro Ala Asp
1               5                   10                  15

Pro Gly Lys Ala Gly Val Pro Gly Val Ala Ala Pro Gly Ala Pro Ala
                20                  25                  30

Ala Ala Pro Pro Ala Lys Glu Ile Pro Glu Val Leu Val Asp Pro Arg
            35                  40                  45

Ser Arg Arg Arg Tyr Val Arg Gly Arg Phe Leu Gly Lys Gly Gly Phe
        50                  55                  60

Ala Lys Cys Phe Glu Ile Ser Asp Ala Asp Thr Lys Glu Val Phe Ala
65                  70                  75                  80

Gly Lys Ile Val Pro Lys Ser Leu Leu Leu Lys Pro His Gln Arg Glu
                85                  90                  95

Lys Met Ser Met Glu Ile Ser Ile His Arg Ser Leu Ala His Gln His
                100                 105                 110

Val Val Gly Phe His Gly Phe Phe Glu Asp Asn Asp Phe Val Phe Val
            115                 120                 125

Val Leu Glu Leu Cys Arg Arg Arg Ser Leu Leu Glu Leu His Lys Arg
        130                 135                 140

Arg Lys Ala Leu Thr Glu Pro Glu Ala Arg Tyr Tyr Leu Arg Gln Ile
145                 150                 155                 160

Val Leu Gly Cys Gln Tyr Leu His Arg Asn Arg Val Ile His Arg Asp
                165                 170                 175

Leu Lys Leu Gly Asn Leu Phe Leu Asn Glu Asp Leu Glu Val Lys Ile
            180                 185                 190

Gly Asp Phe Gly Leu Ala Thr Lys Val Glu Tyr Asp Gly Glu Arg Lys
        195                 200                 205

Lys Thr Leu Cys Gly Thr Pro Asn Tyr Ile Ala Pro Glu Val Leu Ser
210                 215                 220

Lys Lys Gly His Ser Phe Glu Val Asp Val Trp Ser Ile Gly Cys Ile
225                 230                 235                 240

Met Tyr Thr Leu Leu Val Gly Lys Pro Pro Phe Glu Thr Ser Cys Leu
                245                 250                 255

Lys Glu Thr Tyr Leu Arg Ile Lys Lys Asn Glu Tyr Ser Ile Pro Lys
            260                 265                 270

His Ile Asn Pro Val Ala Ala Ser Leu Ile Gln Lys Met Leu Gln Thr
        275                 280                 285

Asp Pro Thr Ala Arg Pro Thr Ile Asn Glu Leu Leu Asn Asp Glu Phe
290                 295                 300

Phe Thr Ser Gly Tyr Ile Pro Ala Arg Leu Pro Ile Thr Cys Leu Thr
305                 310                 315                 320

Ile Pro Pro Arg Phe Ser Ile Ala Pro Ser Ser Leu Asp Pro Ser Asn
                325                 330                 335

Arg Lys Pro Leu Thr Val Leu Asn Lys Gly Leu Glu Asn Pro Leu Pro
            340                 345                 350

Glu Arg Pro Arg Glu Lys Glu Glu Pro Val Val Arg Glu Thr Gly Glu
        355                 360                 365

Val Val Asp Cys His Leu Ser Asp Met Leu Gln Gln Leu His Ser Val
370                 375                 380
```

```
Asn Ala Ser Lys Pro Ser Glu Arg Gly Leu Val Arg Gln Glu Glu Ala
385                 390                 395                 400

Glu Asp Pro Ala Cys Ile Pro Ile Phe Trp Val Ser Lys Trp Val Asp
                405                 410                 415

Tyr Ser Asp Lys Tyr Gly Leu Gly Tyr Gln Leu Cys Asp Asn Ser Val
            420                 425                 430

Gly Val Leu Phe Asn Asp Ser Thr Arg Leu Ile Leu Tyr Asn Asp Gly
        435                 440                 445

Asp Ser Leu Gln Tyr Ile Glu Arg Asp Gly Thr Glu Ser Tyr Leu Thr
    450                 455                 460

Val Ser Ser His Pro Asn Ser Leu Met Lys Lys Ile Thr Leu Leu Lys
465                 470                 475                 480

Tyr Phe Arg Asn Tyr Met Ser Glu His Leu Leu Lys Ala Gly Ala Asn
                485                 490                 495

Ile Thr Pro Arg Glu Gly Asp Glu Leu Ala Arg Leu Pro Tyr Leu Arg
            500                 505                 510

Thr Trp Phe Arg Thr Arg Ser Ala Ile Ile Leu His Leu Ser Asn Gly
        515                 520                 525

Ser Val Gln Ile Asn Phe Phe Gln Asp His Thr Lys Leu Ile Leu Cys
    530                 535                 540

Pro Leu Met Ala Ala Val Thr Tyr Ile Asp Glu Lys Arg Asp Phe Arg
545                 550                 555                 560

Thr Tyr Arg Leu Ser Leu Leu Glu Glu Tyr Gly Cys Cys Lys Glu Leu
                565                 570                 575

Ala Ser Arg Leu Arg Tyr Ala Arg Thr Met Val Asp Lys Leu Leu Ser
            580                 585                 590

Ser Arg Ser Ala Ser Asn Arg Leu Lys Ala Ser
        595                 600

<210> SEQ ID NO 18
<211> LENGTH: 2204
<212> TYPE: DNA
<213> ORGANISM: Homo sapiens

<400> SEQUENCE: 18
gagcggtgcg gaggctctgc tcggatcgag gtctgcagcg cagcttcggg agcatgagtg      60
ctgcagtgac tgcagggaag ctggcacggg caccggccga ccctgggaaa gccggggtcc     120
ccggagttgc agctcccgga gctccggcgg cggctccacc ggcgaaagag atcccggagg     180
tcctagtgga cccacgcagc cggcggcgct atgtgcgggg ccgcttttg ggcaagggcg      240 gcttttgccaa gtgcttcgag atctcggacg cggacaccaa ggaggtgttc gcgggcaaga     300
ttgtgcctaa gtctctgctg ctcaagccgc accagaggga gaagatgtcc atggaaatat     360
ccattcaccg cagcctcgcc caccagcacg tcgtaggatt ccacggcttt ttcgaggaca     420
acgacttcgt gttcgtggtg ttggagctct gccgccggag gtctctcctg agctgcaca      480 agaggaggaa agccctgact gagcctgagg cccgatacta cctacggcaa attgtgcttg     540
gctgccagta cctgcaccga aaccgagtta ttcatcgaga cctcaagctg gcaacccttt     600
tcctgaatga agatctggag gtgaaaatag ggattttggg actggcaacc aaagtcgaat     660
atgacgggga gaggaagaag accctgtgtg ggactcctaa ttacatagct cccgaggtgc     720
tgagcaagaa agggcacagt ttcgaggtgg atgtgtggtc cattgggtgt atcatgtata     780
ccttgttagt gggcaaacca cctttgaga cttcttgcct aaaagagacc tacctccgga     840
tcaagaagaa tgaatacagt attcccaagc acatcaaccc cgtggccgcc tccctcatcc     900
```

-continued

```
agaagatgct tcagacagat cccactgccc gcccaaccat taacgagctg cttaatgacg    960
agttctttac ttctggctat atccctgccc gtctccccat cacctgcctg accattccac   1020
caaggttttc gattgctccc agcagcctgg accccagcaa ccggaagccc ctcacagtcc   1080
tcaataaagg cttggagaac cccctgcctg agcgtcccccg ggaaaaagaa gaaccagtgg   1140
ttcgagagac aggtgaggtg gtcgactgcc acctcagtga catgctgcag cagctgcaca   1200
gtgtcaatgc ctccaagccc tcggagcgtg gctggtcag gcaagaggag gctgaggatc   1260
ctgcctgcat ccccatcttc tgggtcagca agtgggtgga ctattcggac aagtacggcc   1320
ttgggtatca gctctgtgat aacagcgtgg gggtgctctt caatgactca acacgcctca   1380
tcctctacaa tgatggtgac agcctgcagt acatagagcg tgacggcact gagtcctacc   1440
tcaccgtgag ttcccatccc aactccttga tgaagaagat caccctcctt aaatatttcc   1500
gcaattacat gagcgagcac ttgctgaagg caggtgccaa catcacgccg cgcgaaggtg   1560
atgagctcgc ccggctgccc tacctacgga cctggttccg cacccgcagc gccatcatcc   1620
tgcacctcag caacggcagc gtgcagatca acttcttcca ggatcacacc aagctcatct   1680
tgtgcccact gatggcagcc gtgacctaca tcgacgagaa gcgggacttc cgcacatacc   1740
gcctgagtct cctggaggag tacggctgct gcaaggagct ggccagccgg ctccgctacg   1800
cccgcactat ggtggacaag ctgctgagct cacgctcggc cagcaaccgt ctcaaggcct   1860
cctaatagct gccctcccct ccggactggt gccctcctca ctcccacctg catctggggc   1920
ccatactggt tggctcccgc ggtgccatgt ctgcagtgtg cccccagcc ccggtggctg   1980 ggcagagctg catcatcctt gcaggtgggg gttgctgtgt aagttatttt tgtacatgtt   2040
cgggtgtggg ttctacagcc ttgtccccct cccctcaac cccaccatat gaattgtaca   2100
gaatatttct attgaattcg gaactgtcct ttccttggct ttatgcacat taaacagatg   2160
tgaatattca aaaaaaaaaa aaaaaaaaaa aaaaaaaaaa aaaa                    2204

<210> SEQ ID NO 19
<211> LENGTH: 38
<212> TYPE: PRT
<213> ORGANISM: Homo sapiens

<400> SEQUENCE: 19

Asp His Ile Ala Glu Asn Ile Leu Ser Tyr Leu Asp Ala Lys Ser Leu
1               5                   10                  15

Cys Ala Ala Glu Leu Val Cys Lys Glu Trp Tyr Arg Val Thr Ser Asp
            20                  25                  30

Gly Met Leu Trp Lys Lys
        35

<210> SEQ ID NO 20
<211> LENGTH: 19
<212> TYPE: RNA
<213> ORGANISM: Homo sapiens

<400> SEQUENCE: 20
guggaauuug uggaacauc                                                    19

<210> SEQ ID NO 21
<211> LENGTH: 19
<212> TYPE: RNA
<213> ORGANISM: Homo sapiens

<400> SEQUENCE: 21
ugagaagucu cccagucag                                                    19
```

```
<210> SEQ ID NO 22
<211> LENGTH: 19
<212> TYPE: RNA
<213> ORGANISM: Homo sapiens

<400> SEQUENCE: 22
gaugcuacau gguuauaua                                                  19

<210> SEQ ID NO 23
<211> LENGTH: 19
<212> TYPE: RNA
<213> ORGANISM: Homo sapiens

<400> SEQUENCE: 23
cugcauucac cuuaucauu                                                  19

<210> SEQ ID NO 24
<211> LENGTH: 19
<212> TYPE: RNA
<213> ORGANISM: Homo sapiens

<400> SEQUENCE: 24
cguacgcgga auacuucga                                                  19

<210> SEQ ID NO 25
<211> LENGTH: 18
<212> TYPE: DNA
<213> ORGANISM: Artificial
<220> FEATURE:
<223> OTHER INFORMATION: primer

<400> SEQUENCE: 25
gtgccattgc agtacatt                                                   18

<210> SEQ ID NO 26
<211> LENGTH: 17
<212> TYPE: DNA
<213> ORGANISM: Artificial
<220> FEATURE:
<223> OTHER INFORMATION: primer

<400> SEQUENCE: 26
agcaggctat cagagtg                                                    17

<210> SEQ ID NO 27
<211> LENGTH: 20
<212> TYPE: DNA
<213> ORGANISM: Artificial
<220> FEATURE:
<223> OTHER INFORMATION: primer

<400> SEQUENCE: 27
cgccgctaga ggtgaaattc                                                 20

<210> SEQ ID NO 28
<211> LENGTH: 20
<212> TYPE: DNA
<213> ORGANISM: Artificial
<220> FEATURE:
<223> OTHER INFORMATION: primer

<400> SEQUENCE: 28
ctttcgctct ggtccgtctt                                                 20
```

-continued

```
<210> SEQ ID NO 29
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: Xaa is any amino acid

<400> SEQUENCE: 29

Glu Glu Asn Xaa Glu Asn Leu
1               5

<210> SEQ ID NO 30
<211> LENGTH: 498
<212> TYPE: PRT
<213> ORGANISM: Homo sapiens

<400> SEQUENCE: 30

Met Lys Arg Lys Ser Glu Arg Arg Ser Ser Trp Ala Ala Ala Pro Pro
1               5                   10                  15

Cys Ser Arg Arg Cys Ser Ser Thr Ser Pro Gly Val Lys Lys Ile Arg
            20                  25                  30

Ser Ser Thr Gln Gln Asp Pro Arg Arg Asp Pro Gln Asp Asp Val
        35                  40                  45

Tyr Leu Asp Ile Thr Asp Arg Leu Cys Phe Ala Ile Leu Tyr Ser Arg
    50                  55                  60

Pro Lys Ser Ala Ser Asn Val His Tyr Phe Ser Ile Asp Asn Glu Leu
65                  70                  75                  80

Glu Tyr Glu Asn Phe Tyr Ala Asp Phe Gly Pro Leu Asn Leu Ala Met
                85                  90                  95

Val Tyr Arg Tyr Cys Cys Lys Ile Asn Lys Lys Leu Lys Ser Ile Thr
            100                 105                 110

Met Leu Arg Lys Lys Ile Val His Phe Thr Gly Ser Asp Gln Arg Lys
        115                 120                 125

Gln Ala Asn Ala Ala Phe Leu Val Gly Cys Tyr Met Val Ile Tyr Leu
    130                 135                 140

Gly Arg Thr Pro Glu Glu Ala Tyr Arg Ile Leu Ile Phe Gly Glu Thr
145                 150                 155                 160

Ser Tyr Ile Pro Phe Arg Asp Ala Ala Tyr Gly Ser Cys Asn Phe Tyr
                165                 170                 175

Ile Thr Leu Leu Asp Cys Phe His Ala Val Lys Lys Ala Met Gln Tyr
            180                 185                 190

Gly Phe Leu Asn Phe Asn Ser Phe Asn Leu Asp Glu Tyr Glu His Tyr
        195                 200                 205

Glu Lys Ala Glu Asn Gly Asp Leu Asn Trp Ile Ile Pro Asp Arg Phe
    210                 215                 220

Ile Ala Phe Cys Gly Pro His Ser Arg Ala Arg Leu Glu Ser Gly Tyr
225                 230                 235                 240

His Gln His Ser Pro Glu Thr Tyr Ile Gln Tyr Phe Lys Asn His Asn
                245                 250                 255

Val Thr Thr Ile Ile Arg Leu Asn Lys Arg Met Tyr Asp Ala Lys Arg
            260                 265                 270

Phe Thr Asp Ala Gly Phe Asp His His Asp Leu Phe Phe Ala Asp Gly
        275                 280                 285

Ser Thr Pro Thr Asp Ala Ile Val Lys Glu Phe Leu Asp Ile Cys Glu
    290                 295                 300
```

```
Asn Ala Glu Gly Ala Ile Ala Val His Cys Lys Ala Gly Leu Gly Arg
305                 310                 315                 320

Thr Gly Thr Leu Ile Ala Cys Tyr Ile Met Lys His Tyr Arg Met Thr
            325                 330                 335

Ala Ala Glu Thr Ile Ala Trp Val Arg Ile Cys Arg Pro Gly Ser Val
            340                 345                 350

Ile Gly Pro Gln Gln Gln Phe Leu Val Met Lys Gln Thr Asn Leu Trp
        355                 360                 365

Leu Glu Gly Asp Tyr Phe Arg Gln Lys Leu Lys Gly Gln Glu Asn Gly
    370                 375                 380

Gln His Arg Ala Ala Phe Ser Lys Leu Leu Ser Gly Val Asp Asp Ile
385                 390                 395                 400

Ser Ile Asn Gly Val Glu Asn Gln Asp Gln Gln Glu Pro Glu Pro Tyr
                405                 410                 415

Ser Asp Asp Glu Ile Asn Gly Val Thr Gln Gly Asp Arg Leu Arg
                420                 425                 430

Ala Leu Lys Ser Arg Arg Gln Ser Lys Thr Asn Ala Ile Pro Leu Thr
            435                 440                 445

Val Ile Leu Gln Ser Ser Val Gln Ser Cys Lys Thr Ser Glu Pro Asn
450                 455                 460

Ile Ser Gly Ser Ala Gly Ile Thr Lys Arg Thr Thr Arg Ser Ala Ser
465                 470                 475                 480

Arg Lys Ser Ser Val Lys Ser Leu Ser Ile Ser Arg Thr Lys Thr Val
                485                 490                 495

Leu Arg

<210> SEQ ID NO 31
<211> LENGTH: 5589
<212> TYPE: DNA
<213> ORGANISM: Homo sapiens

<400> SEQUENCE: 31
cacggaacag ccctcctggg gtccccacga gccgcgtcct gctgtgcccc ggcgcctacg      60
cagcagcggc cgcggccgcg cgtgggcacgc acggttaccc cgggcagctc cggccgccag    120
ctgcagcccc gtcgcctcgg ccgcgccagc cggctgcggg cacctggggg cgggctgggg    180
gcgccggccg cggcaggagg cgctgtagcg agggctgcgg cgccggtcct gcggcggccg    240
cgggaggcag cggggcaggc gctgtgggcc gggctcctcc tccggctcct gcgcgaccgc    300
ctcccgccgg gctctgccgg cgcccgccgt ccccgcagcg ccgctctgcg cccgccgccc    360
cgagcgcccg cgcggggctg gcgggagcct cggcgggcgc gcgggcgcgc ggggccatgg    420
tcgtggcccc ctgacgggcc gcggccgcct ccatgaagcg gaaaagcgag cggcggtcga    480
gctgggccgc cgcgccccc tgctcgcggc gctgctcgtc gacctcgccg ggtgtgaaga    540
agatccgcag ctccacgcag caagaccgcg gccgccggga ccccaggac gacgtgtacc     600 tggacatcac cgatcgcctt tgttttgcca ttctctacag cagaccaaag agtgcatcaa     660
atgtacatta tttcagcata gataatgaac ttgaatatga gaacttctac gcagattttg     720
gaccactcaa tctggcaatg gtttacagat attgttgcaa gatcaataag aaattaaagt     780
ccattacaat gttaaggaag aaaattgttc attttactgg ctctgatcag agaaaacaag     840
caaatgctgc cttccttgtt ggatgctaca tggttatata tttggggaga accccagaag     900
aagcatatag aatattaatc tttggagaga catcctatat tcctttcaga gatgctgcct     960
atggaagttg caatttctac attacacttc ttgactgttt tcatgcagta aagaaggcaa    1020
```

```
tgcagtatgg cttccttaat ttcaactcat ttaaccttga tgaatatgaa cactatgaaa    1080
aagcagaaaa tggagattta aattggataa taccagaccg atttattgcc ttctgtggac    1140
ctcattcaag agccagactt gaaagtggtt accaccaaca ttctcctgag acttatattc    1200
aatattttaa gaatcacaat gttactacca ttattcgtct gaataaaagg atgtatgatg    1260
ccaaacgctt tacggatgct ggcttcgatc accatgatct tttctttgcg gatggcagca    1320
cccctactga tgccattgtc aaagaattcc tagatatctg tgaaaatgct gagggtgcca    1380
ttgcagtaca ttgcaaagct ggccttggtc gcacgggcac tctgatagcc tgctacatca    1440
tgaagcatta caggatgaca gcagccgaga ccattgcgtg ggtcaggatc tgcagacctg    1500
gctcggtgat tgggcctcag cagcagtttt tggtgatgaa gcaaaccaac ctctggctgg    1560
aaggggacta ttttcgtcag aagttaaagg ggcaggagaa tggacaacac agagcagcct    1620
tctccaaact tctctctggc gttgatgaca tttccataaa tggggtcgag aatcaagatc    1680
agcaagaacc cgaaccgtac agtgatgatg acgaaatcaa tggagtgaca caaggtgata    1740
gacttcgggc cttgaaaagc agaagacaat ccaaaacaaa cgctattcct ctcacagtaa    1800
ttcttcaatc cagtgttcag agctgtaaaa catctgaacc taacatttct ggcagtgcag    1860
gcattactaa aagaaccacc agatctgctt caaggaaaag cagtgttaaa agtctctcca    1920
tttcaaggac taaaacagtc ttgcgttaag taaaaacctg tgaccagagc tgaaggaaga    1980
ctctaggact gaaaactgca acagaaatta gcacaatttg aaaacaaaac aaaattgcaa    2040
aagccttagt tgcttttttcc acctaagaag ttgatcaatg gagaaaatgt ccactggagt    2100
ttgaataatg aactttgagt ttgggtgcaa gcaaatgact cagagaaggg tccagctctc    2160
aagctgaatg acaaacatgc tgttgtaaat ttagtctcag gtgtaaatac caagccctc     2220 tggtacccag ggagctggct ggtctgtggt gcatgtgtgt ccctgtgatg gcaatcattg    2280
tagttgctgg ccttcagaag aattgaggat ctgatggagg ttttttatgt atttattttc    2340
tgttcacctt gtgaccctgt gtcaaaattt ataaagatac aaaaggcatt actgaaatgg    2400
tactttctgt aatttgatac tatttggctt aatcatcttc acttgactat ttgtaatact    2460
gttgtaatgt taactctgtt aagtacccaa gctgcttgtc ttccaccaaa gagtgcttta    2520
ttaacaagaa tctgtgaaaa tcacatttaa acactgttgc atgttgtaag accaggtggt    2580
accttagtaa cctaaaactt gcaagagaat attaatggta gctttagaag actcaggagg    2640
agaaactgac ttcagagttg gaagatgttg caagtcgttc cttttttctgt ccttcaggga    2700 ctgaagaact gggaggctgc ccattgtttg gttgccagtc atacaaatta aaatcatatt    2760
tccttccatg aatggaagaa acacactatt ggttttttccc cttggaaaca gcaatcccaa    2820
ataatgtcgg cttacaaaaa aaaaaagtta ccactttttt agagtccttc cctgtaacat    2880 tggattttttt ttttcccctta tgagatccac ctaaggccat tgacgtggcc tgcgatctca    2940
gtgacaatga tctgcttctg gatctcactg ttgcctttgg ttagggaaca caactagtaa    3000
ctctgcagag tgccttctcc cgcagcccta ctggaacaca gcagagtctg tgccatgaag    3060
cagttacaga aacagaattg atgtgctgct aaaaaaaaaa aaaaaaatgg ggcccgaaat    3120
aaaagaatat atagtactca cctcagttcc ttccataaga agtgggtggt ttaatgattg    3180
ttaagccatt tttgcctgtg ccgggagcat ggagggctga atgtcgaca ggcagtggga    3240 aacaaatgcc ctcctaagcc acaaggcgtg cgccagatta gtaggcaact ccatttttaag   3300 aagctgcctt tttcacaaaa ctggaagaaa taaaagcggt tggaataaac aagttaaaag    3360
tctttaatgc aaaaagtaat tgaaaggcag tgcctccatt ttggtgtact ttcttggaag    3420
```

```
aaagtataaa attgaccggc atcatgagag acggaagatg ccgtgttctc agccaaacaa    3480
gcaactcttt ccccgccagg cactgtcggg tggggtcagg ccagctttta aacactgggg    3540
actggatcac agaaaaacag tggttttctg tccctggaaa tgaataggca caaagaccca    3600
cttggctgtg ggcagactac tcttcaataa gatttgggtg ggaggaggaa cattccttt     3660 gctattttga gctgagacaa tataaatatt caaactgtgc catgcataaa gcattgaatt    3720
ctcagggcac ctcttcttcc ccttaccccct tttaaggcca tccccctccat taataataat   3780 ccaggtagtt gtgaaaatcg tgcttctatc tgatcccttc ttagtttggc ttttcatccc    3840
atcagaacaa gtaaacgtag gcgccacagc tcttgtgagt actgtctccc tcacggtgaa    3900
tgagcctcct ggtgtttcgt ccaagaaaag aaagggtgtc actggaacca cagccccttt    3960 tcatttttata aactgcctct tcatgttgcc tgctcaagtt tccacctaga attgctatca   4020
ctgtggctct ttctaaaaat cttctatttt aactggttca ctgaaattag tcatagaaaa    4080
cttgtgattt ggtgaagagg cattccttgt aataaccaaa tgacttggga tggtgtgcat    4140
agcaagggca gtgttacact tatgaggact gtctctagca tccaggaagt ctctgggtct    4200
gagggatgga aagttcttcc tgctatgaat gagagtggac tcttcccctc acccccaact    4260
gaaaccacaa acaaccagaa tcttctggaa ttctgactta gagtcgttgt tatagaagac    4320
cttgttgcta tggaacatga aactgtgtgt cagatggaga gatcccctta acctaagagc    4380
cttaaatagc cctgaaagta cactgggacg gtttgcgatg gaattaaaat tggaagtgaa    4440 tattttttagg tgctcttgaa gctttctggg gactcaaaat tatcaaaagt cagggacagt    4500
ccggaggaag agcgtctgca aaactgggtt cctagaagta tagacggact tagcttttg    4560 tagaatttgg tgaggagcag cgcctcgtga gagcagaatg gcctggcgtg gccagtgctt    4620
cccggcagca cgcagctctg cggcctccag aattcccctg ttctgagctt gatgccccta    4680
gcctgtcccc tacctacttc ctcccctcct ctctagccct ctcacagggg tgattgctac    4740
ctctctgttt tcttgggcct aggcaagttt tagaggagtt cccaagcatt gttatgaggc    4800
cagtgtgctc gctgggctgg gcgggatggc ctgggcttgt gtgtggcctg agggctctcc    4860
tggggccttc tcttttccca gtcaccttttg gagccacaga agcagtgcac tcattggatg   4920
tctgttctta acacagcttc tctttctaca ttaaaaaaaa tcattattgc attttggaaa    4980
gcagtgctca tcaaaagcaa cttttaaaac ctattttatt gttcctttaa atgttctctc    5040
ccgctgaaac tgccctggag aggctatctg ctgctcttcc atttacccac atcaggttat    5100
tctccatgtc actcagtgga gatgactcca gatgtgttta aagactggac aattcaccta    5160
tactgtgtag gaaattacct ccttaattac ctggtagaat tgtcagcaga catgttcatc    5220
cgatgatagt actgcagttt tctattaata atttgcagac ttttatctaa cctgcactca    5280
tgtacagatt attaaaagtt ttaaaatgta actgatcagt attgatcaat cattgtcttg    5340 atttttttttt acagcgtata tttctaatca tattttttaa agccaagaga actggttgaa    5400
tgaatgttta ttttcctgaa ggtatttta agataaagct tcctaatggc gtgtaaactt     5460
tgcatatgta tgtagtttga tacatattgt cacatttgaa aatcttgtgg gttgtaactg    5520
gttttataca aaatatcgaa tagtggaaat tgtataatta caatcatgta attaaaagta    5580
ttaacccaa                                                            5589

<210> SEQ ID NO 32
<211> LENGTH: 461
<212> TYPE: PRT
<213> ORGANISM: Homo sapiens
```

```
<400> SEQUENCE: 32

Met Ser Arg Glu Gly Ala Gly Ala Ala Leu Val Ala Glu Val Ile Lys
1               5                   10                  15

Asp Arg Leu Cys Phe Ala Ile Leu Tyr Ser Arg Pro Lys Ser Ala Ser
            20                  25                  30

Asn Val His Tyr Phe Ser Ile Asp Asn Glu Leu Glu Tyr Glu Asn Phe
        35                  40                  45

Tyr Ala Asp Phe Gly Pro Leu Asn Leu Ala Met Val Tyr Arg Tyr Cys
    50                  55                  60

Cys Lys Ile Asn Lys Lys Leu Lys Ser Ile Thr Met Leu Arg Lys Lys
65                  70                  75                  80

Ile Val His Phe Thr Gly Ser Asp Gln Arg Lys Gln Ala Asn Ala Ala
                85                  90                  95

Phe Leu Val Gly Cys Tyr Met Val Ile Tyr Leu Gly Arg Thr Pro Glu
            100                 105                 110

Glu Ala Tyr Arg Ile Leu Ile Phe Gly Glu Thr Ser Tyr Ile Pro Phe
        115                 120                 125

Arg Asp Ala Ala Tyr Gly Ser Cys Asn Phe Tyr Ile Thr Leu Leu Asp
    130                 135                 140

Cys Phe His Ala Val Lys Lys Ala Met Gln Tyr Gly Phe Leu Asn Phe
145                 150                 155                 160

Asn Ser Phe Asn Leu Asp Glu Tyr Glu His Tyr Glu Lys Ala Glu Asn
                165                 170                 175

Gly Asp Leu Asn Trp Ile Ile Pro Asp Arg Phe Ile Ala Phe Cys Gly
            180                 185                 190

Pro His Ser Arg Ala Arg Leu Glu Ser Gly Tyr His Gln His Ser Pro
        195                 200                 205

Glu Thr Tyr Ile Gln Tyr Phe Lys Asn His Asn Val Thr Thr Ile Ile
    210                 215                 220

Arg Leu Asn Lys Arg Met Tyr Asp Ala Lys Arg Phe Thr Asp Ala Gly
225                 230                 235                 240

Phe Asp His His Asp Leu Phe Phe Ala Asp Gly Ser Thr Pro Thr Asp
                245                 250                 255

Ala Ile Val Lys Glu Phe Leu Asp Ile Cys Glu Asn Ala Glu Gly Ala
            260                 265                 270

Ile Ala Val His Cys Lys Ala Gly Leu Gly Arg Thr Gly Thr Leu Ile
        275                 280                 285

Ala Cys Tyr Ile Met Lys His Tyr Arg Met Thr Ala Ala Glu Thr Ile
    290                 295                 300

Ala Trp Val Arg Ile Cys Arg Pro Gly Ser Val Ile Gly Pro Gln Gln
305                 310                 315                 320

Gln Phe Leu Val Met Lys Gln Thr Asn Leu Trp Leu Glu Gly Asp Tyr
                325                 330                 335

Phe Arg Gln Lys Leu Lys Gly Gln Glu Asn Gly His Arg Ala Ala
            340                 345                 350

Phe Ser Lys Leu Leu Ser Gly Val Asp Ile Ser Ile Asn Gly Val
        355                 360                 365

Glu Asn Gln Asp Gln Gln Glu Pro Glu Pro Tyr Ser Asp Asp Asp Glu
    370                 375                 380

Ile Asn Gly Val Thr Gln Gly Asp Arg Leu Arg Ala Leu Lys Ser Arg
385                 390                 395                 400

Arg Gln Ser Lys Thr Asn Ala Ile Pro Leu Thr Val Ile Leu Gln Ser
                405                 410                 415
```

```
Ser Val Gln Ser Cys Lys Thr Ser Glu Pro Asn Ile Ser Gly Ser Ala
        420                 425                 430

Gly Ile Thr Lys Arg Thr Thr Arg Ser Ala Ser Arg Lys Ser Ser Val
        435                 440                 445

Lys Ser Leu Ser Ile Ser Arg Thr Lys Thr Val Leu Arg
        450                 455                 460

<210> SEQ ID NO 33
<211> LENGTH: 5131
<212> TYPE: DNA
<213> ORGANISM: Homo sapiens

<400> SEQUENCE: 33
cctttaaact tgttttttta aacttcgggg gtgtggtcgc ggcgcctccc ctctcggcgg      60
ctggcagtcc ttgcctctgc cccgccttcc agatgctttg gagtcatgag ccgggagggc     120 gcggggcag  ctttggtagc cgaggtgatc aaagatcgcc tttgttttgc cattctctac     180
agcagaccaa agagtgcatc aaatgtacat tatttcagca tagataatga acttgaatat     240
gagaacttct acgcagattt tggaccactc aatctggcaa tggttacag atattgttgc      300 aagatcaata agaaattaaa gtccattaca atgttaagga agaaaattgt tcattttact     360
ggctctgatc agagaaaaca agcaaatgct gccttccttg ttggatgcta catggttata     420
tatttgggga gaaccccaga agaagcatat agaatattaa tctttggaga gacatcctat     480
attcctttca gagatgctgc ctatggaagt tgcaatttct acattacact tcttgactgt     540
tttcatgcag taaagaaggc aatgcagtat ggcttcctta atttcaactc atttaaccct     600
gatgaatatg aacactatga aaaagcagaa aatggagatt taaattggat aataccagac     660
cgatttattg ccttctgtgg acctcattca agagccagac ttgaaagtgg ttaccaccaa     720
cattctcctg agacttatat tcaatatttt aagaatcaca atgttactac cattattcgt     780
ctgaataaaa ggatgtatga tgccaaacgc tttacggatg ctggcttcga tcaccatgat     840
cttttctttg cggatggcag caccccctact gatgccattg tcaaagaatt cctagatatc     900
tgtgaaaatg ctgagggtgc cattgcagta cattgcaaag ctggccttgg tcgcacgggc     960
actctgatag cctgctacat catgaagcat acaggatga cagcagccga gaccattgcg    1020
tgggtcagga tctgcagacc tggctcggtg attgggcctc agcagcagtt tttggtgatg    1080
aagcaaacca acctctggct ggaagggggac tattttcgtc agaagttaaa ggggcaggag    1140
aatggacaac acagagcagc cttctccaaa cttctctctg gcgttgatga catttccata    1200
aatggggtcg agaatcaaga tcagcaagaa cccgaaccgt acagtgatga tgacgaaatc    1260
aatggagtga cacaaggtga tagacttcgg gccttgaaaa gcagaagaca atccaaaaca    1320
aacgctattc ctctcacagt aattcttcaa tccagtgttc agagctgtaa aacatctgaa    1380
cctaacattt ctggcagtgc aggcattact aaaagaacca ccagatctgc ttcaggaaa     1440 agcagtgtta aaagtctctc catttcaagg actaaaacag tcttgcgtta agtaaaaacc    1500
tgtgaccaga gctgaaggaa gactctagga ctgaaaactg caacagaaat tagcacaatt    1560
tgaaaacaaa acaaaattgc aaaagcctta gttgcttttt ccacctaaga agttgatcaa    1620
tggagaaaat gtccactgga gtttgaataa tgaactttga gtttgggtgc aagcaaatga    1680
ctcagagaag ggtccagctc tcaagctgaa tgacaaacat gctgttgtaa atttagtctc    1740
aggtgtaaat acccaagccc tctggtaccc agggagctgg ctggtctgtg gtgcatgtgt    1800
gtccctgtga tggcaatcat tgtagttgct ggccttcaga agaattgagg atctgatgga    1860
```

-continued

```
ggtttttat    gtatttattt   tctgttcacc   ttgtgaccct   gtgtcaaaat   ttataaagat   1920
acaaaaggca   ttactgaaat   ggtacttct    gtaatttgat   actatttggc   ttaatcatct   1980
tcacttgact   atttgtaata   ctgttgtaat   gttaactctg   ttaagtaccc   aagctgcttg   2040
tcttccacca   aagagtgctt   tattaacaag   aatctgtgaa   atcacattt    aaacactgtt   2100
gcatgttgta   agaccaggtg   gtaccttagt   aacctaaaac   ttgcaagaga   atattaatgg   2160
tagctttaga   agactcagga   ggagaaactg   acttcagagt   tggaagatgt   tgcaagtcgt   2220
tccttttct    gtccttcagg   gactgaagaa   ctgggaggct   gcccattgtt   tggttgccag   2280
tcatacaaat   taaaatcata   tttccttcca   tgaatggaag   aaacacacta   ttggtttttc   2340
cccttggaaa   cagcaatccc   aaataatgtc   ggcttacaaa   aaaaaaagt    taccacttt    2400
ttagagtcct   tccctgtaac   attggatttt   tttttcct     tatgagatcc   acctaaggcc   2460
attgacgtgg   cctgcgatct   cagtgacaat   gatctgcttc   tggatctcac   tgttgccttt   2520
ggttagggaa   cacaactagt   aactctgcag   agtgccttct   cccgcagccc   tactggaaca   2580
cagcagagtc   tgtgccatga   agcagttaca   gaaacagaat   tgatgtgctg   ctaaaaaaaa   2640
aaaaaaaat    ggggcccgaa   ataaaagaat   atatagtact   cacctcagtt   ccttccataa   2700
gaagtgggtg   gtttaatgat   tgttaagcca   ttttgcctg    tgccgggagc   atggagggct   2760
gagatgtcga   caggcagtgg   gaaacaaatg   ccctcctaag   ccacaaggcg   tgcgccagat   2820
tagtaggcaa   ctccatttta   agaagctgcc   ttttcacaa    aactgaaga    aataaagcg   2880
gttggaataa   acaagttaaa   agtctttaat   gcaaaaagta   attgaaaggc   agtgcctcca   2940
ttttggtgta   ctttcttgga   agaaagtata   aaattgaccg   gcatcatgag   agacggaaga   3000
tgccgtgttc   tcagccaaac   aagcaactct   tccccgcca    ggcactgtcg   ggtgggtca    3060
ggccagcttt   taaacactgg   ggactggatc   acagaaaaac   agtggttttc   tgtccctgga   3120
aatgaatagg   cacaaagacc   cacttggctg   tgggcagact   actcttcaat   aagatttggg   3180
tgggaggagg   aacattcctt   ttgctatttt   gagctgagac   aatataaata   ttcaaactgt   3240
gccatgcata   aagcattgaa   ttctcagggc   acctcttctt   cccttaccc    cttttaaggc   3300
catcccctcc   attaataata   atccaggtag   ttgtgaaaat   cgtgcttcta   tctgatccct   3360
tcttagtttg   gcttttcatc   ccatcagaac   aagtaaacgt   aggcgccaca   gctcttgtga   3420
gtactgtctc   cctcacggtg   aatgagcctc   ctggtgtttc   gtccaagaaa   agaaagggtg   3480
tcactggaac   cacagccctt   tttcattta    taaactgcct   cttcatgttg   cctgctcaag   3540
tttccaccta   gaattgctat   cactgtggct   ctttctaaaa   atctttctat   ttaactggtt   3600
cactgaaatt   agtcatagaa   aacttgtgat   ttggtgaaga   ggcattcctt   gtaataacca   3660
aatgacttgg   gatggtgtgc   atagcaaggg   cagtgttaca   cttatgagga   ctgtctctag   3720
catccaggaa   gtctctgggt   ctgagggatg   gaaagttctt   cctgctatga   atgagagtgg   3780
actcttcccc   tcacccccaa   ctgaaaccac   aaacaaccag   aatcttctgg   aattctgact   3840
tagagtcgtt   gttatagaag   accttgttgc   tatggaacat   gaaactgtgt   gtcagatgga   3900
gagatcccct   taacctaaga   gccttaaata   gccctgaaag   tacactggga   cggtttgcga   3960
tggaattaaa   attggaagtg   aatattttta   ggtgctcttg   aagctttctg   gggactcaaa   4020
attatcaaaa   gtcagggaca   gtccggagga   agagcgtctg   caaaactggg   ttcctagaag   4080
tatagacgga   cttagctttt   tgtagaattt   ggtgaggagc   agcgcctcgt   gagagcagaa   4140
tggcctggcg   tggccagtgc   ttcccggcag   cacgcagctc   tgcggcctcc   agaattcccc   4200
tgttctgagc   ttgatgcccc   tagcctgtcc   cctacctact   tcctcccctc   ctctctagcc   4260
```

```
ctctcacagg ggtgattgct acctctctgt tttcttgggc ctaggcaagt tttagaggag    4320
ttcccaagca ttgttatgag gccagtgtgc tcgctgggct gggcgggatg gcctgggctt    4380
gtgtgtggcc tgagggctct cctggggcct tctcttttcc cagtcacctt tggagccaca    4440
gaagcagtgc actcattgga tgtctgttct taacacagct tctctttcta cattaaaaaa    4500
aatcattatt gcattttgga aagcagtgct catcaaaagc aacttttaaa acctatttta    4560
ttgttccttt aaatgttctc tcccgctgaa actgccctgg agaggctatc tgctgctctt    4620
ccatttaccc acatcaggtt attctccatg tcactcagtg gagatgactc cagatgtgtt    4680
taaagactgg acaattcacc tatactgtgt aggaaattac ctccttaatt acctggtaga    4740
attgtcagca gacatgttca tccgatgata gtactgcagt tttctattaa taatttgcag    4800
acttttatct aacctgcact catgtacaga ttattaaaag ttttaaaatg taactgatca    4860
gtattgatca atcattgtct tgatttttt ttacagcgta tatttctaat catattttt    4920 aaagccaaga gaactggttg aatgaatgtt tattttcctg aaggtatttt taagataaag    4980
cttcctaatg gcgtgtaaac tttgcatatg tatgtagttt gatacatatt gtcacatttg    5040
aaaatcttgt gggttgtaac tggttttata caaaatatcg aatagtggaa attgtataat    5100
tacaatcatg taattaaaag tattaaccca a                                    5131
```